United States Patent
Schwarz et al.

(10) Patent No.: US 10,273,226 B2
(45) Date of Patent: Apr. 30, 2019

(54) PYRAZOLYL-HETEROARYLAMIDES AS PESTICIDES

(71) Applicant: Bayer Animal Health GmbH, Leverkusen (DE)

(72) Inventors: Hans-Georg Schwarz, Dorsten (DE); Michael Maue, Langenfeld (DE); Kerstin Ilg, Köln (DE); Ulrich Görgens, Ratingen (DE); Andreas Turberg, Haan (DE); Sebastian Horstmann, Leverkusen (DE); Johannes Köbberling, Neuss (DE); Niels Lindner, Wuppertal (DE)

(73) Assignee: BAYER ANIMAL HEALTH GMBH, Leverkusen (DE)

(*) Notice: Subject to any disclaimer, the term of this patent is extended or adjusted under 35 U.S.C. 154(b) by 0 days.

(21) Appl. No.: 15/109,630

(22) PCT Filed: Dec. 30, 2014

(86) PCT No.: PCT/EP2014/079440
§ 371 (c)(1),
(2) Date: Jul. 2, 2016

(87) PCT Pub. No.: WO2015/101622
PCT Pub. Date: Jul. 9, 2015

(65) Prior Publication Data
US 2016/0326140 A1 Nov. 10, 2016

(30) Foreign Application Priority Data
Jan. 3, 2014 (EP) ..................... 14150153

(51) Int. Cl.
| | |
|---|---|
| *C07D 403/04* | (2006.01) |
| *C07D 401/14* | (2006.01) |
| *C07D 231/38* | (2006.01) |
| *A01N 43/56* | (2006.01) |
| *A01N 43/76* | (2006.01) |
| *A01N 43/90* | (2006.01) |
| *C07D 403/14* | (2006.01) |
| *C07D 407/14* | (2006.01) |
| *C07D 409/14* | (2006.01) |
| *C07D 413/14* | (2006.01) |
| *C07D 487/04* | (2006.01) |

(52) U.S. Cl.
CPC ......... *C07D 403/04* (2013.01); *A01N 43/56* (2013.01); *A01N 43/76* (2013.01); *A01N 43/90* (2013.01); *C07D 231/38* (2013.01); *C07D 401/14* (2013.01); *C07D 403/14* (2013.01); *C07D 407/14* (2013.01); *C07D 409/14* (2013.01); *C07D 413/14* (2013.01); *C07D 487/04* (2013.01)

(58) Field of Classification Search
CPC .. C07D 403/04; C07D 231/38; C07D 401/14; C07D 403/14; C07D 407/14; C07D 409/14; C07D 413/14; C07D 487/04; A01N 43/56; A01N 43/76; A01N 43/90
See application file for complete search history.

(56) References Cited

U.S. PATENT DOCUMENTS

2006/0069132 A1 3/2006 Armel et al.

FOREIGN PATENT DOCUMENTS

| | | |
|---|---|---|
| EP | 1911751 | 4/2008 |
| WO | 2000/007980 | 2/2000 |
| WO | 2004/035545 | 4/2004 |
| WO | 2004/106324 | 12/2004 |
| WO | 2008/029084 | 3/2008 |
| WO | 2010/051926 | 5/2010 |
| WO | 2012/069366 | 5/2012 |
| WO | 2012/080376 | 6/2012 |
| WO | 2012/107434 | 8/2012 |
| WO | 2014/122083 | 8/2014 |

(Continued)

OTHER PUBLICATIONS

Wang et al. (Chinese Chemical Letters 26 (2015) 672-674).*
Ye et al. (Environmental Pollution 158 (2010), p. 2371-2383).*
Wu et al. (Chinese Chemical Letters 28 (2017), p. 121-125).*
Patani et al. (Chem. Rev., 1996, vol. 96, No. 8, p. 3147-3176).*
Parlow, "Synthesis of Pyrazolecarbonylaminopyridinecarboxamides as Herbicides,"J. Heterocycl. Chem., 35(6), 1998, pp. 1493-1499.

(Continued)

*Primary Examiner* — Robert H Havlin
(74) *Attorney, Agent, or Firm* — McBee Moore Woodward & Vanik IP, LLC

(57) ABSTRACT

The invention comprises, inter alia, pyrazolylheteroarylamides of the general formula (I)

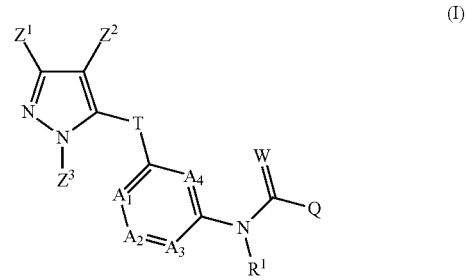

in which the $A_1$-$A_4$, T, W, Q, $R^1$ and $Z^1$-$Z^3$ radicals are each as defined in the description. Also described are processes for preparing the compounds of the formula (I). The inventive compounds are especially suitable for controlling insects, arachnids and nematodes in agriculture and ectoparasites in veterinary medicine.

17 Claims, No Drawings

(56) References Cited

FOREIGN PATENT DOCUMENTS

WO 2014/135437 9/2014
WO 2014/135439 9/2014

OTHER PUBLICATIONS

Parlow, et al., "Utility of Complementary Molecular Reactiveity and Molecular Recognition (CMR/R) Technology and Polymer-Supported Reagents in the Solution-Phase Synthesis of Heterocyclic Carboxamides," J. Org. Chem., 62(17), 1997, pp. 5908-5919.
European Patent Office, International Search Report and Written Opinion for International Patent Application No. PCT/EP2014/079440, dated Mar. 9, 2015, 10 pages.

* cited by examiner

PYRAZOLYL-HETEROARYLAMIDES AS PESTICIDES

CROSS-REFERENCE TO RELATED APPLICATIONS

This application is a U.S. national phase application of International Patent Application No. PCT/EP2014/079440, filed Dec. 30, 2014 and titled NOVEL PYRAZOLYL-HETEROARYLAMIDES AS PESTICIDES, which claims priority to European Patent Application No. 14150153.6, filed Jan. 3, 2014 and titled NOVEL PYRAZOLYL-HETEROARYLAMIDES AS PESTICIDES, the contents of both of which are incorporated herein by reference in their entirety.

The present application relates to novel pyrazolylheteroarylamides, to processes for preparation thereof and to the use thereof for controlling animal pests, particularly arthropods and especially insects, arachnids and nematodes.

It is known that particular halogen-substituted compounds are herbicidally active (cf. J. Org. Chem. 1997, 62(17), 5908-5919, J. Heterocycl. Chem. 1998, 35(6), 1493-1499, WO 2004/035545, WO 2004/106324, US 2006/069132, WO 2008/029084).

It is also known that particular halogen-substituted compounds are insecticidally active (EP 1 911 751, WO 2010/051926, WO 2012/069366, WO 2012/080376, WO 2012/107434, WO 2014/122083, WO 2014/135439 and WO 2014/135437).

It is additionally known that particular halogen-substituted compounds have cytokine-inhibiting activities (WO 2000/07980).

Modern crop protection compositions have to meet many demands, for example in relation to the level, duration and spectrum of their action and possible use. Important questions relate to toxicity and combinability with other active ingredients or formulation auxiliaries, and also to the complexity of the synthesis of an active ingredient. In addition, resistances can occur. For all these reasons, the search for novel crop protection compositions can never be considered to be complete, and there is a constant need for novel compounds having improved properties compared to the known compounds at least in relation to individual aspects.

It was an object of the present invention to provide compounds which broaden the spectrum of the pesticides in various aspects and/or improve their activity.

It has now been found that, surprisingly, particular pyrazolylheteroarylamides and the N-oxides and salts thereof have biological properties and are especially suitable for control of animal pests, and therefore have particularly good usability in the agrochemical sector and in the field of animal health.

Similar compounds have already become known from WO 2012/080376. This application describes 1,2,3-triazole-benzanilides as insecticidal compounds; no other heteroaroylbenzanilides are described.

SUMMARY

The invention relates to compounds of the general formula (Ic)

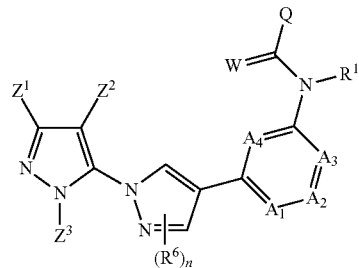

in which
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl;
the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;
$R^2$, $R^3$, $R^4$ and $R^5$ are each independently hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;
if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
if neither of the $A_1$ and $A_2$ moieties is nitrogen, $R^2$ and $R^3$ together with the carbon atom to which they are bonded may form a 5- or 6-membered ring containing 0, 1 or 2 nitrogen atoms and/or 0 or 1 oxygen atom and/or 0 or 1 sulphur atom;
W is oxygen or sulphur;
Q is hydrogen, amino or one of the following optionally substituted moieties: alkyl, alkyloxy, alkenyl, alkynyl, cycloalkyl, heterocyclyl, cycloalkylalkyl, arylalkyl, heteroarylalkyl, alkoxycarbonyl, or an N-alkylamino, N-alkylcarbonylamino, N,N-dialkylamino, alkylsulphonylamino moiety; or
Q is an optionally mono- to penta-V-substituted aryl, or an optionally mono- to penta-V-substituted heteroaryl, where
V is halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino;
$R^6$ is independently halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n has the values of 0-2 (when n=0, $R^6$ is correspondingly H);
$Z^1$ is an optionally substituted alkyl or cycloalkyl, and
$Z^2$ is hydrogen, halogen, cyano, nitro, amino or an optionally substituted alkyl, alkylcarbonyl, alkylsulphanyl, alkylsulphinyl, alkylsulphonyl, and
$Z^3$ is hydrogen or an optionally substituted alkyl, cycloalkyl, alkenyl, alkynyl, aryl or hetaryl.

A preferred embodiment relates to inventive compounds as described above in the summary, where $R^1$ is hydrogen or an optionally independently with halogen, cyano, alkoxy or alkoxycarbonyl mono- to hepta-substituted $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl;

the following chemical moieties are as follows:

$A_1$ is $CR^2$ or nitrogen,
$A_2$ is $CR^3$ or nitrogen,
$A_3$ is $CR^4$ or nitrogen, and
$A_4$ is $CR^5$ or nitrogen, but not more than three of the chemical moieties $A_1$ to $A_4$ are simultaneously nitrogen;

$R^2$, $R^3$, $R^4$ and $R^5$ are each independently hydrogen, halogen, cyano, nitro, or an optionally independently with halogen, cyano, alkoxy or alkoxycarbonyl mono- to hepta-substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

W is oxygen or sulphur;

Q is hydrogen, amino or one of the following independently with hydroxy, nitro, amino, halogen, alkoxy, cyano, hydroxycarbonyl, alkoxycarbonyl, alkylcarbamoyl, cycloalkylcarbamoyl, phenyl mono- to hepta-substituted moieties: $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_1$-$C_6$-hydroxyalkyl, aryl($C_1$-$C_3$)-alkyl, heteroaryl($C_1$-$C_3$)-alkyl, $C_1$-$C_4$-alkoxycarbonyl, N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino; or Q is hydrogen, amino or one of the moieties selected from $C_1$-$C_6$-alkyl, $C_1$-$C_6$-alkyloxy, $C_2$-$C_6$-alkenyl, $C_2$-$C_6$-alkynyl, $C_3$-$C_6$-cycloalkyl, 5- or 6-membered heterocyclyl, $C_1$-$C_6$-alkyl-$C_3$-$C_6$-cycloalkyl, $C_3$-$C_6$-cycloalkyl-$C_1$-$C_6$-alkyl, $C_6$-$C_{10}$-aryl-($C_1$-$C_3$)-alkyl, 5- or -6 membered heteroaryl-($C_1$-$C_3$)-alkyl, $C_1$-$C_4$-alkoxycarbonyl, each of which is optionally independently substituted by 1, 2, 3, 4, 5, 6 or 7 substituents selected from the group consisting of hydroxy, nitro, amino, halogen, oxo, benzyloxy, $C_3$-$C_6$-cycloalkyl, $C_1$-$C_6$-alkoxy, $C_1$-$C_6$-haloalkoxy, cyano, hydroxycarbonyl, $C_1$-$C_4$-alkoxycarbonyl, $C_1$-$C_6$-alkylcarbamoyl, $C_3$-$C_6$-cycloalkylcarbamoyl, N,N-di-$C_1$-$C_4$-alkylamino, phenyl optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, phenylthio optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, phenyloxy optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, 5- or 6-membered heteroaryl (e.g. pyrazolyl) optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, or is an N—$C_1$-$C_4$-alkylamino, N—$C_1$-$C_4$-alkylcarbonylamino, $C_1$-$C_4$-alkylsulphonylamino moiety; or Q is an aryl substituted by 0, 1, 2, 3 or 4 V substituents or a 5- or 6-membered heteroaryl substituted by 0, 1, 2, 3 or 4 V substituents, or Q is a bicyclic heterocycle substituted by 0, 1, 2, 3 or 4 V substituents or a bicyclic carbocycle substituted by 0, 1, 2, 3 or 4 V substituents; where V is independently halogen, cyano, nitro or an optionally independently with halogen, cyano, alkoxy or alkoxycarbonyl mono- to hepta-substituted $C_1$-$C_6$-alkyl, $C_1$-$C_6$-haloalkyl, $C_2$-$C_4$-alkenyl, $C_2$-$C_4$-alkynyl, $C_3$-$C_6$-cycloalkyl, $C_1$-$C_6$-alkoxy, $C_1$-$C_6$-haloalkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

$R^6$ is independently halogen, cyano, nitro, amino or an optionally mono- to hepta-halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n has the values of 0-1;

$Z^1$ is an optionally independently with halogen, cyano, alkoxy or alkoxycarbonyl mono- to hepta-substituted $C_1$-$C_6$-alkyl, $C_3$-$C_6$-cycloalkyl, and $Z^2$ is hydrogen, halogen, cyano, nitro, amino or an independently with halogen, cyano, alkoxy or alkoxycarbonyl mono- to hepta-substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ is hydrogen or an optionally independently halogen, cyano, alkoxy and alkoxycarbonyl mono- to hepta-substituted $C_1$-$C_6$-alkyl, $C_3$-$C_6$-cycloalkyl, $C_3$-$C_4$-alkenyl, $C_3$-$C_4$-alkynyl, or is an optionally independently with halogen, cyano, alkoxy and alkoxycarbonyl mono- to penta-substituted aryl or hetaryl.

A further preferred embodiment relates to inventive compounds as described above in the summary, in which $R^1$ is hydrogen, $C_1$-$C_4$-alkyl, $C_3$-$C_4$-alkenyl, $C_3$-$C_4$-alkynyl;
the following chemical moieties are as follows:
$A_1$ is $CR^2$,
$A_2$ is $CR^3$ or nitrogen,
$A_3$ is $CR^4$, and
$A_4$ is $CR^5$;
W is oxygen;
$R^6$ is $C_1$-$C_4$-alkyl;
n has the values of 0-1;
$Z^1$ is an in each case optionally mono- to hepta-halogen- or -cyano-substituted $C_1$-$C_6$-alkyl or $C_3$-$C_6$-cycloalkyl;
$Z^2$ is an in each case optionally mono- to hepta-halogen- or -cyano-substituted $C_1$-$C_6$-alkyl or $C_3$-$C_6$-cycloalkyl;
$Z^3$ is hydrogen or $C_1$-$C_6$-alkyl.

A further preferred embodiment relates to inventive compounds as described above in the summary, in which $R^1$ is hydrogen, methyl, ethyl, n-propyl, isopropyl, n-butyl, isobutyl, s-butyl or t-butyl, more preferably hydrogen;
the following chemical moieties are as follows:
$A_1$ is $CR^2$,
$A_2$ is $CR^3$ or nitrogen,
$A_3$ is $CR^4$, and
$A_4$ is $CR^5$;
W is oxygen;
$R^6$ is hydrogen (n=0);
$Z^1$ is an in each case optionally mono- to hepta-halogen-substituted
$Z^2$ is an in each case optionally mono- to hepta-halogen-substituted
$Z^3$ is $C_1$-$C_6$-alkyl.

A further preferred embodiment relates to inventive compounds as described above in the summary, in which $R^2$ and $R^5$ are each independently hydrogen, fluorine, chlorine, bromine, iodine, methyl and methoxy;

$R^3$ and $R^4$ are each independently hydrogen, fluorine, chlorine, bromine, iodine, cyano, nitro, $C_1$-$C_4$-alkyl, $C_1$-$C_4$-haloalkyl.

A further preferred embodiment relates to inventive compounds as described above in the summary, in which
$R^2$ and $R^5$ are each independently hydrogen or fluorine;
$R^3$ is hydrogen; and
$R^4$ is hydrogen, fluorine, chlorine or methyl.

A further preferred embodiment relates to inventive compounds as described above in the summary, in which
Q is hydrogen;
or
$C_1$-$C_6$-alkyl optionally substituted by 1, 2, 3 or 4 substituents selected independently from the group consisting of
fluorine,
chlorine,
bromine,
iodine,
cyano,
oxo,
methoxy,
benzyloxy,
ethoxy,
N,N-di-$C_1$-$C_4$-alkylamino,
phenylthio optionally independently substituted by 1, 2, 3 or 4 substituents selected from the group consisting of fluorine, chlorine, bromine, iodine, methoxy, methyl and trifluoromethyl,
phenyloxy optionally independently substituted by 1, 2, 3 or 4 substituents selected from the group consisting of fluorine, chlorine, bromine, iodine, methoxy, methyl and trifluoromethyl,
phenyl optionally independently substituted by 1, 2, 3 or 4 substituents selected from the group consisting of fluorine, chlorine, bromine, iodine, methoxy, methyl and trifluoromethyl,
thiophenyl optionally independently substituted by 1, 2, 3 or 4 substituents selected from the group consisting of fluorine, chlorine, bromine, iodine, methoxy, methyl and trifluoromethyl,
pyrazolyl optionally independently substituted by 1, 2, 3 or 4 substituents selected from the group consisting of fluorine, chlorine, bromine, iodine, methoxy, methyl and trifluoromethyl, and
$C_3$-$C_6$-cycloalkyl;
or
$C_3$-$C_6$-cycloalkyl optionally substituted by 1, 2, 3 or 4 substituents selected independently from the group consisting of
methoxy,
fluorine,
chlorine,
bromine,
iodine,
cyano,
methyl,
phenyl optionally independently substituted by 1, 2, 3 or 4 substituents selected from the group consisting of fluorine, chlorine, bromine, iodine, methoxy, methyl and trifluoromethyl;
or
Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, benzothiophenyl, benzofuranyl, [1,2,4]triazolo pyrimidinyl, 1,3-benzodioxolyl or tetralinyl, where
V is independently fluorine, chlorine, bromine, iodine, cyano, nitro, methyl, ethyl, propyl, butyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-di-$C_1$-$C_4$-alkylamino (e.g. N,N-dimethylamino).

A further preferred embodiment relates to inventive compounds as described above in the summary, in which
Q is $C_1$-$C_6$-alkyl optionally substituted by 1, 2, 3 or 4 substituents selected independently from the group consisting of
fluorine,
oxo,
methoxy,
benzyloxy,
ethoxy,
N,N-dimethylamino,
phenylthio,
phenyloxy,
$C_3$-$C_6$-cycloalkyl,
phenyl optionally independently substituted by 1, 2, 3 or 4 substituents selected from the group consisting of fluorine, chlorine and trifluoromethyl,
thiophenyl optionally substituted by 1, 2, 3 or 4 trifluoromethyl, and
pyrazolyl optionally independently substituted by 1, 2, 3 or 4 substituents selected from the group consisting of methyl and trifluoromethyl;
or
$C_3$-$C_6$-cycloalkyl optionally substituted by 1, 2, 3 or 4 substituents selected independently from the group consisting of
methoxy,
chlorine,
cyano,
methyl,
phenyl optionally independently substituted by 1, 2, 3 or 4 substituents selected from the group consisting of chlorine, methyl and trifluoromethyl;
or
Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, benzothiophenyl, benzofuranyl, [1,2,4]triazolo[1,5-a]pyrimidinyl, 1,3-benzodioxolyl or tetralinyl, where
V is independently fluorine, chlorine, bromine, iodine, cyano, nitro, methyl, ethyl, propyl, butyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-di-$C_1$-$C_4$-alkylamino (e.g. N,N-dimethylamino).

A further preferred embodiment relates to inventive compounds as described above in the summary, in which the compound is a compound of the formula (Ic-1)

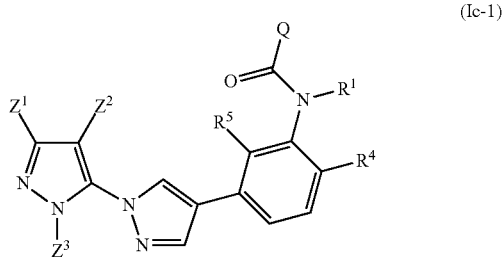
(Ic-1)

A further preferred embodiment relates to inventive compounds as described above in the summary, in which the compound is a compound of the formula (Ic-2)

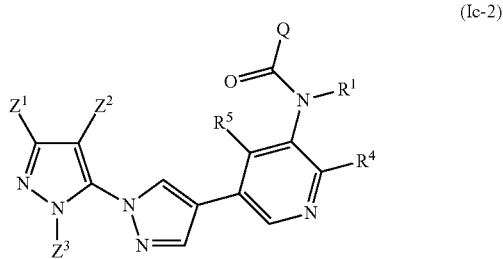
(Ic-2)

The invention also provides for the use of the inventive compounds (for example of the formula (Ic), (Ic-1) or (Ic-2)) for control of insects, arachnids and nematodes; pharmaceutical compositions comprising at least one inventive compound; an inventive compound for use as a medicament; for the use of an inventive compound for production of pharmaceutical compositions for control of parasites in animals; a process for producing crop protection compositions comprising at least one inventive compound and customary extenders and/or surfactants; a method for controlling pests, characterized in that an inventive compound is allowed to act on the pests and/or their habitat; the use of an inventive compound for protection of the propagation material of plants.

DETAILED DESCRIPTION

The inventive pyrazolylheteroarylamides are defined by the general formula (I)

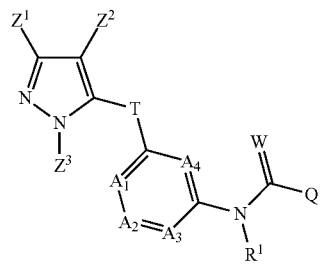
(I)

in which
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, most preferably hydrogen;
the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;
$R^2$, $R^3$, $R^4$ and $R^5$ are each independently hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;
if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
if neither of the $A_1$ and $A_2$ moieties is nitrogen, $R^2$ and $R^3$ together with the carbon atom to which they are bonded may form a 5- or 6-membered ring containing 0, 1 or 2 nitrogen atoms and/or 0 or 1 oxygen atom and/or 0 or 1 sulphur atom;
W is oxygen or sulphur;
Q is hydrogen, amino or one of the following optionally substituted moieties: alkyl, alkyloxy, alkenyl, alkynyl, cycloalkyl, heterocyclyl, cycloalkylalkyl, arylalkyl, heteroarylalkyl, alkoxycarbonyl, or an N-alkylamino, N-alkylcarbonylamino, N,N-dialkylamino, alkylsulphonylamino moiety; or
Q is an optionally mono- to penta-V-substituted aryl, or an optionally mono- to penta-V-substituted heteroaryl, where
V is halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino;
T is one of the 5-membered heteroaromatic systems T1-T10 shown below, where the bond to the pyrazolyl head group is indicated by an asterisk,

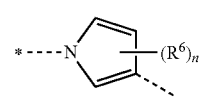
T1

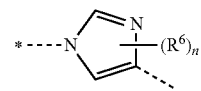
T2

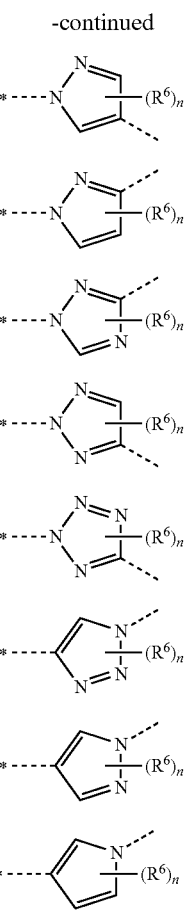

where
R⁶ is independently halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n has the values of 0-2;

$Z^1$ is an optionally substituted alkyl or cycloalkyl, and $Z^2$ is hydrogen, halogen, cyano, nitro, amino or an optionally substituted alkyl, alkylcarbonyl, alkylsulphanyl, alkylsulphinyl, alkylsulphonyl, and $Z^3$ is hydrogen or an optionally substituted alkyl, cycloalkyl, alkenyl, alkynyl, aryl or hetaryl.

Preference is given to compounds of the formula (I)

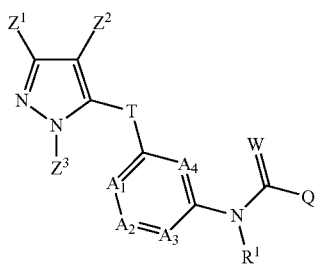

(I)

in which
R¹ is hydrogen or an optionally independently with halogen, cyano, alkoxy or alkoxycarbonyl mono- to hepta-substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, most preferably hydrogen;

the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;

$R^2$, $R^3$, $R^4$ and $R^5$ are each independently hydrogen, halogen, cyano, nitro, or optionally independently with halogen, cyano, alkoxy or alkoxycarbonyl mono- to hepta-substituted $C_1$-$C_6$-alkyl, $C_3$-$C_6$-cycloalkyl, $C_1$-$C_6$-alkoxy, N-alkoxyiminoalkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino;

if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or if neither of the $A_1$ and $A_2$ moieties is nitrogen, $R^2$ and $R^3$ together with the carbon atom to which they are bonded may form a 6-membered ring containing 0, 1 or 2 nitrogen atoms;

W is oxygen or sulphur;

Q is hydrogen, amino or optionally independently with halogen, cyano, $C_1$-$C_6$-alkoxy or $C_1$-$C_6$-alkoxycarbonyl mono- to hepta-substituted $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-aryl-($C_1$-$C_3$)-alkyl, 5- or 6-membered heteroaryl, 5- or 6-membered heteroaryl-($C_1$-$C_3$)-alkyl, $C_1$-$C_4$-alkoxycarbonyl moieties, or an N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino moiety; or Q is an aryl substituted by 0, 1, 2, 3 or 4 V substituents or a 5- or 6-membered heteroaryl substituted by 0, 1, 2, 3 or 4 V substituents, where V is independently halogen, cyano, nitro or optionally independently with halogen, cyano, alkoxy or alkoxycarbonyl mono- to hepta-substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T is one of the 5-membered heteroaromatic systems T1-T10 shown below, where the bond to the pyrazolyl head group is indicated by an asterisk,

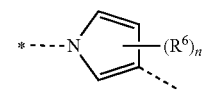
T1

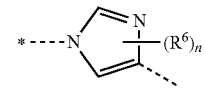
T2

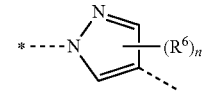
T3

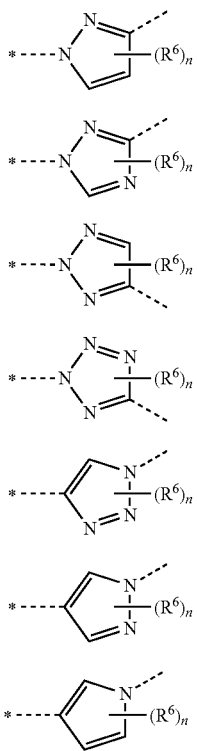

where
R⁶ is independently halogen, cyano, nitro, amino or an optionally mono- to hepta-halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n has the values of 0-1;

$Z^1$ is an optionally independently with halogen, cyano, alkoxy or alkoxycarbonyl mono- to hepta-substituted $C_1$-$C_6$-alkyl, $C_3$-$C_6$-cycloalkyl, and $Z^2$ is hydrogen, halogen, cyano, nitro, amino or an optionally independently with halogen, cyano, alkoxy or alkoxycarbonyl mono- to hepta-substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ is hydrogen or an optionally independently with halogen, cyano, alkoxy or alkoxycarbonyl mono- to hepta-substituted $C_1$-$C_6$-alkyl, $C_3$-$C_6$-cycloalkyl $C_3$-$C_6$-alkenyl, $C_3$-$C_6$-alkynyl, or is an optionally independently mono- to penta-halogen-, -cyano-, -alkoxy- and -alkoxycarbonyl-substituted aryl or hetaryl.

Preference is also given to compounds of the formula (I)

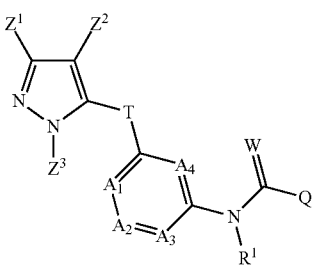

(I)

in which $R^1$ is hydrogen or an optionally independently with halogen, cyano, alkoxy or alkoxycarbonyl mono- to hepta-substituted $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, most preferably hydrogen;

the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;

$R^2$, $R^3$, $R^4$ and $R^5$ are each independently hydrogen, halogen, cyano, nitro, or optionally independently with halogen, cyano, alkoxy or alkoxycarbonyl mono- to hepta-substituted $C_1$-$C_6$-alkyl, $C_3$-$C_6$-cycloalkyl, $C_1$-$C_6$-alkoxy, N-alkoxyiminoalkyl, $C_1$-$C_6$-alkylsulphanyl, $C_1$-$C_6$-alkylsulphonyl, N,N-di-$C_1$-$C_6$-alkylamino;

if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or if neither of the $A_1$ and $A_2$ moieties is nitrogen, $R^2$ and $R^3$ together with the carbon atom to which they are bonded may form a 6-membered ring containing 0, 1 or 2 nitrogen atoms;

W is oxygen or sulphur;

Q is hydrogen, amino or optionally independently with halogen, cyano, alkoxy or alkoxycarbonyl mono- to hepta-substituted $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_3$-$C_6$-cycloalkyl-$C_1$-$C_6$-alkyl, aryl-($C_1$-$C_3$)-alkyl, heteroaryl-($C_1$-$C_3$)-alkyl, $C_1$-$C_4$-alkoxycarbonyl moieties, or is an N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino moieties; or Q is an optionally mono- to penta-V-substituted aryl, or an optionally mono- to penta-V-substituted heteroaryl, where V is independently halogen, cyano, nitro or optionally independently with halogen, cyano, alkoxy or alkoxycarbonyl mono- to hepta-substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

T is one of the 5-membered heteroaromatic systems T1-T10 shown below, where the bond to the pyrazolyl head group is indicated by an asterisk,

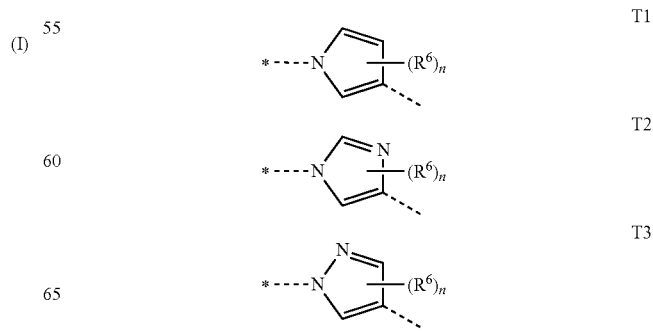

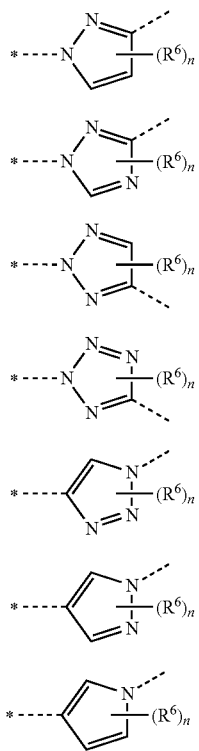

where
R[6] is independently halogen, cyano, nitro, amino or an optionally mono- to hepta-halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n has the values of 0-1;

Z[1] is an optionally substituted $C_1$-$C_6$-haloalkyl, $C_3$-$C_6$-cycloalkyl, $C_3$-$C_6$-halocycloalkyl, and Z[2] is hydrogen, halogen, cyano, nitro, amino or an independently with halogen, cyano, alkoxy or alkoxycarbonyl mono- to hepta-substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and Z[3] is hydrogen or an optionally independently with halogen, cyano, alkoxy and alkoxycarbonyl mono- to hepta-substituted $C_1$-$C_6$-alkyl, $C_3$-$C_6$-cycloalkyl, $C_3$-$C_6$-alkenyl, $C_3$-$C_6$-alkynyl, or is an optionally independently mono- to penta-halogen-, -cyano-, -alkoxy- and -alkoxycarbonyl-substituted aryl or hetaryl.

Particular preference is given to compounds of the formula (I)

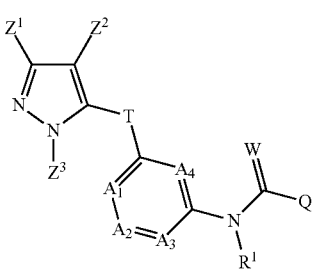

(I)

in which
R[1] is hydrogen, methyl, ethyl, n-propyl, isopropyl, n-butyl, isobutyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-yl-methyl, 4-chloropyrid-3-yl-methyl, most preferably hydrogen;

the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;

R[2] and R[5] are each independently hydrogen, fluorine, chlorine, bromine, iodine, methyl and methoxy and R[3] and R[4] are each independently hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl;

W is oxygen or sulphur;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, methylsulphonylamino; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

T is one of the 5-membered heteroaromatic systems T1-T10 shown below, where the bond to the pyrazolyl head group is indicated by an asterisk,

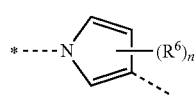
T1

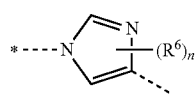
T2

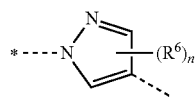
T3

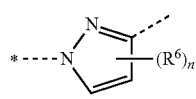
T4

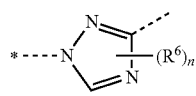
T5

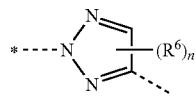
T6

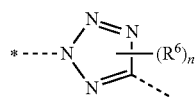
T7

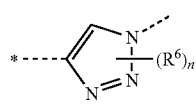
T8

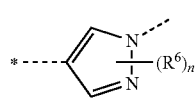
T9

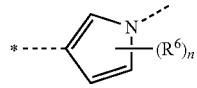
T10 where $R^6$ is independently halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and n has the values of 0-1;

$Z^1$ is methyl, ethyl, 1,1-dimethylethyl, difluoromethyl, chlorodifluoromethyl, dichlorofluoromethyl, trifluoromethyl, bromodichlormethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanpcyclopropyl, 1-trifluoromethylcyclopropyl, cyclobutyl and 2,2-difluoro-1-methylcyclopropyl, and $Z^2$ is hydrogen, halogen, cyano, nitro, amino, methyl, ethyl, 1,1-dimethylethyl, difluoromethyl, chlorodifluoromethyl, dichlorofluoromethyl, trifluoromethyl, bromodichlorometyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylsulphanyl, methylsulphinyl, methylsulphonyl, ethylthio, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and $Z^3$ is hydrogen, methyl, ethyl, n-propyl, isopropyl, n-butyl, isobutyl, s-butyl, t-butyl, ethenyl, 1-propenyl, 2-propenyl, 1-propynyl, 1-butynyl, difluoromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 2,4-dichlorophenyl, 3,4-dichlorophenyl, 2,6-dichlorophenyl, 2,6-dichloro-4-trifluoromethylphenyl, 3-chloro-5-trifluoromethylpyridin-2-yl.

Especially preferred are compounds of the general formula (I) in which $Z^1$ is trifluoromethyl, 1-chlorocyclopropyl, 1-fluorocyclopropyl or pentafluoroethyl;

$Z^2$ is trifluoromethyl, nitro, methylsulphanyl, methylsulphinyl, methylsulphonyl, fluorine, chlorine, bromine, cyano or iodine;

$Z^3$ is methyl, ethyl, n-propyl or hydrogen;

$R^1$ is hydrogen, methyl, ethyl, n-propyl, isopropyl, n-butyl, i-butyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-yl-methyl, 4-chloropyrid-3-yl-methyl;

$A_1$ and $A_2$ are each CH;

$A_3$ is $CR^4$ and $A_4$ is $CR^5$;

$R^4$ is hydrogen, fluorine, chlorine, bromine, iodine or cyano;

$R^5$ is hydrogen, fluorine, chlorine, bromine, iodine, methyl or methoxy;

T is one of the 5-membered heteroaromatic systems T1-T10 shown below, where the bond to the pyrazolyl head group is indicated by an asterisk,

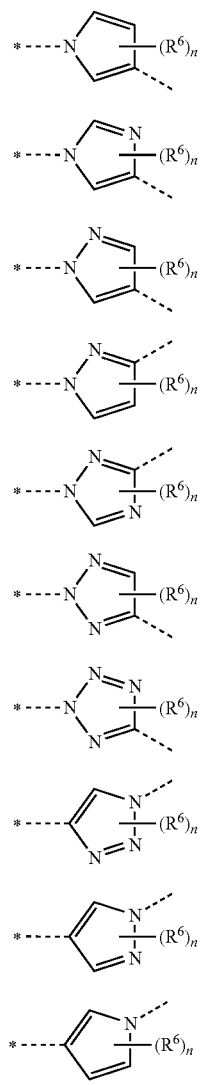

where $R^6$ is hydrogen (n=0), methyl, ethyl, 2-methylethyl, 2,2-dimethylethyl, fluorine, chlorine, bromine, iodine, nitro, trifluoromethyl, amino;

W is oxygen;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, methylsulphonylamino, most preferably hydrogen; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

Additionally especially preferred are compounds of the general formula (I) in which $Z^1$ is trifluoromethyl, 1-chlorocyclopropyl, 1-fluorocyclopropyl or pentafluoroethyl;

$Z^2$ is trifluoromethyl, nitro, methylsulphanyl, methylsulphinyl, methylsulphonyl, fluorine, chlorine, bromine, cyano or iodine;

$Z^3$ is methyl, ethyl, n-propyl or hydrogen;

$R^1$ is hydrogen, methyl, ethyl, n-propyl, isopropyl, n-butyl, i-butyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-yl-methyl, 4-chloropyrid-3-yl-methyl, most preferably hydrogen;

$A_1$ is CH;
$A_2$ is nitrogen;
$A_3$ is $CR^4$ and
$A_4$ is $CR^5$;

$R^4$ is hydrogen, fluorine, chlorine, bromine, iodine or cyano;

$R^5$ is hydrogen, fluorine, chlorine, bromine, iodine, methyl or methoxy;

T is one of the 5-membered heteroaromatic systems T1-T10 shown below, where the bond to the pyrazolyl head group is indicated by an asterisk,

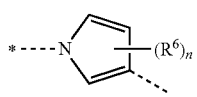
T1

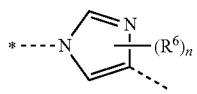
T2

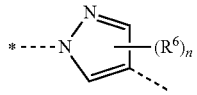
T3

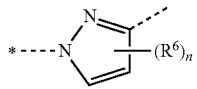
T4

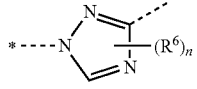
T5

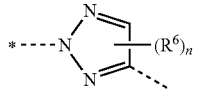
T6

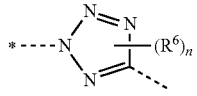
T7

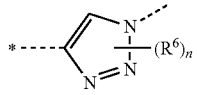
T8

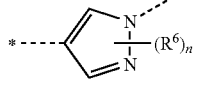
T9

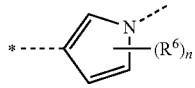
T10 where $R^6$ is hydrogen (n=0), methyl, ethyl, 2-methylethyl, 2,2-dimethylethyl, fluorine, chlorine, bromine, iodine, nitro, trifluoromethyl, amino;

W is oxygen;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino, methylsulphonylamino; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

Also especially preferred are the compounds that are each defined by one of the general formulae (Ia), (Ib), (Ic), (Id), (Ie), (If), (Ig), (Ih), (Ii) and (Ij), in which the $A_1$-$A_4$, n, W, Q, $R^1$ and $Z^1$-$Z^3$ radicals are each as defined above.

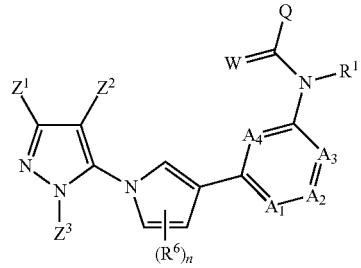
(Ia)

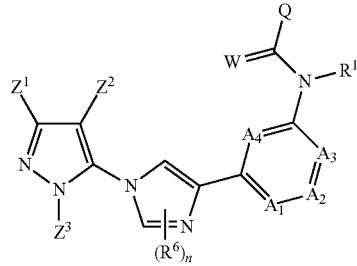
(Ib)

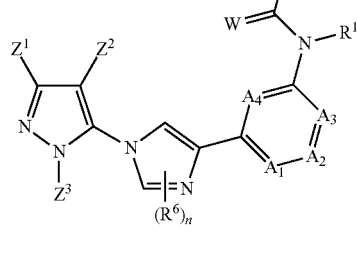
(Ic)

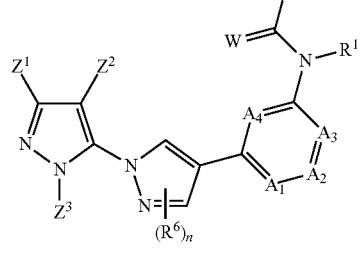
(Id)

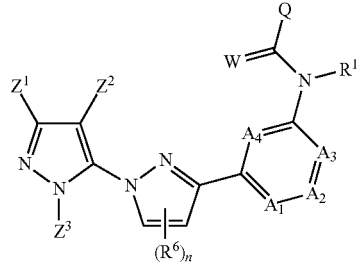
(Ie)

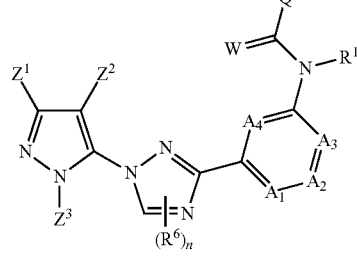

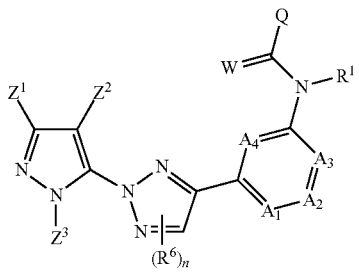
(If)

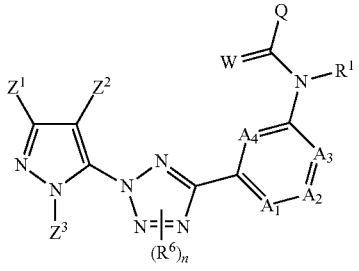
(Ig)

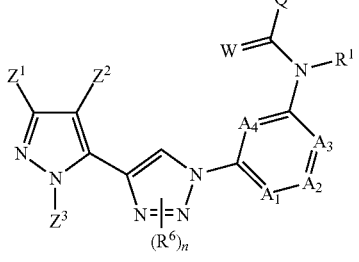
(Ih)

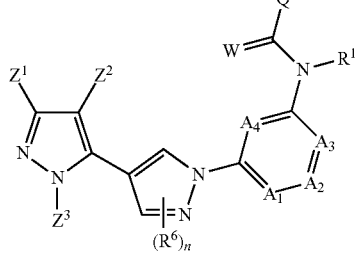
(Ii)

(Ij)

Very particular preference is given to compounds of the general formula (Ic) in which $Z^1$ is $CF_2CF_3$, $Z^2$ is $CF_3$, $Z^3$ is $CH_3$, the $R^1$, $R^6$ radicals are hydrogen (n=0), $A_1$, $A_2$ are C—H, $A_3$ is C—H, C—Cl, C—F, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

Very particular preference is given to compounds of the general formula (Ic) in which $Z^1$ is $CF_2CF_3$, $Z^2$ is $CF_3$, $Z^3$ is $CH_3$, the $R^1$, $R^6$ radicals are hydrogen (n=0), $A_1$ is CH, $A_2$ is N, $A_3$ is C—H, C—Cl, C—F, C—$CH_3$, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

Very particular preference is given to compounds of the general formula (Ih) in which $Z^1$ is $CF_2CF_3$, $Z^2$ is $CF_3$, $Z^3$ is $CH_3$, the $R^1$, $R^6$ radicals are hydrogen (n=0), $A_1$, $A_2$ are C—H, $A_3$ is C—H, C—Cl, C—F, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

Very particular preference is given to compounds of the general formula (Ih) in which $Z^1$ is $CF_2CF_3$, $Z^2$ is $CF_3$, $Z^3$ is $CH_3$, the R', $R^6$ radicals are hydrogen (n=0), $A_1$ is CH, $A_2$ is N, $A_3$ is C—H, C—Cl, C—F, C—$CH_3$, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

Definitions

According to the invention, "alkyl"—alone or as part of a chemical group—represents straight-chain or branched hydrocarbons, preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Also preferred are alkyls having 1 to 4 carbon atoms, such as inter alia methyl, ethyl, n-propyl, isopropyl, n-butyl, isobutyl, s-butyl or t-butyl. The inventive alkyls may be substituted by one or more identical or different radicals.

According to the invention, "alkenyl"—alone or as part of a chemical group—represents straight-chain or branched hydrocarbons, preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Also preferred are alkenyls having 2 to 4 carbon atoms, such as inter alia 2-propenyl, 2-butenyl or 1-methyl-2-propenyl. The inventive alkenyls may be substituted by one or more identical or different radicals.

According to the invention, "alkynyl"—alone or as part of a chemical group—represents straight-chain or branched hydrocarbons, preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Also preferred are alkynyls having 2 to 4 carbon atoms, such as inter alia ethynyl, 2-propynyl or 2-butynyl-2-propenyl. The inventive alkynyls may be substituted by one or more identical or different radicals.

According to the invention, "cycloalkyl"—alone or as part of a chemical group—represents mono-, bi- or tricyclic hydrocarbons, preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Also preferred are cycloalkyls having 3, 4, 5, 6 or 7 carbon atoms, such as inter alia cyclopropyl or cyclobutyl. The inventive cycloalkyls may be substituted by one or more identical or different radicals.

According to the invention, "alkylcycloalkyl" represents mono-, bi- or tricyclic alkylcycloalkyl, preferably having 4 to 10 or 4 to 7 carbon atoms, for example ethylcyclopropyl, isopropylcyclobutyl, 3-methylcyclopentyl and 4-methylcyclohexyl. Also preferred are alkylcycloalkyls having 4, 5 or 7 carbon atoms, such as inter alia ethylcyclopropyl or 4-methylcyclohexyl. The inventive alkylcycloalkyls may be substituted by one or more identical or different radicals.

According to the invention, "cycloalkylalkyl" represents mono-, bi- or tricyclic cycloalkylalkyl, preferably having 4 to 10 or 4 to 7 carbon atoms, for example cyclopropylmethyl, cyclobutylmethyl, cyclopentylmethyl, cyclohexylmethyl and cyclopentylethyl. Also preferred are cycloalkylalkyls having 4, 5 or 7 carbon atoms, such as inter alia cyclopropylmethyl or cyclobutylmethyl. The inventive cycloalkylalkyls may be substituted by one or more identical or different radicals.

According to the invention, "halogen" represents fluorine, chlorine, bromine or iodine, especially fluorine, chlorine or bromine.

The inventive halogen-substituted chemical groups, for example haloalkyl, halocycloalkyl, haloalkyloxy, haloalkylsulphanyl, haloalkylsulphinyl or haloalkylsulphonyl, are mono- or polysubstituted by halogen up to the maximum possible number of substituents. In the case of polysubstitution by halogen, the halogen atoms may be the same or different and may all be bonded to one carbon atom or to more than one carbon atom. In this context, halogen is especially fluorine, chlorine, bromine or iodine, preferably fluorine, chlorine or bromine and more preferably fluorine.

According to the invention, "halocycloalkyl" represents mono-, bi- or tricyclic halocycloalkyl, preferably having 3 to 10 carbon atoms, such as inter alia 1-fluorocyclopropyl, 2-fluorocyclopropyl or 1-fluorocyclobutyl. Also preferred is halocycloalkyl having 3, 5 or 7 carbon atoms. The inventive halocycloalkyls may be substituted by one or more identical or different radicals.

According to the invention, "haloalkyl", "haloalkenyl" or "haloalkynyl" represents halogen-substituted alkyls, alkenyls or alkynyls having preferably 1 to 9 identical or different halogen atoms, for example monohaloalkyl such as CH2CH2Cl, CH2CH2F, CHClCH3, CHFCH3, CH2Cl, CH2F; perhaloalkyl such as CCl3 or CF3 or CF2CF3; polyhaloalkyl such as CHF2, CH2F, CH2CHFCl, CHCl2, CF2CF2H, CH2CF3. The same applies to haloalkenyl and halogen-substituted radicals. Haloalkoxy is, for example, OCF3, OCHF2, OCH2F, OCF2CF3, OCH2CF3 and OCH2CH2Cl.

Further examples of haloalkyls are chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and having 1 to 5 identical or different halogen atoms selected from fluorine and chlorine, such as inter alia difluoromethyl, trifluoromethyl or 2,2-difluoroethyl.

According to the invention, "hydroxyalkyl" represents straight-chain or branched alcohol, preferably having 1 to 6 carbon atoms, for example methanol, ethanol, n-propanol, isopropanol, n-butanol, isobutanol, s-butanol and t-butanol. Also preferably hydroxyalkyl groups having 1 to 4 carbon atoms. The inventive hydroxyalkyl groups may be substituted by one or more identical or different radicals.

According to the invention, "alkoxy" represents straight-chain or branched O-alkyl, preferably having 1 to 6 carbon atoms, for example methoxy, ethoxy, n-propoxy, isopropoxy, n-butoxy, isobutoxy, s-butoxy and t-butoxy. Also preferably alkoxy groups having 1 to 4 carbon atoms. The inventive alkoxy groups may be substituted by one or more identical or different radicals.

According to the invention, "haloalkoxy" represents halogen-substituted straight-chain or branched O-alkyl, preferably having 1 to 6 carbon atoms, such as inter alia difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy. Also preferably haloalkoxy groups having 1 to 4 carbon atoms. The inventive haloalkoxy groups may be substituted by one or more identical or different radicals.

According to the invention, "alkylsulphanyl" represents straight-chain or branched S-alkyl, preferably having 1 to 6 carbon atoms, for example methylthio, ethylthio, n-propylthio, isopropylthio, n-butylthio, isobutylthio, s-butylthio and t-butylthio. Also preferably alkylsulphanyl groups having 1 to 4 carbon atoms. The inventive alkylsulphanyl groups may be substituted by one or more identical or different radicals.

Examples of haloalkylsulphanyl, i.e. halogen-substituted alkylsulphanyl groups, include difluoromethylthio, trifluoromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio.

According to the invention, "alkylsulphinyl" represents straight-chain or branched alkylsulphinyl, preferably having 1 to 6 carbon atoms, for example methylsulphinyl, ethylsulphinyl, n-propylsulphinyl, isopropylsulphinyl, n-butylsulphinyl, isobutylsulphinyl, s-butylsulphinyl and t-butylsulphinyl. Also preferably alkylsulphinyl groups having 1 to 4 carbon atoms. The inventive alkylsulphinyl groups may be substituted by one or more identical or different radicals.

Examples of haloalkylsulphinyl groups, i.e. halogen-substituted alkylsulphinyl groups, include difluoromethylsulphinyl, trifluoromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, "alkylsulphonyl" represents straight-chain or branched alkylsulphonyl, preferably having 1 to 6 carbon atoms, for example methylsulphonyl, ethylsulphonyl, n-propylsulphonyl, isopropylsulphonyl, n-butylsulphonyl, isobutylsulphonyl, s-butylsulphonyl and t-butylsulphonyl. Also preferably alkylsulphonyl groups having 1 to 4 carbon atoms. The inventive alkylsulphonyl groups may be substituted by one or more identical or different radicals.

Examples of haloalkylsulphonyl groups, i.e. halogen-substituted alkylsulphonyl groups, include difluoromethylsulphonyl, trifluoromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, "alkylcarbonyl" represents straight-chain or branched alkyl-C(=O), preferably having 2 to 7 carbon atoms, such as methylcarbonyl, ethylcarbonyl, n-propylcarbonyl, isopropylcarbonyl, s-butylcarbonyl and t-butylcarbonyl. Also preferably alkylcarbonyls having 1 to 4 carbon atoms. The inventive alkylcarbonyls may be substituted by one or more identical or different radicals.

According to the invention, "cycloalkylcarbonyl" represents straight-chain or branched cycloalkylcarbonyl, preferably having 3 to 10 carbon atoms in the cycloalkyl moiety, for example cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Also preferably cycloalkylcarbonyl having 3, 5 or 7 carbon atoms in the cycloalkyl moiety. The inventive cycloalkylcarbonyl groups may be substituted by one or more identical or different radicals.

According to the invention, "alkoxycarbonyl"—alone or as part of a chemical group—represents straight-chain or branched alkoxycarbonyl, preferably having 1 to 6 carbon atoms or 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The inventive alkoxycarbonyl groups may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The inventive alkylaminocarbonyl groups may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, for example N,N-dimethylaminocarbonyl, N,N-diethylaminocarbonyl, N,N-di(n-propylamino)carbonyl, N,N-di(isopropylamino)carbonyl and N,N-di(s-butylamino)carbonyl. The inventive N,N-dialkylaminocarbonyl groups may be substituted by one or more identical or different radicals.

According to the invention, "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. Likewise encompassed are bicyclic carbon cycles (only carbon as ring atoms), in which one ring is an aryl and the second ring is not an aryl, for example tetralinyl ($C_{10}H_{11}$), where the bonding site may be on the aromatic or nonaromatic ring. The inventive aryl groups may be substituted by one or more identical or different radicals.

Examples of substituted aryls are the arylalkyls, which may likewise be substituted by one or more identical or different radicals and the alkyl and/or aryl moiety. Examples of such arylalkyls include benzyl and 1-phenylethyl.

According to the invention, "heterocycle", "heterocyclic ring" or "heterocyclic ring system" (heterocyclyl) represents a carbocyclic ring system having at least one ring in which at least one carbon atom has been replaced by a heteroatom, preferably by a heteroatom from the group of N, O, S, P, B, Si, Se, and which is saturated or partly unsaturated and may at the same time be unsubstituted or substituted by a further substituent, where the bonding site is localized on a ring atom. Unless defined otherwise, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group of N, O and S, although no two oxygen atoms should be directly adjacent. The heterocyclic rings usually contain not more than 4 nitrogen atoms and/or not more than 2 oxygen atoms and/or not more than 2 sulphur atoms. If the heterocyclyl radical or the heterocyclic ring is optionally substituted, it may be fused to other carbocyclic or heterocyclic rings. In the case of optionally substituted heterocyclyl, the invention also encompasses optionally substituted polycyclic, preferably bicyclic, heterocycles, for example 8-azabicyclo[3.2.1]octanyl or 1-azabicyclo[2.2.1]heptyl, benzothiophenyl, e.g. benzothiophen-2-yl, benzofuranyl, e.g. benzofuran-2-yl, [1,2,4]triazolo[1,5-a]pyrimidinyl, e.g. [1,2,4]triazolo[1,5-a]pyrimidin-2-yl, 1,3-benzodioxolyl, e.g. 1,3-benzodioxol-5-yl. In the case of optionally substituted heterocyclyl, the invention also encompasses spirocyclic systems, for example 1-oxa-5-azaspiro[2.3]hexyl.

Inventive heterocyclyl groups are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the expression "heteroaryl" represents heteroaromatic compounds, i.e. fully unsaturated aromatic heterocyclic compounds covered by the above definition of heterocycles. Preferably 5- to 7-membered rings having 1 to 3, preferably 1 or 2, identical or different heteroatoms from the abovementioned group. Inventive heteroaryls are, for example, furanyl, thiophenyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals.

Substituted groups, such as a substituted alkyl, alkenyl, alkynyl, cycloalkyl, aryl, phenyl, benzyl, heterocyclyl and heteroaryl radical, mean, for example, a substituted radical derived from the unsubstituted base structure, where the substituents are, for example, one or more, preferably 1, 2 or 3, radicals from the group of halogen, oxo (O=), alkoxy, alkylsulphanyl, hydroxyl, amino, nitro, carboxyl or a group equivalent to the carboxyl group, cyano, isocyano, azido, alkoxycarbonyl, alkylcarbonyl, formyl, carbamoyl, mono- and N,N-dialkylaminocarbonyl, substituted amino such as acylamino, mono- and N,N-dialkylamino, trialkylsilyl and optionally substituted cycloalkyl, optionally substituted aryl, optionally substituted heterocyclyl, where each of the latter cyclic groups may also be bonded by heteroatoms or divalent functional groups as in the case of the alkyl radicals mentioned, and alkylsulphinyl, including both enantiomers of the alkylsulphinyl group, alkylsulphonyl, alkylphosphinyl, alkylphosphonyl and, in the case of cyclic radicals (="cyclic base structures"), also alkyl, haloalkyl, alkylsulphanylalkyl, alkoxyalkyl, optionally substituted mono- and N,N-dialkylaminoalkyl and hydroxyalkyl.

The term "substituted groups" such as substituted alkyl, cycloalkyl, aryl, heteroaryl, etc. includes, as substituents, in addition to the saturated hydrocarbonaceous radicals mentioned, corresponding unsaturated aliphatic and aromatic radicals, such as in each case optionally substituted alkenyl, alkynyl, oxo (O=), alkoxy, alkenyloxy, alkynyloxy, aryloxy (e.g. phenyloxy (phenyl-O—), benzyloxy ($C_6H_5$—$CH_2$—O—), alkylthio, alkenylthio, alkynylthio, arylthio (e.g. phenylthio (phenyl-S—)), alkenyloxycarbonyl, alkynyloxycarbonyl, alkenylcarbonyl, alkynylcarbonyl, mono- and N,N-dialkenylaminocarbonyl, mono- and dialkynylaminocarbonyl, mono- and N,N-dialkenylamino, mono- and N,N-dialkynylamino, trialkenylsilyl, trialkynylsilyl, cycloalkyl, cycloalkenyl, cycloalkynyl, heteroaryl, aryl such as phenyl, phenoxy, etc. In the case of substituted cyclic radicals having aliphatic components in the ring, also included are cyclic systems having such substituents that are bonded to the ring by a single bond, of a double bond on the ring, for example by an alkylidene group such as methylidene or ethylidene, or an oxo group, imino group or else a substituted imino group, or else cyclic systems having such substituents in which a second ring is bonded to two different atoms of the cyclic radical by two different atoms, for example naphthyl or tetrahydronaphthalenyl (e.g. 1,2,3, 4-tetrahydronaphthalen-1-yl).

If two or more radicals form one or more rings, these may be carbocyclic, heterocyclic, saturated, partially saturated, unsaturated, for example also aromatic and further-substituted.

The substituents mentioned by way of example ("first substituent level") may, if they contain hydrocarboneous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example,
amino, hydroxy, halogen, nitro, cyano, isocyano, mercapto, isothiocyanato, carboxy, carbonamid, SF5, aminosulphonyl, alkyl, cycloalkyl, alkenyl, cycloalkenyl, alkynyl, N-monoalkylamino, N,N-dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylsulphanyl, cycloalkylsulphanyl, alkenylthio, cycloalkenylthio, alkynylthio, alkylsulphenyl and alkylsulphinyl, including both enantiomers of the alkylsulphinyl group, alkylsulphonyl, N-monoalkylaminosulphonyl, N,N-dialkylaminosulphonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of more than one substituent level are preferably alkoxyalkyl, alkylsulphanylalkyl, alkylsulphanylalkoxy, alkoxyalkoxy, phenethyl, benzyloxy, haloalkyl, halocycloalkyl, haloalkoxy, haloalkylsulphanyl, haloalkylsulphinyl, haloalkylsulphonyl, haloalkanoyl, haloalkylcarbonyl, haloalkoxycarbonyl, haloalkoxyalkoxy, haloalkoxyalkylsulphanyl, haloalkoxyalkanoyl, haloalkoxyalkyl.

In the case of radicals having carbon atoms, preference is given to those having 1 to 6 carbon atoms, preferably 1 to 4 carbon atoms, particularly 1 or 2 carbon atoms. Preference is generally given to substituents from the group of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given to the substituents methyl, methoxy, fluorine and chlorine.

Substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably N-mono- and N,N-dialkylamino (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; acyl is as defined further down, preferably $(C_1-C_4)$alkanoyl. The same applies to substituted hydroxylamino or hydrazino.

According to the invention, the term "cyclic amino groups" encompasses heteroaromatic or aliphatic ring systems having one or more nitrogen atoms. The heterocycles are saturated or unsaturated, consist of one or more optionally fused ring systems and optionally include further heteroatoms, for example one or two nitrogen, oxygen and/or sulphur atoms. In addition, the term also encompasses those groups which have a spiro ring or bridged ring system. The number of atoms that form the cyclic amino group is unlimited and the group may consist, in the case of a one-ring system, for example, of 3 to 8 ring atoms and, in the case of a two-ring system, of 7 to 11 atoms.

Examples of cyclic amino groups having saturated and unsaturated monocyclic groups having a nitrogen atom as heteroatom include 1-azetidinyl, pyrrolidino, 2-pyrrolin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, for example oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulphur atoms as heteroatoms include thiazolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl, perhydropyrrolo[1,2-a]pyrazin-2-yl; examples of cyclic amino groups having spirocyclic groups include are 2-azaspiro[4.5]decan-2-yl; examples of cyclic amino groups having bridged heterocyclic groups include 2-azabicyclo[2.2.1]heptan-7-yl.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, $(C_1-C_4)$alkylsulphanyl, $(C_1-C_4)$haloalkylsulphanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethylphenyl, 2,4-, 3,5-, 2,5- and 2,3-dichlorophenyl, o-, m- and p-methoxyphenyl.

Optionally substituted cycloalkyl is preferably cycloalkyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl and $(C_1-C_4)$haloalkoxy, especially by one or two $(C_1-C_4)$alkyl radicals.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, nitro and oxo, especially mono- or polysubstituted by radicals from the group of halogen, $(C_1-C_4)$alkyl, $(C_1-C_4)$alkoxy, $(C_1-C_4)$haloalkyl and oxo, very particularly substituted by one or two $(C_1-C_4)$alkyl radicals.

Examples of alkyl-substituted heteroaryls are furanylmethyl, thiophenylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridinylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Salts of the inventive compounds that are suitable in accordance with the invention, for example salts with bases or acid addition salts, are all customary non-toxic salts, preferably agriculturally and/or physiologically acceptable salts. For example salts with bases or acid addition salts. Preference is given to salts with inorganic bases, for example alkali metal salts (e.g. sodium, potassium or caesium salts), alkaline earth metal salts (e.g. calcium or magnesium salts), ammonium salts or salts with organic bases, especially with organic amines, for example triethylammonium, dicyclohexylammonium, N,N'-dibenzylethylenediammonium, pyridinium, picolinium or ethanolammonium salts, salts with inorganic acids (e.g. hydrochlorides, hydrobromides, dihydrosulphates, trihydrosulphates, or phosphates), salts with organic carboxylic acids or organic sulphonic acids (e.g. formates, acetates, trifluoroacetates, maleates, tartrates, methanesulphonates, benzenesulphonates or 4-toluenesulphonates). As is well known, t-amines, for example some of the inventive compounds, can form N-oxides, which are likewise inventive salts.

The inventive compounds may, depending on the nature of the substituents, be in the form of geometric and/or optically active isomers or corresponding isomer mixtures of varying composition. These stereoisomers are, for example, enantiomers, diastereomers, atropisomers or geometric isomers. The invention therefore encompasses pure stereoisomers and any desired mixtures of these isomers.

The inventive compounds may possibly be present in different polymorphic forms or as a mixture of different polymorphic forms. Both the pure polymorphs and the polymorph mixtures are provided by the invention and can be used in accordance with the invention.

One aspect 1 relates to compounds of the general formula (I)

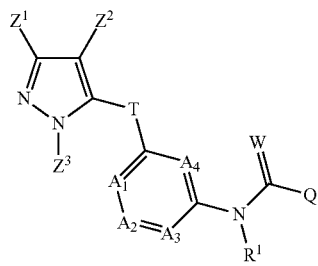

(I)

in which
$R^1$ is hydrogen, optionally substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl-($C_1$-$C_3$)-alkyl, heteroaryl-($C_1$-$C_3$)-alkyl, most preferably hydrogen;
the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;

$R^2$, $R^3$, $R^4$ and $R^5$ are each independently hydrogen, halogen, cyano, nitro, optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;
if neither of the $A_2$ and $A_3$ moieties is nitrogen, $R^3$ and $R^4$ together with the carbon atom to which they are bonded may form a 5- or 6-membered ring containing 0, 1 or 2 nitrogen atoms and/or 0 or 1 oxygen atom and/or 0 or 1 sulphur atom, or
if neither of the $A_1$ and $A_2$ moieties is nitrogen, $R^2$ and $R^3$ together with the carbon atom to which they are bonded may form a 5- or 6-membered ring containing 0, 1 or 2 nitrogen atoms and/or 0 or 1 oxygen atom and/or 0 or 1 sulphur atom;
W is oxygen or sulphur;
Q is hydrogen, amino or one of the following optionally substituted moieties: alkyl, alkyloxy, alkenyl, alkynyl, cycloalkyl, heterocyclyl, cycloalkylalkyl, arylalkyl, heteroarylalkyl, alkoxycarbonyl, or an N-alkylamino, N-alkylcarbonylamino, N,N-dialkylamino, alkylsulphonylamino moiety; or
Q is an optionally mono- to penta-V-substituted aryl, or an optionally mono- to penta-V-substituted heteroaryl, where
V is halogen, cyano, nitro, optionally substituted alkyl, alkenyl, alkynyl, cycloalkyl, alkoxy, N-alkoxyiminoalkyl, alkylsulphanyl, alkylsulphinyl, alkylsulphonyl, N,N-dialkylamino;
T is one of the 5-membered heteroaromatic systems T1-T10 shown below, where the bond to the pyrazolyl head group is indicated by an asterisk,

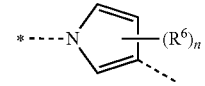

T1

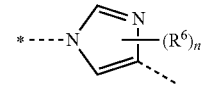

T2

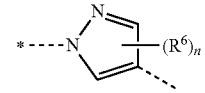

T3

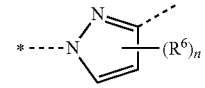

T4

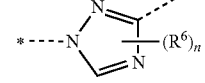

T5

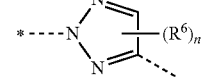

T6

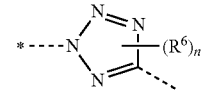

T7

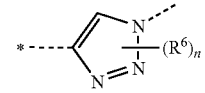

T8

-continued

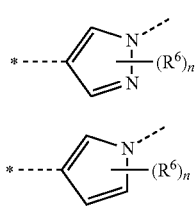

where
R⁶ is independently halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n has the values of 0-2;
$Z^1$ is an optionally substituted alkyl or cycloalkyl, and
$Z^2$ is hydrogen, halogen, cyano, nitro, amino or an optionally substituted alkyl, alkylcarbonyl, alkylsulphanyl, alkylsulphinyl, alkylsulphonyl, and
$Z^3$ is hydrogen or an optionally substituted alkyl, cycloalkyl, alkenyl, alkynyl, aryl or hetaryl.

One aspect 2 relates to compounds according to aspect 1, in which
$R^1$ is hydrogen or an optionally independently with halogen, cyano, alkoxy and alkoxycarbonyl mono- to hepta-substituted $C_1$-$C_6$-alkyl, $C_3$-$C_6$-alkenyl, $C_3$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, most preferably hydrogen;
the following chemical moieties are as follows:
$A_1$ is $CR^2$ or nitrogen,
$A_2$ is $CR^3$ or nitrogen,
$A_3$ is $CR^4$ or nitrogen, and
$A_4$ is $CR^5$ or nitrogen,
but not more than three of the chemical moieties $A_1$ to $A_4$ are simultaneously nitrogen;
$R^2$, $R^3$, $R^4$ and $R^5$ are each independently hydrogen, halogen, cyano, nitro, or an optionally independently with halogen, cyano, alkoxy and alkoxycarbonyl mono- to hepta-substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;
W is oxygen or sulphur;
Q is hydrogen, amino or one of the following independently with hydroxy, nitro, amino, halogen, alkoxy, cyano, hydroxycarbonyl, alkoxycarbonyl, alkylcarbamoyl, cycloalkylcarbamoyl, phenyl mono- to hepta-substituted moieties: $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_1$-$C_6$-hydroxyalkyl, aryl($C_1$-$C_3$)-alkyl, heteroaryl($C_1$-$C_3$)-alkyl, $C_1$-$C_4$-alkoxycarbonyl, N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino; or
Q is an aryl substituted by 0, 1, 2, 3 or 4 V substituents or a 5- or 6-membered heteroaryl substituted by 0, 1, 2, 3 or 4 V substituents, where
V is independently halogen, cyano, nitro or an optionally independently with halogen, cyano, alkoxy or alkoxycarbonyl mono- to hepta-substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;
T is one of the 5-membered heteroaromatic systems T1-T10 shown below, where the bond to the pyrazolyl head group is indicated by an asterisk,

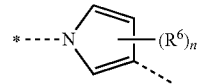

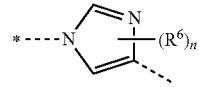

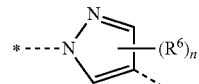

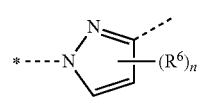

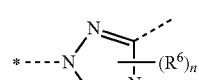

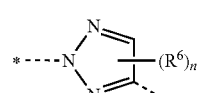

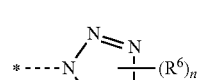

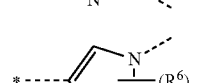

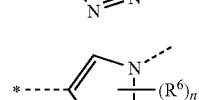

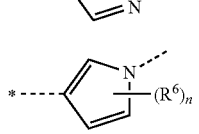

where
R⁶ is independently halogen, cyano, nitro, amino or an optionally mono- to hepta-halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n has the values of 0-1;
$Z^1$ is an optionally independently with halogen, cyano, alkoxy and alkoxycarbonyl mono- to hepta substituted $C_1$-$C_6$-alkyl, $C_3$-$C_6$-cycloalkyl, and
$Z^2$ is hydrogen, halogen, cyano, nitro, amino or an independently mono- to hepta-halogen-, -cyano-, -alkoxy- or -alkoxycarbonyl-substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
$Z^3$ is hydrogen or an optionally independently with -halogen, cyano, alkoxy and alkoxycarbonyl mono- to hepta-substituted C₁-C₆-alkyl, C₃-C₆-cycloalkyl, C₃-C₄-alkenyl, C₃-C₄-alkynyl, or an optionally independently with halogen, cyano, alkoxy and alkoxycarbonyl mono- to penta-substituted aryl or hetaryl.

One aspect 3 relates to compounds according to aspect 1 or 2, in which

R¹ is hydrogen, methyl, ethyl, n-propyl, isopropyl, n-butyl, isobutyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3ylmethyl, most preferably hydrogen;

the following chemical moieties are as follows:
A₁ is CR² or nitrogen,
A₂ is CR³ or nitrogen,
A₃ is CR⁴ or nitrogen, and
A₄ is CR⁵ or nitrogen,
but not more than three of the chemical moieties A₁ to A₄ are simultaneously nitrogen;

R² and R⁵ are each independently hydrogen, fluorine, chlorine, bromine, iodine, methyl and methoxy and R³ and R⁴ are each independently hydrogen, fluorine, chlorine, bromine, iodine, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl;

W is oxygen or sulphur;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH₂, N-ethylamino, N-allylamino, N,N-dimethylamino, N,N-diethylamino, methylsulphonylamino; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino;

T is one of the 5-membered heteroaromatic systems T1-T10 shown below, where the bond to the pyrazolyl head group is indicated by an asterisk,

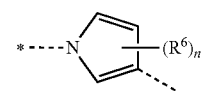

T1

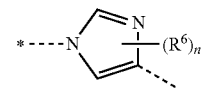

T2

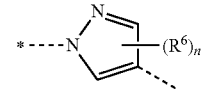

T3

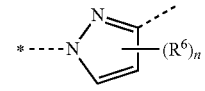

T4

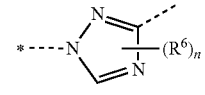

T5

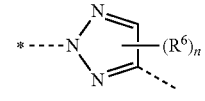

T6

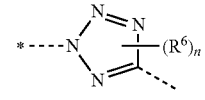

T7

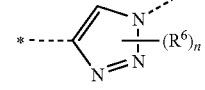

T8

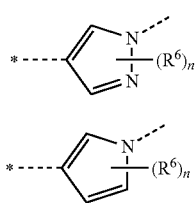

where

R⁶ is independently halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl, trifluoromethylsulphinyl, and n has the values of 0-1;

Z¹ is methyl, ethyl, 1,1-dimethylethyl, difluoromethyl, chlorodifluoromethyl, dichlorofluoromethyl, trifluoromethyl, bromodichlormethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, cyclopropyl, 1-chlorocyclopropyl, 1-fluorocyclopropyl, 1-bromocyclopropyl, 1-cyanocyclopropyl, 1-trifluoromethylcyclopropyl, cyclobutyl and 2,2-difluoro-1-methylcyclopropyl, and Z² is hydrogen, halogen, cyano, nitro, amino, methyl, ethyl, 1,1-dimethylethyl, difluoromethyl, chlorodifluoromethyl, dichlorofluoromethyl, trifluoromethyl, bromodichloromethyl, chloromethyl, bromomethyl, 1-fluoroethyl, 1-fluoro-1-methylethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-t-butyl, heptafluoro-n-propyl, heptafluoroisopropyl, nonafluoro-n-butyl, methylsulphanyl, methylsulphinyl, methylsulphonyl, ethylthio, ethylsulphinyl, ethylsulphonyl, trifluoromethylsulphanyl, trifluoromethylsulphinyl, trifluoromethylsulphonyl, chlorodifluoromethylsulphanyl, chlorodifluoromethylsulphinyl, chlorodifluoromethylsulphonyl, dichlorofluoromethylsulphanyl, dichlorofluoromethylsulphinyl, dichlorofluoromethylsulphonyl and Z³ is hydrogen, methyl, ethyl, n-propyl, isopropyl, n-butyl, isobutyl, s-butyl, t-butyl, ethenyl, 1-propenyl, 2-propenyl, 1-propynyl, 1-butynyl, difluoromethyl, chlorodifluoromethyl, dichlorofluoromethyl, trifluoromethyl, chloromethyl, bromomethyl, 1-fluoroethyl, 1-fluoro-1-methylethyl, 2-fluoroethyl, 2,2-difluoroethyl, 2,2,2-trifluoroethyl, phenyl, 2-chlorophenyl, 3-chlorophenyl, 4-chlorophenyl, 2,5-dichlorophenyl, 2,4-dichlorophenyl, 3-4-dichlorophenyl, 2,6-dichlorophenyl, 2-6-dichloro-4-trifluoromethylphenyl, 3-chloro-5-trifluoromethylpyridin-2-yl.

One aspect 4 relates to compounds according to any of aspects 1 to 3, in which

Z¹ is trifluoromethyl, 1-chlorocyclopropyl, 1-fluorocyclopropyl or pentafluoroethyl;

Z² is trifluoromethyl, nitro, methylsulphanyl, methylsulphinyl, methylsulphonyl, fluorine, chlorine, bromine, cyano or iodine;

Z³ is methyl, ethyl, n-propyl or hydrogen;

R¹ is hydrogen, methyl, ethyl, n-propyl, isopropyl, n-butyl, i-butyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl, most preferably hydrogen;

A₁ and A₂ are each CH;

A₃ is CR⁴ and

A₄ is CR⁵;

R⁴ is hydrogen, fluorine, chlorine, bromine, iodine or cyano;

R⁵ is hydrogen, fluorine, chlorine, bromine, iodine, methyl or methoxy;

T is one of the 5-membered heteroaromatic systems T1-T10 shown below, where the bond to the pyrazolyl head group is indicated by an asterisk,

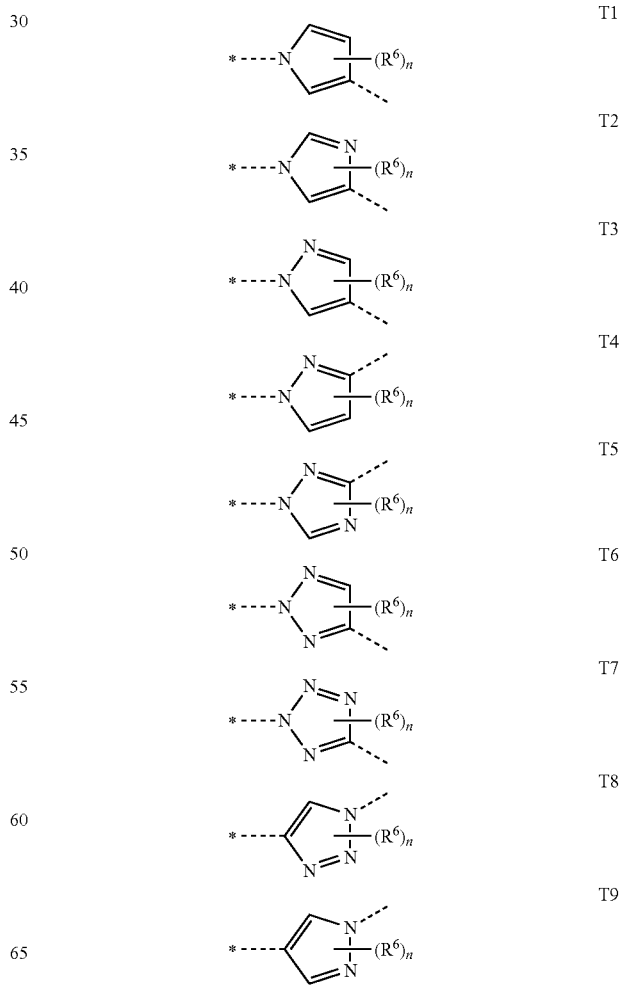

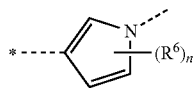
T10 where
R⁶ is hydrogen, methyl, ethyl, 2-methylethyl, 2,2-dimethylethyl, fluorine, chlorine, bromine, iodine, nitro, trifluoromethyl, amino;

W is oxygen;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl)cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, NH₂, N-ethylamino, N-allylamino, N,N-dimethylamino, N,N-diethylamino, methylsulphonylamino; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

One aspect 5 relates to compounds according to any of aspects 1 to 4, in which $Z^1$ is trifluoromethyl, 1-chlorocyclopropyl, 1-fluorocyclopropyl or pentafluoroethyl;

$Z^2$ is trifluoromethyl, nitro, methylsulphanyl, methylsulphinyl, methylsulphonyl, fluorine, chlorine, bromine, cyano or iodine;

$Z^3$ is methyl, ethyl, n-propyl or hydrogen;

$R^1$ is hydrogen, methyl, ethyl, n-propyl, isopropyl, n-butyl, i-butyl, s-butyl, t-butyl, prop-2-enyl, 2-methylprop-2-enyl, prop-2-ynyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl, most preferably hydrogen;

$A_1$ is CH;
$A_2$ is nitrogen;
$A_3$ is $CR^4$ and
$A_4$ is $CR^5$;

$R^4$ is hydrogen, fluorine, chlorine, bromine, iodine or cyano;
$R^5$ is hydrogen, fluorine, chlorine, bromine, iodine, methyl or methoxy;

T is one of the 5-membered heteroaromatic systems T1-T10 shown below, where the bond to the pyrazolyl head group is indicated by an asterisk,

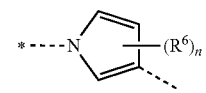
T1

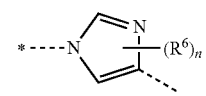
T2

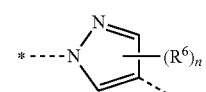
T3

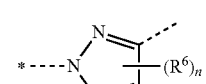
T4

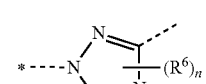
T5

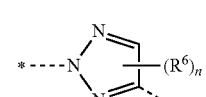
T6

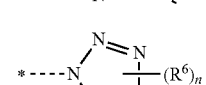
T7

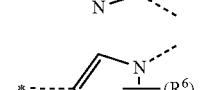
T8

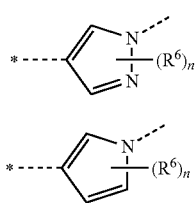

where
R⁶ is hydrogen, methyl, ethyl, 2-methylethyl, 2,2-dimethylethyl, fluorine, chlorine, bromine, iodine, nitro, trifluoromethyl, amino;

W is oxygen;

Q is hydrogen, methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1,1,2,2-tetrafluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-chlorocyclopropyl, 1-methylcyclopropyl, 1-methoxycarbonylcyclopropyl, 1-(N-methylcarbamoyl) cyclopropyl, 1-(N-cyclopropylcarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, oxetan-3-yl, thietan-3-yl, 1-oxidothietan-3-yl, 1,1-dioxidothietan-3-yl, isoxazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl) ethyl, 1-methyl-2-(ethylsulphanyl)ethyl, 2-methyl-1-(methylsulphanyl)propan-2-yl, methoxycarbonyl, methoxycarbonylmethyl, NH₂, N-ethylamino, N-allylamino, N,N-dimethylamino, N,N-diethylamino, methylsulphonylamino; or Q is one of the following groups substituted by 0, 1, 2, 3 or 4 V substituents: phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, where V is independently fluorine, chlorine, bromine, iodine, cyano, nitro, methyl, ethyl, difluoromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

One aspect 6 relates to compounds according to any of aspects 1 to 5, in which a compound of the general formula (I) is a compound of one of the formulae (Ia), (Ib), (Ic), (Id), (Ie), (If), (Ig), (Ih), (Ii) and (Ij)

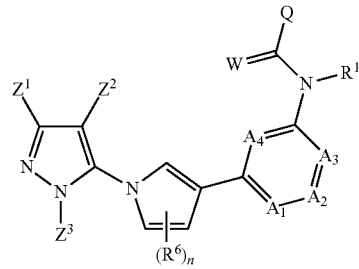

(Ia)

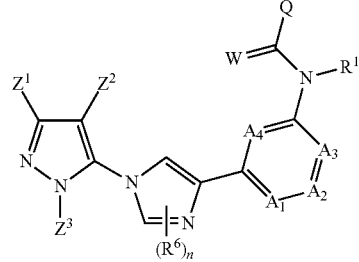

(Ib)

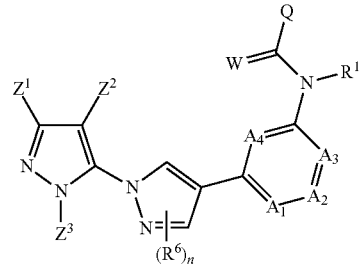

(Ic)

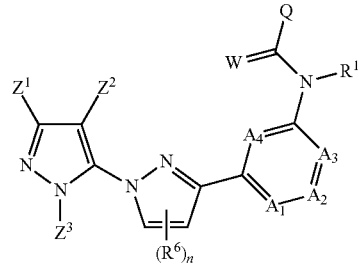

(Id)

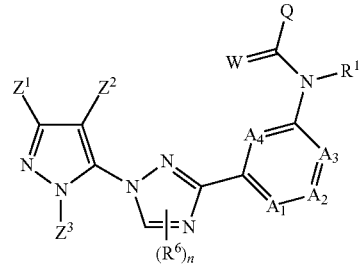

(Ie)

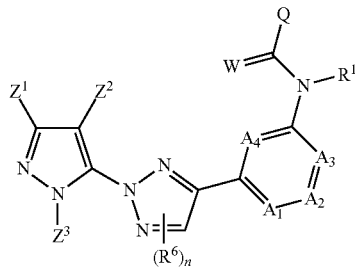 (If)

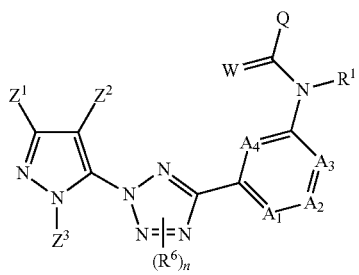 (Ig)

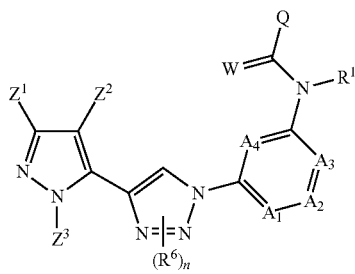 (Ih)

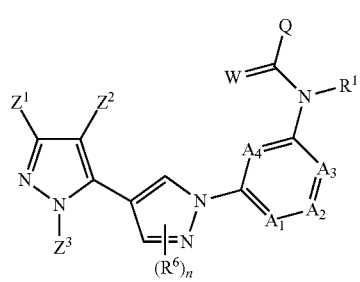 (Ii)

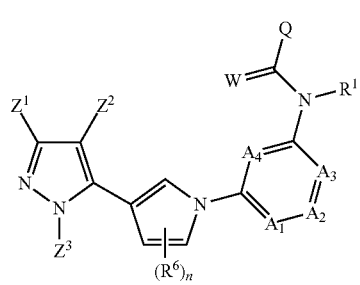 (Ij)

in which the $A_1$-$A_4$, n, W, Q, $R^1$ and $Z^1$-$Z^3$ radicals are each as defined according to any of aspects 1 to 6.

One aspect 7 relates to compounds according to any of aspects 1 to 7, in which a compound of the formula (I) is a compound of the general formulae (Ic)

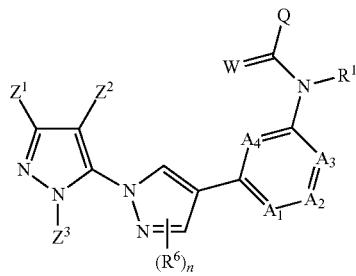 (Ic)

in which
$Z^1$ is $CF_2CF_3$,
$Z^2$ is $CF_3$,
$Z^3$ is $CH_3$,
the $R^1$, $R^6$ radicals are each hydrogen (n=0),
$A_1$, $A_2$ are C—H,
$A_3$ is C—H, C—Cl, C—F,
$A_4$ is C—H, C—F, C—OMe,
W is oxygen and
Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

One aspect 8 relates to compounds according to aspect 7, in which
$Z^1$ is $CF_2CF_3$,
$Z^2$ is $CF_3$,
$Z^3$ is $CH_3$,
the $R^1$, $R^6$ radicals are each hydrogen (n=0),
$A_1$ is C—H,
$A_2$ is N,
$A_3$ is C—H, C—Cl, C—F, C—$CH_3$,
$A_4$ is C—H, C—F, C—OMe,
W is oxygen and
Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

One aspect 9 relates to compounds of the general formula (Ih)

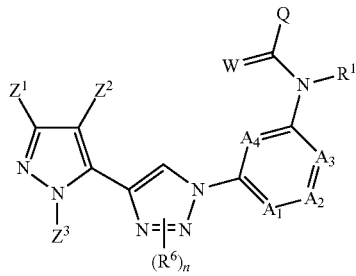 (Ih)

in which
$Z^1$ is $CF_2CF_3$,
$Z^2$ is $CF_3$, $Z^3$ is $CH_3$, the $R^1$, $R^6$ radicals are each hydrogen (n=0), $A_1$, $A_2$ are C—H, $A_3$ is C—H, C—Cl, C—F, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

One aspect 10 relates to compounds according to aspect 9, in which $Z^1$ is $CF_2CF_3$, $Z^2$ is $CF_3$, $Z^3$ is $CH_3$, the $R^1$, $R^6$ radicals are each hydrogen (n=0), $A_1$ is C—H, $A_2$ is N, $A_3$ is C—H, C—Cl, C—F, C—$CH_3$, $A_4$ is C—H, C—F, C—OMe, W is oxygen and Q is methyl, ethyl, cyclopropyl, 1-chlorocyclopropyl, 1-cyanocyclopropyl, 2,2,2-trifluoroethyl, 1,1,2,2-tetrafluoroethyl, phenyl, 4-fluorophenyl, 2-fluorophenyl, 3-fluorophenyl, 3,5-difluorophenyl, 2,6-difluorophenyl, 2-thiophenyl, 3-thiophenyl, 3-chloro-3-thiophenyl, 1-methyl-4-pyrazolyl, 4-pyridinyl, 3-chloro-2-pyridinyl, 2-chloro-4-pyridinyl, 3-fluoro-4-pyridinyl, 2,6-dichloro-4-pyridinyl.

Aspect 11 relates to the use of compounds of the general formulae (I), (Ia), (Ib), (Ic), (Id), (Ie), (If), (Ig), (Ih), (Ii) and (Ij) according to any of aspects 1 to 10 for control of insects, arachnids and nematodes.

Aspect 12 relates to pharmaceutical compositions comprising at least one compound according to any of aspects 1 to 10.

Aspect 13 relates to compounds according to any of aspects 1 to 10 as medicaments.

Aspect 14 relates to the use of compounds according to any of aspects 1 to 10 for production of pharmaceutical compositions for control of parasites in animals Aspect 15 relates to processes for producing crop protection compositions comprising compounds according to any of aspects 1 to 10 and customary extenders and/or surfactants.

Aspect 16 relates to methods for controlling pests, characterized in that a compound according to any of aspects 1 to 10 is allowed to act on the pests and/or their habitat.

Aspect 17 relates to the use of compounds according to any of aspects 1 to 10 for protection of propagation material of plants.

A particularly preferred embodiment of the present invention is directed, in an aspect 18, to compounds of the formula (Ic)

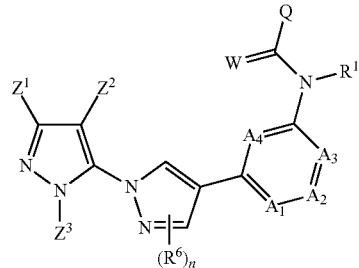

(Ic)

in which $R^1$ is hydrogen or an optionally independently mono- to hepta-halogen-, -cyano-, -alkoxy- or -alkoxycarbonyl-substituted $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_3$-alkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, most preferably hydrogen;

the following chemical moieties are as follows:

$A_1$ is $CR^2$ or nitrogen, $A_2$ is $CR^3$ or nitrogen, $A_3$ is $CR^4$ or nitrogen, and $A_4$ is $CR^5$ or nitrogen, but not more than three of the chemical moieties $A_1$ to $A_4$ are simultaneously nitrogen;

$R^2$, $R^3$, $R^4$ and $R^5$ are each independently hydrogen, halogen, cyano, nitro, or an optionally independently mono- to hepta-halogen-, -cyano-, -alkoxy- and -alkoxycarbonyl-substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

W is oxygen or sulphur;

Q is hydrogen, amino or one of the following independently mono- to hepta-hydroxy-, -nitro-, -amino-, -halogen-, -alkoxy-, -cyano-, -hydroxycarbonyl-, -alkoxycarbonyl-, -alkylcarbamoyl-, -cycloalkylcarbamoyl-, -phenyl-substituted moieties: $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_1$-$C_6$-hydroxyalkyl, aryl($C_1$-$C_3$)-alkyl, heteroaryl($C_1$-$C_3$)-alkyl, $C_1$-$C_4$-alkoxycarbonyl, N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino; or Q is hydrogen, amino or one of the moieties selected from $C_1$-$C_6$-alkyl, $C_1$-$C_6$-alkyloxy, $C_2$-$C_6$-alkenyl, $C_2$-$C_6$-alkynyl, $C_3$-$C_6$-cycloalkyl, 5- or 6-membered heterocyclyl, $C_1$-$C_6$-alkyl-$C_3$-$C_6$-cycloalkyl, $C_3$-$C_6$-cycloalkyl-$C_1$-$C_6$-alkyl, $C_6$-$C_{10}$-aryl-($C_1$-$C_3$)-alkyl, 5- or 6-membered heteroaryl-($C_1$-$C_3$)-alkyl, $C_1$-$C_4$-alkoxycarbonyl, each of which is optionally independently substituted by 1, 2, 3, 4, 5, 6 or 7 substituents selected from the group consisting of hydroxyl, nitro, amino, halogen, oxo, benzyloxy, $C_3$-$C_6$-cycloalkyl, $C_1$-$C_6$-alkoxy, cyano, hydroxycarbonyl, $C_1$-$C_4$-alkoxycarbonyl, $C_1$-$C_6$-alkylcarbamoyl, $C_3$-$C_6$-cycloalkylcarbamoyl, N,N-di-$C_1$-$C_4$-alkylamino, phenyl optionally substituted by 1, 2 or 3 substituents independently selected from the group of substituents consisting of halogen, $C_1$-$C_6$-alkoxy, $C_1$-$C_6$-haloalkoxy and $C_1$-$C_6$-alkyl, phenylthio optionally substituted by 1, 2 or 3 substituents independently selected from the group of substituents consisting of halogen, $C_1$-$C_6$-alkoxy, $C_1$-$C_6$-haloalkoxy and $C_1$-$C_6$-alkyl, 5- or 6-membered heteroaryl (e.g. pyrazolyl) optionally substituted by 1, 2 or 3 substituents independently selected from the group of substituents consisting of halogen, $C_1$-$C_6$-alkoxy, $C_1$-$C_6$-haloalkoxy and $C_1$-$C_6$-alkyl, or is an N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino moiety; or Q is an aryl substituted by 0, 1, 2, 3 or 4 V substituents or a 5- or 6-membered heteroaryl substituted by 0, 1, 2, 3 or 4 V substituents, or Q is a bicyclic heterocycle substituted by 0, 1, 2, 3 or 4 V substituents or a bicyclic carbocycle substituted by 0, 1, 2, 3 or 4 V substituents; where V is independently halogen, cyano, nitro or an optionally independently mono- to hepta-halogen, -cyano-, -alkoxy- or -alkoxycarbonyl-substituted $C_1$-$C_6$-alkyl, $C_1$-$C_6$-haloalkyl, $C_2$-$C_4$-alkenyl, $C_2$-$C_4$-alkynyl, $C_3$-$C_6$-cycloalkyl, $C_1$-$C_6$-alkoxy, $C_1$-$C_6$-haloalkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino;

$R^6$ is independently halogen, cyano, nitro, amino or an optionally mono- to hepta-halogen-substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n has the values of 0-1;

$Z^1$ is an optionally independently mono- to hepta-halogen-, -cyano-, -alkoxy- and -alkoxycarbonyl-substituted $C_1$-$C_6$-alkyl, $C_3$-$C_6$-cycloalkyl, and $Z^2$ is hydrogen, halogen, cyano, nitro, amino or an independently mono- to hepta-halogen-, -cyano-, -alkoxy- or -alkoxycarbonyl-substituted $C_1$-$C_6$-alkyl, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and $Z^3$ is hydrogen or an optionally independently mono- to hepta-halogen-, -cyano-, -alkoxy- and -alkoxycarbonyl-substituted $C_1$-$C_6$-alkyl, $C_3$-$C_6$-cycloalkyl, $C_3$-$C_4$-alkenyl, $C_3$-$C_4$-alkynyl, or an optionally independently mono- to penta-halogen-, -cyano-, -alkoxy- and -alkoxycarbonyl-substituted aryl or hetaryl.

A further preferred embodiment is directed, in an aspect 19, to compounds of the formula (Ic) according to aspect 18 in which $R^6$ is hydrogen or $C_1$-$C_6$-alkyl and n is 0 or 1, more preferably in which $R^6$ is hydrogen.

A further preferred embodiment is directed, in an aspect 20, to compounds of the formula (Ic) according to aspect 18 or 19 in which the following chemical moieties are as follows:
$A_1$ is $CR^2$,
$A_2$ is $CR^3$ or nitrogen,
$A_3$ is $CR^4$, and
$A_4$ is $CR^5$, where
$R^2$ and $R^5$ are each independently hydrogen, fluorine, chlorine, bromine, iodine, $C_1$-$C_4$-alkyl (e.g. methyl) and $C_1$-$C_4$-alkoxy (e.g. methoxy) and $R^3$ and $R^4$ are each independently hydrogen, fluorine, chlorine, bromine, iodine, cyano, nitro, $C_1$-$C_4$-alkyl (e.g. methyl), $C_1$-$C_4$-haloalkyl, more preferably in which $R^2$ and $R^5$ are each independently hydrogen, fluorine, methyl and methoxy, and $R^3$ and $R^4$ are each independently hydrogen, fluorine, chlorine, methyl.

A further preferred embodiment is directed, in an aspect 21, to compounds of the formula (Ic) according to any of aspects 18 to 21 in which the following chemical moieties are as follows:
$A_1$ is $CR^2$,
$A_2$ is $CR^3$,
$A_3$ is $CR^4$, and
$A_4$ is $CR^5$, where
$R^2$ is hydrogen, $R^3$ is hydrogen, $R^4$ is hydrogen, fluorine, chlorine, bromine, iodine, methyl or ethyl and
$R^5$ is hydrogen, fluorine, chlorine, bromine or iodine, more preferably $R^2$ is hydrogen, $R^3$ is hydrogen,
$R^4$ is hydrogen, fluorine, chlorine or methyl and $R^5$ is hydrogen or fluorine.

A further preferred embodiment is directed, in an aspect 22, to compounds of the formula (Ic) according to any of aspects 18 to 21 in which the following chemical moieties are as follows:
$A_1$ is $CR^2$,
$A_2$ is nitrogen,
$A_3$ is $CR^4$, and
$A_4$ is $CR^5$, where
$R^2$ is hydrogen, $R^4$ is hydrogen, fluorine, chlorine, bromine, iodine, methyl or ethyl and $R^5$ is hydrogen, fluorine, chlorine, bromine or iodine, more preferably $R^2$ is hydrogen, $R^4$ is hydrogen, fluorine, chlorine or methyl, preferably fluorine, chlorine or methyl, and $R^5$ is hydrogen or fluorine, preferably hydrogen.

A further preferred embodiment is directed, in an aspect 23, to compounds of the formula (Ic) according to any of aspects 18 to 22 in which W is oxygen.

A further preferred embodiment is directed, in an aspect 24, to compounds of the formula (Ic) according to any of aspects 18 to 23 in which
$Z^1$ is an in each case optionally independently mono- to hepta-halogen- or -cyano-substituted $C_1$-$C_6$-alkyl or $C_3$-$C_6$-cycloalkyl;
$Z^2$ is an in each case optionally independently mono- to hepta-halogen- or -cyano-substituted $C_1$-$C_6$-alkyl or $C_3$-$C_6$-cycloalkyl;
$Z^3$ is hydrogen or $C_1$-$C_6$-alkyl,
more preferably in which
$Z^1$ is an in each case optionally independently mono- to hepta-halogen-substituted $C_1$-$C_6$-alkyl;
$Z^2$ is an in each case optionally independently mono- to hepta-halogen-substituted $C_1$-$C_6$-alkyl;
$Z^3$ is $C_1$-$C_6$-alkyl,
even more preferably in which
$Z^1$ is perfluorinated $C_1$-$C_3$-alkyl (e.g. $C_2F_5$);
$Z^2$ is perfluorinated $C_1$-$C_3$-alkyl (e.g. $CF_3$);
$Z^3$ is $C_1$-$C_4$-alkyl (e.g. methyl).

A very particularly preferred embodiment is directed, in an aspect 25, to compounds of the formula (Ic) according to any of aspects 18 to 24 in which $Z^1$ is $C_2F_5$, $Z^2$ is $CF_3$ and $Z^3$ is methyl.

A further preferred embodiment is directed, in an aspect 26, to compounds of the formula (Ic) according to any of aspects 18 to 25 in which Q is hydrogen, amino or one of the optionally independently mono- to hepta-hydroxyl-, -nitro-, -amino-, -halogen-, -alkoxy-, -cyano-, -hydroxycarbonyl-, -alkoxycarbonyl-, -alkylcarbamoyl-, -cycloalkylcarbamoyl-, -phenyl-substituted moieties $C_1$-$C_6$-alkyl, $C_2$-$C_6$-alkenyl, $C_2$-$C_6$-alkynyl, $C_3$-$C_6$-cycloalkyl, $C_2$-$C_5$-heterocyclyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_1$-$C_6$-hydroxyalkyl, aryl($C_1$-$C_3$)-alkyl, heteroaryl($C_1$-$C_3$)-alkyl, $C_1$-$C_4$-alkoxycarbonyl, N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino, or is an aryl substituted by 0, 1, 2, 3 or 4 V substituents or is a 5- or 6-membered heteroaryl substituted by 0, 1, 2, 3 or 4 V substituents, where V is independently halogen, cyano, nitro or an optionally independently mono- to hepta-halogen-, -cyano-, -alkoxy- and -alkoxycarbonyl-substituted $C_1$-$C_6$-alkyl, $C_2$-$C_4$-alkenyl, $C_2$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino A further more preferred embodiment is directed, in an aspect 27, to compounds of the formula (Ic) according to any of aspects 18 to 25 in which Q is hydrogen, amino or one of the moieties selected from $C_1$-$C_6$-alkyl, $C_1$-$C_6$-alkyloxy, $C_2$-$C_6$-alkenyl, $C_2$-$C_6$-alkynyl, $C_3$-$C_6$-cycloalkyl, 5- or 6-membered heterocyclyl, $C_1$-$C_6$-alkyl-$C_3$-$C_6$-cycloalkyl, $C_3$-$C_6$-cycloalkyl-$C_1$-$C_6$-alkyl, $C_6$-$C_{10}$-aryl-($C_1$-$C_3$)-alkyl, 5- or 6-membered heteroaryl-($C_1$-$C_3$)-alkyl, $C_1$-$C_4$-alkoxycarbonyl, each of which is optionally independently substituted by 1, 2, 3, 4, 5, 6 or 7 substituents selected from the group consisting of hydroxy, nitro, amino, halogen, oxo, benzyloxy, $C_3$-$C_6$-cycloalkyl, $C_1$-$C_6$-alkoxy, $C_1$-$C_6$-haloalkoxy, cyano, hydroxycarbonyl, $C_1$-$C_4$-alkoxycarbonyl, $C_1$-$C_6$-alkylcarbamoyl, $C_3$-$C_6$-cycloalkylcarbamoyl, N,N-di-$C_1$-$C_4$-alkylamino, phenyl optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, phenylthio optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, phenyloxy optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, 5- or 6-membered heteroaryl (e.g. pyrazolyl or thiophenyl) optionally substituted by 1, 2 or 3 substituents selected independently from the group of substituents consisting of halogen, $C_1$-$C_6$-alkoxy, $C_1$-$C_6$-haloalkoxy and $C_1$-$C_6$-alkyl, or is an N—$C_1$-$C_4$-alkylamino, N—$C_1$-$C_4$-alkylcarbonylamino, N,N-di-$C_1$-$C_4$-alkylamino, $C_1$-$C_4$-alkylsulphonylamino moiety; or Q is an aryl substituted by 0, 1, 2, 3 or 4 V substituents or a 5- or 6-membered heteroaryl substituted by 0, 1, 2, 3 or 4 V substituents, or Q is a bicyclic heterocycle substituted by 0, 1, 2, 3 or 4 V substituents or a bicyclic carbocycle substituted by 0, 1, 2, 3 or 4 V substituents; where V is independently halogen, cyano, nitro or an optionally independently mono- to hepta-halogen, -cyano-, -alkoxy- and -alkoxycarbonyl-substituted $C_1$-$C_6$-alkyl, $C_1$-$C_6$-haloalkyl, $C_2$-$C_4$-alkenyl, $C_2$-$C_4$-alkynyl, $C_3$-$C_6$-cycloalkyl, $C_1$-$C_6$-alkoxy, $C_1$-$C_6$-haloalkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N,N-di-($C_1$-$C_6$-alkyl)amino.

A further preferred embodiment is directed, in an aspect 28, to compounds of the formula (Ic) according to any of aspects 18 to 25 or 27 in which Q is hydrogen;

$C_1$-$C_6$-alkyl optionally substituted by 1, 2, 3 or 4 substituents selected independently from the group consisting of fluorine, chlorine, bromine, iodine, cyano, oxo, $C_1$-$C_4$-alkoxy, $C_1$-$C_4$-haloalkoxy, benzyloxy, N,N-di-$C_1$-$C_4$-alkylamino, $C_3$-$C_6$-cycloalkyl, phenylthio optionally substituted by 1, 2, 3 or 4 substituents selected independently from the group consisting of fluorine, chlorine, bromine, iodine, $C_1$-$C_4$-alkoxy, $C_1$-$C_4$-alkyl and $C_1$-$C_4$-haloalkyl, phenyloxy, optionally substituted by 1, 2, 3 or 4 substituents selected independently from the group consisting of fluorine, chlorine, bromine, iodine, $C_1$-$C_4$-alkoxy, $C_1$-$C_4$-alkyl and $C_1$-$C_4$-haloalkyl, phenyl optionally substituted by 1, 2, 3 or 4 substituents selected independently from the group consisting of fluorine, chlorine, bromine, iodine, $C_1$-$C_4$-alkoxy, and $C_1$-$C_4$-haloalkyl, pyrazolyl optionally substituted by 1, 2, 3 or 4 substituents selected independently from the group consisting of fluorine, chlorine, bromine, iodine, $C_1$-$C_4$-alkoxy, $C_1$-$C_4$-alkyl and $C_1$-$C_4$-haloalkyl, thiophenyl optionally substituted by 1, 2, 3 or 4 substituents selected independently from the group consisting of fluorine, chlorine, bromine, iodine, $C_1$-$C_4$-alkoxy, $C_1$-$C_4$-alkyl and $C_1$-$C_4$-haloalkyl;

$C_3$-$C_6$-cycloalkyl optionally substituted by 1, 2, 3 or 4 substituents selected independently from the group consisting of $C_1$-$C_4$-alkoxy, fluorine, chlorine, bromine, iodine, cyano, $C_1$-$C_4$-alkyl, phenyl optionally substituted by 1, 2, 3 or 4 substituents selected independently from the group consisting of fluorine, chlorine, bromine, iodine, $C_1$-$C_4$-alkoxy, $C_1$-$C_4$-alkyl and $C_1$-$C_4$-haloalkyl; or is a phenyl, naphthyl, pyridazinyl, pyrazinyl, pyrimidinyl, triazinyl, pyridinyl, pyrazolyl, thiazolyl, isothiazolyl, oxazolyl, isoxazolyl, triazolyl, imidazolyl, furanyl, thiophenyl, pyrrolyl, oxadiazolyl, thiadiazolyl, benzothiophenyl, benzofuranyl, [1,2,4]triazolo[1,5-a]pyrimidinyl, 1,3-benzodioxolyl or tetralinyl, each of which is substituted by 0, 1, 2, 3 or 4 V substituents, where V is independently fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N,N-di-$C_1$-$C_4$-alkylamino.

A further preferred embodiment is directed, in an aspect 29, to compounds of the formula (Ic) according to any of aspects 18 to 25 or 27 to 28 in which Q is $C_1$-$C_6$-alkyl optionally substituted by 1, 2, 3 or 4 substituents selected independently from the group consisting of fluorine, chlorine, bromine, iodine, oxo, $C_1$-$C_4$-alkoxy, benzyloxy, N,N-di-$C_1$-$C_4$-alkylamino, $C_3$-$C_6$-cycloalkyl, phenylthio, phenyloxy, phenyl optionally substituted by 1, 2, 3 or 4 substituents independently selected from the group consisting of fluorine, chlorine, bromine, iodine, $C_1$-$C_4$-alkoxy, $C_1$-$C_4$-alkyl and $C_1$-$C_4$-haloalkyl, pyrazolyl and thiophenyl optionally substituted by 1, 2, 3 or 4 substituents independently selected from the group consisting of $C_1$-$C_4$-alkyl and $C_1$-$C_4$-haloalkyl;

$C_3$-$C_6$-cycloalkyl optionally substituted by 1, 2, 3 or 4 substituents selected independently from the group consisting of $C_1$-$C_4$-alkoxy, fluorine, chlorine, bromine, iodine, cyano, $C_1$-$C_4$-alkyl, phenyl optionally substituted by 1, 2, 3 or 4 substituents selected independently from the group consisting of fluorine, chlorine, bromine, iodine and $C_1$-$C_4$-alkyl; or is a phenyl, pyrimidinyl, pyridinyl, pyrazolyl, oxazolyl, isoxazolyl, furanyl, thiophenyl, benzothiophenyl, benzofuranyl, [1,2,4]triazolo[1,5-a]pyrimidinyl, 1,3-benzodioxolyl or tetralinyl, each of which is substituted by 0, 1, 2, 3 or 4 V substituents, where V is independently fluorine, chlorine, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N,N-di-$C_1$-$C_4$-alkylamino.

A further preferred embodiment is directed, in an aspect 30, to compounds of the formula (Ic) according to any of aspects 18 to 25 or 27 to 29 in which Q is $C_1$-$C_4$-alkyl optionally substituted by 1, 2, 3 or 4 substituents selected independently from the group consisting of
fluorine, chlorine, bromine, iodine, oxo, $C_1$-$C_4$-alkoxy, benzyloxy, N,N-di-$C_1$-$C_4$-alkylamino, $C_3$-$C_6$-cycloalkyl, phenylthio, phenyloxy, phenyl optionally substituted by 1, 2 or 3 substituents independently selected from the group consisting of fluorine, chlorine, bromine, iodine, $C_1$-$C_4$-alkoxy, $C_1$-$C_4$-alkyl and $C_1$-$C_4$-haloalkyl, pyrazolyl and thiophenyl optionally substituted by 1 or 2 substituents independently selected from the group consisting of $C_1$-$C_4$-alkyl and $C_1$-$C_4$-haloalkyl;

$C_3$-$C_6$-cycloalkyl optionally substituted by 1 or 2 substituents selected independently from the group consisting of
$C_1$-$C_4$-alkoxy, fluorine, chlorine, bromine, iodine, cyano, $C_1$-$C_4$-alkyl, phenyl optionally substituted by 1 or 2 substituents selected independently from the group consisting of fluorine, chlorine, bromine, iodine and $C_1$-$C_4$-alkyl; or is a phenyl, pyrimidinyl, pyridinyl, pyrazolyl, oxazolyl, isoxazolyl, furanyl, thiophenyl, benzothiophenyl, benzofuranyl, [1,2,3]triazolo[1,5-a]pyrimidinyl, 1,3-benzodioxolyl or tetralinyl, each of which is substituted by 0, 1, 2 or 3 V substituents, where V is independently fluorine, chlorine, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N,N-di-$C_1$-$C_2$-alkylamino.

A further preferred embodiment is directed, in an aspect 31, to compounds of the formula (Ic) according to any of aspects 18 to 25 or 27 to 30 in which Q is $C_1$-$C_4$-alkyl optionally substituted by 1, 2, 3 or 4 substituents selected independently from the group consisting of
fluorine, oxo, $C_1$-$C_4$-alkoxy, benzyloxy, N,N-di-$C_1$-$C_4$-alkylamino, $C_3$-$C_6$-cycloalkyl, phenylthio, phenyloxy, phenyl optionally substituted by 1, 2 or 3 substituents independently selected from the group consisting of fluorine, chlorine, $C_1$-$C_4$-alkoxy, $C_1$-$C_4$-alkyl and $C_1$-$C_4$-haloalkyl, pyrazolyl and thiophenyl optionally substituted by 1 or 2 substituents independently selected from the group consisting of $C_1$-$C_4$-alkyl and $C_1$-$C_4$-haloalkyl;

$C_3$-$C_6$-cycloalkyl optionally substituted by 1 or 2 substituents selected independently from the group consisting of
$C_1$-$C_4$-alkoxy, chlorine, cyano, $C_1$-$C_4$-alkyl, phenyl optionally substituted by 1 or 2 substituents selected independently from the group consisting of chlorine and $C_1$-$C_4$-alkyl; or is a phenyl, pyrimidinyl, pyridinyl, pyrazolyl, oxazolyl, isoxazolyl, furanyl, thiophenyl, benzothiophenyl, benzofuranyl, [1,2,3]triazolo[1,5-a]pyrimidinyl, 1,3-benzodioxolyl or tetralinyl, each of which is substituted by 0, 1, 2 or 3 V substituents, where V is independently fluorine, chlorine, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N,N-di-$C_1$-$C_2$-alkylamino.

A further preferred embodiment is directed, in an aspect 32, to compounds of the formula (Ic) according to any of aspects 18 to 25 or 27 to 31 in which Q is $C_1$-$C_6$-alkyl optionally substituted by 1, 2, 3 or 4 substituents selected independently from the group consisting of
fluorine, oxo, methoxy, ethoxy, benzyloxy, N,N-dimethylamino, $C_3$-$C_6$-cycloalkyl, phenylthio, phenyloxy, phenyl optionally substituted by 1, 2 or 3 substituents independently selected from the group consisting of fluorine, chlorine, $C_1$-$C_4$-alkoxy, $C_1$-$C_4$-alkyl and $C_1$-$C_4$-haloalkyl, pyrazolyl and thiophenyl optionally substituted by 1 or 2 substituents independently selected from the group consisting of $C_1$-$C_4$-alkyl and $C_1$-$C_4$-haloalkyl;

$C_3$-$C_6$-cycloalkyl optionally substituted by 1 or 2 substituents selected independently from the group consisting of
$C_1$-$C_4$-alkoxy, chlorine, cyano, $C_1$-$C_2$-alkyl, phenyl optionally substituted by 1 or 2 substituents selected independently from the group consisting of chlorine and $C_1$-$C_2$-alkyl; or is a phenyl, pyrimidinyl, pyridinyl, pyrazolyl, oxazolyl, isoxazolyl, furanyl, thiophenyl, benzothiophenyl, benzofuranyl, [1,2,3]triazolo[1,5-a]pyrimidinyl, 1,3-benzodioxolyl or tetralinyl, each of which is substituted by 0, 1, 2 or 3 V substituents, where V is independently fluorine, chlorine, cyano, nitro, $C_1$-$C_4$-alkyl, $C_1$-$C_2$-haloalkyl, $C_3$-$C_6$-cycloalkyl, $C_1$-$C_2$-alkoxy, $C_1$-$C_2$-haloalkoxy, N,N-di-$C_1$-$C_2$-alkylamino.

A further preferred embodiment is directed, in an aspect 33, to compounds of the formula (Ic) according to any of aspects 18 to 25 or 27 to 32 in which Q is optionally independently mono- or di-fluorine-, -methyl-, -cyano-, -chlorine-substituted pyridinyl (e.g. 4-pyridinyl, 3-F-4-pyridinyl, 3-Cl-2-pyridinyl, 2-Cl-4-pyridinyl, 2,6-Cl$_2$-4-pyridinyl, 2-Cl-3-pyridinyl, 2-Cl-6-Me-4-pyridinyl, 3-pyridinyl, 3-F-5-pyridinyl, 2-Me-4-pyridinyl, 2-F-4-pyridinyl, 2-CN-5-pyridinyl, 2-Cl-5-pyridinyl, 2-Cl-5-pyridinyl, 2-F-5-pyridinyl, 2-CN-5-pyridinyl), optionally mono-Cl—, -methoxy-, -methyl- or —CN-substituted $C_3$-$C_6$-cycloalkyl (e.g. cyclopropyl, 1-CN-cyclopropyl, 1-Cl-cyclopropyl, 4-methoxycyclohex-1-yl, 1-methylcyclohexyl, 1-methylcyclopropyl, cyclopentyl), optionally independently mono- or di- or tri-fluorine-, -methoxy-, -ethoxy-, -trifluoromethoxy-, -cyano-, -trifluoromethyl-, -dimethylamino-, -methyl-, -ethyl-, -propyl-substituted phenyl (e.g. phenyl, 2-F-phenyl, 3-F-phenyl, 3,5-F$_2$-phenyl, 2,6-F$_2$-phenyl, 4-F-phenyl, 3-methoxyphenyl, 3-CF$_3$-4-F-phenyl, 2,6-bismethoxyphenyl, 4-(dimethylamino)phenyl, 2,4,6-trisisopropylphenyl, 3-CF$_3$-phenyl, 4-Me-phenyl, 2,3-F$_2$-phenyl, 2-ethoxyphenyl, 2-(trifluoromethoxy)phenyl, 3-cyanophenyl, 2,3-dimethylphenyl, 4-CN-phenyl, 3,4-dimethylphenyl, 3-Me, 4-F-phenyl, 3-F, 4-Me-phenyl, 3-MeO, 4-F-phenyl, 3-F, 4-MeO-phenyl, 4-Cl, 3-F-phenyl, 3-methoxy-4-Me-phenyl, 3-EtO-4-F-phenyl), optionally mono-methoxy- or -ethoxy-substituted $C_1$-$C_6$-alkyl or $C_1$-$C_6$-haloalkyl (e.g. CHF$_2$CF$_2$—, CF$_3$CH$_2$—, methyl, ethyl, propyl, 1,1,2,2-tetramethylethyl, (1,1-dimethyl)-2-F-ethyl, methoxymethyl, 1-methylpropyl, 2-methoxyethyl, (R)-1-F-ethyl, 2-Me-prop-1-yl, butyl, 2,2-dimethylprop-1-yl, 1,1-dimethyl-2-ethoxyethyl), optionally independently mono-, di- or tri-methyl-, -ethyl-, -propyl-, -butyl-, -nitro-substituted pyrazolyl (e.g. 1-methyl-4-pyrazolyl, 1-methyl-3-tBu-4-$NO_2$-pyrazolyl), thiazolyl (e.g. 1-thiazolyl), optionally mono-chlorine-substituted thiophenyl (e.g. 3-thiophenyl, 2-thiophenyl, 3-Cl-2-thiophenyl), pyrimidinyl (e.g. pyrimidin-3-yl, pyrimidin-2-yl), optionally independently mono- or di-halomethyl-, -methyl-substituted [1,2,4]triazolo[1,5-a]pyrimidin-2-yl (e.g. 7-(difluoromethyl)-5-methyl-[1,2,4]triazolo[1,5-a]pyrimidin-2-yl), optionally independently mono- or di-chlorine-, -methyl-substituted benzothiophenyl (e.g. 3-Cl-benzothiophen-2-yl, 3-Cl-6-Me-benzothiophen-2-yl), optionally independently mono- or di-methyl-, -trifluoromethyl-substituted furanyl (e.g. 3-Me-2-benzofuranyl, 2-$CF_3$-4-Me-furan-2-yl, 2-Me-3-furanyl), optionally mono- or di-methyl-, -trifluoromethyl-substituted thiophenyl (e.g. 5-Me-thiophen-2-yl), optionally mono-methyl-substituted isoxazolyl (e.g. 5-methylisoxazol-4-yl), optionally mono- or di-fluorine-substituted 1,3-benzodioxolyl (e.g. 2,2-difluoro-1,3-benzodioxol-5-yl or 1,3-benzodioxol-5-yl).

A further embodiment is directed, in an aspect 34, to compounds of the formula (Ic) according to any of aspects 18 to 25 or 27 to 32 in which Q is phenylthiomethyl, 1-phenylethyl, phenylcyclopentylmethyl, benzyloxymethyl, phenoxyethyl, 1-Me, 1-(3-Cl-Ph)-ethyl, 1-(4-Cl-Ph)-2-Me-prop-1-yl, 3-F-benzyl, 3-$CF_3$-benzyl, 3-CF3-4-Me-pyrazol-1-ylmethyl rac-1-phenoxyethyl, 1-phenylprop-1-yl, 2-phenylethyl, 2-Cl-4-F-benzyl or tetralinyl, 1-(4-Me-Ph)-cyclohex-1-yl, 1-Ph-cycloprop-1-yl, 1-(4-Cl-Ph)-cyclobut-1-yl, 1-(4-Cl-Ph)-cyclopent-1-yl, 2-thiophenylmethyl, $(Me)_2NC(O)C(O)$—.

A further preferred embodiment is directed, in an aspect 35, to compounds of the formula (Ic) according to any of aspects 18 to 34 which are a compound of the formula (Ic-1)

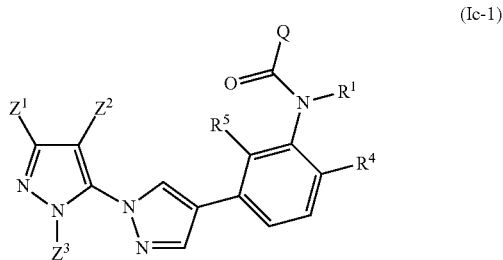

(Ic-1)

Inventive compounds of the formula (Ic-1) are compounds of the general formula (Ic) where W=O, $A_1$=$A_2$=CH, $A_3$=$CR^4$, $A_4$=$CR^5$ and $R^6$=H (i.e. n=0).

A further preferred embodiment is directed, in an aspect 36, to compounds of the formula (Ic-1) according to aspect 35 in which Q is optionally independently mono- or di-fluorine-, -methyl-, -cyano-, -chlorine-substituted pyridinyl (e.g. 4-pyridinyl, 3-F-4-pyridinyl, 3-Cl-2-pyridinyl, 2-Cl-4-pyridinyl, 2,6-$Cl_2$-4-pyridinyl, 2-Cl-3-pyridinyl, 2-Cl-6-Me-4-pyridinyl, 3-pyridinyl, 3-F-5-pyridinyl, 2-Me-4-pyridinyl, 2-F-4-pyridinyl, 2-CN-5-pyridinyl, 2-Cl-5-pyridinyl, 2-Cl-5-pyridinyl, 2-F-5-pyridinyl, 2-CN-5-pyridinyl), optionally mono-Cl—, -methoxy-, -methyl- or —CN-substituted $C_3$-$C_6$-cycloalkyl (e.g. cyclopropyl, 1-CN-cyclopropyl, 1-Cl-cyclopropyl, 4-methoxycyclohex-1-yl, 1-methylcyclohexyl, 1-methylcyclopropyl, cyclopentyl), optionally independently mono- or di- or tri-fluorine-, -methoxy-, -ethoxy-, -trifluoromethoxy-, -cyano-, -trifluoromethyl-, -dimethylamino-, -methyl-, -ethyl-, -propyl-substituted phenyl (e.g. phenyl, 2-F-phenyl, 3-F-phenyl, 3,5-$F_2$-phenyl, 2,6-$F_2$-phenyl, 4-F-phenyl, 3-methoxyphenyl, 3-$CF_3$-4-F-phenyl, 2,6-bismethoxyphenyl, 4-(dimethylamino)phenyl, 2,4,6-trisisopropylphenyl, 3-$CF_3$-phenyl, 4-Me-phenyl, 2,3-$F_2$-phenyl, 2-ethoxyphenyl, 2-(trifluoromethoxy)phenyl, 3-cyanophenyl, 2,3-dimethylphenyl, 4-CN-phenyl, 3,4-dimethylphenyl, 3-Me, 4-F-phenyl, 3-F, 4-Me-phenyl, 3-MeO, 4-F-phenyl, 3-F, 4-MeO-phenyl, 4-Cl, 3-F-phenyl, 3-methoxy-4-Me-phenyl, 3-EtO-4-F-phenyl), optionally mono-methoxy- or -ethoxy-substituted $C_1$-$C_6$-alkyl or $C_1$-$C_6$-haloalkyl (e.g. $CHF_2CF_2$—, $CF_3CH_2$—, methyl, ethyl, propyl, 1,1,2,2-tetramethylethyl, (1,1-dimethyl)-2-F-ethyl, methoxymethyl, 1-methylpropyl, 2-methoxyethyl, (R)-1-F-ethyl, 2-Me-prop-1-yl, butyl, 2,2-dimethylprop-1-yl, 1,1-dimethyl-2-ethoxyethyl), optionally independently mono-, di- or tri-methyl-, -ethyl-, -propyl-, -butyl-, -nitro-substituted pyrazolyl (e.g. 1-methyl-4-pyrazolyl, 1-methyl-3-tBu-4-$NO_2$-pyrazolyl), thiazolyl (e.g. 1-thiazolyl), optionally mono-chlorine-substituted thiophenyl (e.g. 3-thiophenyl, 2-thiophenyl, 3-Cl-2-thiophenyl), pyrimidinyl (e.g. pyrimidin-3-yl, pyrimidin-2-yl), optionally independently mono- or di-halomethyl-, -methyl-substituted [1,2,4]triazolo[1,5-a]pyrimidin-2-yl (e.g. 7-(difluoromethyl)-5-methyl-[1,2,4]triazolo[1,5-a]pyrimidin-2-yl), optionally independently mono- or di-chlorine-, -methyl-substituted benzothiophenyl (e.g. 3-Cl-benzothiophen-2-yl, 3-Cl-6-Me-benzothiophen-2-yl), optionally independently mono- or di-methyl-, -trifluoromethyl-substituted furanyl (e.g. 3-Me-2-benzofuranyl, 2-$CF_3$-4-Me-furan-2-yl, 2-Me-3-furanyl), optionally mono- or di-methyl-, -trifluoromethyl-substituted thiophenyl (e.g. 5-Me-thiophen-2-yl), optionally mono-methyl-substituted isoxazolyl (e.g. 5-methylisoxazol-4-yl), optionally mono- or di-fluorine-substituted 1,3-benzodioxolyl (e.g. 2,2-difluoro-1,3-benzodioxol-5-yl or 1,3-benzodioxol-5-yl).

A further preferred embodiment is directed, in an aspect 37, to compounds of the formula (Ic-1) according to aspect 35 in which Q is phenylthiomethyl, 1-phenylethyl, phenylcyclopentylmethyl, benzyloxymethyl, phenoxyethyl, 1-Me, 1-(3-Cl-Ph)-ethyl, 1-(4-Cl-Ph)-2-Me-prop-1-yl, 3-F-benzyl, 3-$CF_3$-benzyl, 3-CF3-4-Me-pyrazol-1-yl-methyl rac-1-phenoxyethyl, 1-phenylprop-1-yl, 2-phenylethyl, 2-Cl-4-F-benzyl or tetralinyl, 1-(4-Me-Ph)-cyclohex-1-yl, 1-Ph-cycloprop-1-yl, 1-(4-Cl-Ph)-cyclobut-1-yl, 1-(4-Cl-Ph)-cyclopent-1-yl, 2-thiophenylmethyl, $(Me)_2NC(O)C(O)$—.

A further preferred embodiment is directed, in an aspect 38, to compounds of the formula (Ic-1) according to aspect 35 in which Q is a radical as specified in aspects 36 and 37.

A further preferred embodiment is directed, in an aspect 39, to compounds of the formula (Ic) according to aspect 35 in which Q is 4-F-phenyl, 3-MeO-4-F-phenyl, 3-Cl-2-pyridinyl, 2-CN-5-pyridinyl, 4-pyridinyl.

A further preferred embodiment is directed, in an aspect 40, to compounds of the formula (Ic-1) according to aspect 35 in which Q is a radical as specified in aspects 36, 37 and 38.

A further preferred embodiment is directed, in an aspect 41, to compounds of the formula (Ic) according to any of aspects 18 to 34 which are a compound of the formula (Ic-2)

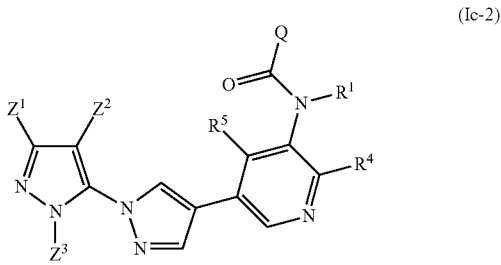

(Ic-2)

Inventive compounds of the formula (Ic-2) are compounds of the general formula (Ic) where W=O, $A_1$=CH, $A_2$=N, $A_3$=CR$^4$, $A_4$=CR$^5$ and R$^6$=H (i.e. n=0).

A further preferred embodiment is directed to compounds of the formula (Ic-2) according to aspect 41 in which Q is 4-F-phenyl, 3-MeO, 4-F-phenyl, 3-Cl-2-pyridinyl, 2-CN-5-pyridinyl, 4-pyridinyl.

Use:

The invention also relates to methods for controlling animal pests, in which inventive compounds of the general formula (I) are allowed to act on animal pests and/or their habitat. The inventive compounds of the general formula (I) are used to control a multitude of different pests including, for example, harmful sucking insects, biting insects and other pests that are plant parasites, stored product pests, pests which destroy industrial materials and hygiene pests including parasites in the animal health sector.

Crop Protection

The inventive compounds of the formula (I), given good plant compatibility and favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in aquacultures, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

pests from the phylum of the Arthropoda, especially from the class of the Arachnida, for example *Acarus* spp., *Aceria kuko*, *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Platytetranychus multidigituli*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici.*;

from the class of the Chilopoda, for example, *Geophilus* spp., *Scutigera* spp.;

from the order or the class of the Collembola, for example, *Onychiurus armatus*.

from the class of the Diplopoda, for example, *Blaniulus guttulatus*;

from the class of the Insecta, for example from the order of the Blattodea, for example *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Baris caerulescens*, *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperomorpha xanthodera*, *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;

from the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., e.g. *Drosophila suzukii*, *Echinocnemus* spp., *Fannia* spp., *Gasterophilus* spp., *Glossina* spp., *Haematopota* spp., *Hydrellia* spp., *Hydrellia griseola*, *Hylemya* spp.,

*Hippobosca* spp., *Hypoderma* spp., *Liriomyza* spp., *Lucilia* spp., *Lutzomyia* spp., *Mansonia* spp., *Musca* spp., *Oestrus* spp.,
*Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order of the Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the homoptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma piri*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigonicla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., e.g. *Phenacoccus madeirensis*, *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., e.g. *Pseudococcus viburni*, *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*,
*Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order of the Hymenoptera, for example, *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order of the Isopoda, for example, *Armadillidium vulgare*, *Oniscus asellus*, *Porcellio scaber*;

from the order of the Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.;

from the order of the Lepidoptera, for example, *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order of the Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria*;

from the order of the Phthiraptera, for example, *Damalinia* spp., *Haematopinus* spp., *Linognathus* spp., *Pediculus* spp., *Phylloera vastatrix*, *Phtirus pubis*, *Trichodectes* spp.;

from the order of the Psocoptera, for example, *Lepinotus* spp., *Liposcelis* spp.;

from the order of the Siphonaptera, for example, *Ceratophyllus* spp., *Ctenocephalides* spp., *Pulex irritans, Tunga penetrans, Xenopsylla cheopsis;* from the order of the Thysanoptera, for example, *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order of the Zygentoma (=Thysanura), for example, *Ctenolepisma* spp., *Lepisma saccharina, Lepismodes inquilinus, Thermobia domestica;* from the class of the Symphyla, for example, *Scutigerella* spp.;

pests from the phylum of the Mollusca, especially from the class of the Bivalvia, for example *Dreissena* spp., and from the class of the Gastropoda, for example *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Formulations

The present invention further relates to formulations and use forms prepared therefrom as crop protection compositions and/or pesticides, for example drench, drip and spray liquors, comprising at least one of the inventive active ingredients. Optionally, the use forms contain further crop protection agents and/or pesticides and/or action-enhancing adjuvants such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates, and/or spreading agents, for example alkyl siloxanes and/or salts, for example organic or inorganic ammonium or phosphonium salts, for example ammonium sulphate or diammonium hydrogenphosphate, and/or retention promoters, for example dioctyl sulphosuccinate or hydroxypropylguar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. If appropriate, the formulations comprise, as well as one or more inventive active ingredients, further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which improves the biological activity of the formulation without having biological activity itself. Examples of adjuvants are agents which promote the spreading characteristics, adhesion to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable apparatuses or else before or during the application.

Auxiliaries used may be those substances which are suitable for imparting particular properties, such as particular physical, technical and/or biological properties, to the formulation of the active ingredient or to the use forms prepared from these formulations (for example ready-to-use crop protection compositions such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents essentially include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

In principle, it is possible to use any suitable solvents. Suitable solvents are, for example, aromatic hydrocarbons, for example toluene, xylene or alkylnaphthalenes, chlorinated aromatic or aliphatic hydrocarbons, for example chlorobenzene, chloroethylene or methylene chloride, aliphatic hydrocarbons, for example cyclohexane, paraffins, mineral oil fractions, mineral and vegetable oils, alcohols, for example methanol, ethanol, isopropanol, butanol or glycol or the ethers and esters thereof, ketones, for example acetone, methyl ethyl ketone, methyl isobutyl ketone or cyclohexanone, strongly polar solvents such as dimethyl sulphoxide, and water.

In principle, it is possible to use any suitable carriers. Useful carriers especially include: for example ammonium salts and natural rock flours such as kaolin, aluminas, talc, chalk, quartz, attapulgite, montmorillonite or diatomaceous earth, and synthetic rock flours such as finely divided silica, aluminium oxide and natural or synthetic silicates, resins, waxes and/or solid fertilizers. It is likewise possible to use mixtures of such carriers. Useful carriers for granules include, for example, crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under standard pressure, for example aerosol propellants such as halohydrocarbons, or else butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surface active substance is advantageous when one of the active ingredients and/or one of the inert carriers is water-insoluble and when they are applied in water.

Further auxiliaries which may be present in the formulations and the use forms derived therefrom may be dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

In addition, stabilizers, such as low-temperature stabilizers, preservatives, antioxidants, light stabilizers or other agents which improve chemical and/or physical stability, may be present. In addition, foam formers or defoamers may be present.

Moreover, the formulations and use forms derived therefrom may comprise, as additional auxiliaries, also stickers such as carboxymethyl cellulose, natural and synthetic pulverulent, particulate or latex-type polymers, such as gum arabic, polyvinyl alcohol, polyvinyl acetate and natural phospholipids such as cephalins and lecithins, and synthetic phospholipids. Further auxiliaries may be mineral and vegetable oils.

It is possible if appropriate for still further auxiliaries to be present in the formulations and the use forms derived therefrom. Such additives are, for example, fragrances, protective colloids, binders, adhesives, thickeners, thixotropic agents, penetrants, retention promoters, stabilizers, sequestrants, complexing agents, humectants, spreading agents. In general, the active ingredients can be combined with any solid or liquid additive which is commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of the active ingredients in the cuticle. The method described in the literature (Baur et al., 1997, Pesticide Science 51, 131-152) can be used to determine this property. Examples include alcohol alkoxylates, for example coconut fat ethoxylate (10) or isotridecyl ethoxylate (12), fatty acid esters, for example rapeseed oil methyl ester or soya oil methyl ester, fatty amine alkoxylates, for example tallowamine ethoxylate (15) or ammonium salts and/or phosphonium salts, for example ammonium sulphate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations may vary within wide ranges. The active ingredient concentration for the use forms may typically be between 0.00000001% and 95% by weight of active ingredient, preferably between 0.00001% and 1% by weight, based on the weight of the use form. Application is accomplished in a manner appropriate to the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Mixtures with Insecticides/Acaricides/Nematicides

The active ingredients specified here with their "common names" are known and are described for example in The Pesticide Manual, 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active ingredients with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies tenebrionis, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, Further active ingredients having an unknown or unclear mechanism of action, for example afidopyropen, afoxolaner, azadirachtin, benclothiaz, benzoximate, bifenazate, bromopropylate, chinomethionat, cryolite, cyclaniliprole, cycloxaprid, cyhalodiamide, dicloromezotiaz, dicofol, diflovidazin, flometoquin, fluensulfone, flufenerim, flufenoxystrobin, flufiprole, fluhexafon, fluopyram, fluralaner, fufenozide, guadipyr, heptafluthrin, imidaclothiz, iprodione, meperfluthrin, paichongding, pyflubumide, pyridalyl, pyrifluquinazon, pyriminostrobin, tetramethylfluthrin, tetraniliprole, tetrachlorantraniliprole, tioxazafen, triflumezopyrim and iodomethane; and additionally preparations based on *Bacillus firmus* (1-1582, BioNeem, Votivo), and the following know active compounds: 1-{2-fluoro-4-methyl-5-[(2,2,2-trifluoroethyl) sulphinyl]phenyl}-3-(trifluoromethyl)-1H-1,2,4-triazol-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanon (known from WO2003/106457), 2-chloro-N-[2-{1-[(2E)-3-(4-chlorophenyl)prop-2-en-1-yl] piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl] carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl] carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]

carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 8-chloro-N-[(2-chloro-5-methoxyphenyl)sulphonyl]-6-(trifluoromethyl) imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969), 3-[benzoyl(methyl)amino]-N-[2-brom-4-[1,2,2,2-tetrafluoro-1-(trifluoromethyl)ethyl]-6-(trifluoromethyl) phenyl]-2-fluorobenzamide (known from WO 2010018714), butyl [2-(2,4-dichlorophenyl)-3-oxo-4-oxaspiro[4.5]dec-1-en-1-yl]carbonate (known from CN 102060818), 4-[5-(3,5-dichlorophenyl)-5-(trifluoromethyl)-4H-isoxazol-3-yl]-N—[(Z)-methoxyiminomethyl]-2-methylbenzamide (known from WO2007/026965), 3E)-3-[1-[(6-chloro-3-pyridinyl) methyl]-2-pyridinylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Mixtures with Fungicides

The active ingredients specified herein by their common name are known and described, for example, in the "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) Inhibitors of ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy] phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl] 1H-imidazole-1-carbothioate, (1.65) Pyrisoxazole, (1.66) 2-{[3-(2-chlorophenyl)-2-(2,4-difluorophenyl)oxiran-2-yl] methyl}-2,4-dihydro-3H-1,2,4-triazole-3-thione, (1.67) 1-{ [3-(2-chlorophenyl)-2-(2,4-difluorophenyl)oxiran-2-yl] methyl}-1H-1,2,4-triazol-5-yl thiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel (2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl) oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl] methyl}-1H-1,2,4-triazole, (1.76) 2-[(2S,4S,5S)-1-(2,4-dichlorophenyl)-5-hydroxy-2,6,6-trimethylheptan-4-yl]-2, 4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2, 4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R, 4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl) phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-

(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5- dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazol, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and its salts, (15.041) propamocarb-fosetylate, (15.042) propanosine-sodium, (15.043) pyrimorph, (15.044) pyrrolnitrine, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) Oxathiapiprolin, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulphonohydrazide, (15.071) 5-fluoro-2-[(4- fluorobenzyl)oxy]pyrimidin-4-amine, (15.072) 5-fluoro-2-[(4-methylbenzyl)oxy]pyrimidin-4-amine, (15.073) 5-methyl-6-octyl[1,2,4]triazolo[1,5-a]pyrimidin-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl- 1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, especially strain ATCC 74040, *Coniothyrium minitans*, especially strain CON/M/91-8 (Accession No. DSM-9660), *Lecanicillium* spp., especially strain HRO LEC 12, *Lecanicillium lecanii*, (formerly known as *Verticillium lecanii*), especially strain KV01, *Metarhizium anisopliae*, especially strain F52 (DSM3884/ATCC 90448), *Metschnikowia fructicola*, especially strain NRRL Y-30752, *Paecilomyces fumosoroseus* (now: *Isaria fumosorosea*), especially strain IFPC 200613, or strain Apopka 97 (Accession No. ATCC 20874), *Paecilomyces lilacinus*, especially *P. lilacinus* strain 251 (AGAL 89/030550), *Talaromyces flavus*, especially strain V117b, *Trichoderma atroviride*, especially strain $SC_1$ (Accession Number CBS 122089), *Trichoderma harzianum*, especially *T. harzianum* rifai T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are: *Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), Pyrethrum/Pyrethrins, *Quassia amara*, Quercus, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Parts of Plants

All plants and plant parts can be treated in accordance with the invention. Plants are understood here to mean all plants and plant populations such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

The inventive treatment of the plants and parts of plants with the active ingredients is effected directly or by action on their surroundings, habitat or storage space by the customary treatment methods, for example by dipping, spraying, atomizing, fogging, broadcasting, spreading-on, injecting and, in the case of propagation material, especially in the case of seeds, also by coating with one or more coats.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

Depending on the plant species or plant cultivars, and the location and growth conditions (soils, climate, vegetation period, diet) thereof, the inventive treatment may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya beans, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya beans, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of Bt plants include maize varieties, cotton varieties, soya bean varieties and potato varieties that are sold under the commercial names YIELD GARD® (e.g. maize, cotton, soya beans), KnockOut® (e.g. maize), StarLink® (e.g. maize), Bollgard® (cotton), Nucotn® (cotton) and NewLeaf® (potatoes). Examples of herbicide-tolerant plants include maize varieties, cotton varieties and soya bean varieties which are sold under the commercial names Roundup Ready® (tolerance to glyphosate e.g. maize, cotton, soya beans), Liberty Link® (tolerance to phosphinothricin, e.g. oilseed rape), IMI® (tolerance to imidazolinones) and STS® (tolerance to sulphonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the inventive active ingredient mixtures. The areas of preference stated above for the active ingredients or mixtures also apply to the treatment of these plants. Particular emphasis is given to the treatment of plants with the compounds or mixtures specifically mentioned in the present text.

Transgenic Plants, Seed Treatment and Integration Events

The transgenic plants or plant cultivars (obtained by genetic engineering) which are to be treated with preference in accordance with the invention include all plants which, by virtue of the genetic modification, received genetic material which imparts particularly advantageous, useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the inventive compounds of the formula (I) is effected directly or by action on their surroundings, habitat or storage space by the customary treatment methods, for example by dipping, spraying, atomizing, irrigating, evaporating, dusting, fogging, broadcasting, foaming, painting, spreading-on, injecting, watering (drenching), drip irrigating and, in the case of propagation material, especially in the case of seed, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

One preferred direct treatment of the plants is foliar application, meaning that inventive compounds of the formula (I) are applied to the foliage, and the frequency of treatment and the application rate may be adjusted for the infestation pressure of the particular pathogen, pest or weed.

In the case of systemically active compounds, the inventive compounds of the formula (I) also get into the plants via the root system. The plants are then treated by the action of the inventive compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the inventive compounds of the formula (I), or by soil application, meaning that the inventive compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvement. Nevertheless, the treatment of seed gives rise to a series of problems which cannot always be solved in a satisfactory manner. Thus, it is desirable to develop methods for protecting the seed and the germinating plant which dispense with, or at least reduce considerably, the additional application of crop protection compositions during storage, after sowing or after emergence of the plants. It is additionally desirable to optimize the amount of active ingredient used so as to provide optimum protection for the seed and the germinating plant from attack by animal pests, but without damage to the plant itself by the active ingredient used. More particularly, methods for the treatment of seed should also take account of the intrinsic insecticidal or nematicidal properties of pest-resistant or tolerant transgenic plants, in order to achieve optimum protection of the seed and of the germinating plant with minimum expenditure of crop protection products.

The present invention therefore also relates, more particularly, to a method for protection of seed and germinating plants from attack by pests, by treating the seed with an inventive compound of the formula (I). The inventive method for protecting seed and germinating plants against attack by pests comprises a method in which the seed is treated simultaneously in one operation or sequentially with an active ingredient of the formula I and mixing components. It also comprises a method in which the seed is treated at different times with an active ingredient of the formula (I) and a mixing component.

The invention likewise relates to the use of the inventive compounds of the formula (I) for treatment of seed for protection of the seed and the resulting plant from animal pests.

The invention further relates to seed which has been treated with an inventive compound of the formula (I) for protection from animal pests. The invention further relates to seed which has been treated simultaneously with an active ingredient of the formula (I) and mixing components. The invention further relates to seed which has been treated at different times with an active ingredient of the formula (I) and mixing components. In the case of seed which has been treated at different times with an active ingredient of the formula (I) and a mixing component, the individual active ingredients in the inventive composition may be present on the seed in different layers. In this case, the layers comprising an active ingredient of the formula (I) and mixing components may optionally be separated by an intermediate layer. The invention also relates to seed in which an active ingredient of the formula (I) and mixing components have been applied as part of a coating or as a further layer or further layers in addition to a coating.

The invention further relates to seed which, after the treatment with the inventive compound of the formula (I), is subjected to a film-coating process to prevent dust abrasion on the seed.

One of the advantages of the present invention is that the particular systemic properties of the inventive compositions mean that treatment of the seed with these compositions protects not only the seed itself but also the resulting plants after emergence from animal pests. In this way, the immediate treatment of the crop at the time of sowing or shortly thereafter can be dispensed with.

A further advantage is that the treatment of the seed with the inventive compound of the formula (I) can enhance germination and emergence of the treated seed.

It is likewise considered to be advantageous that inventive compounds of the formula (I) can especially also be used for transgenic seed.

It should also be mentioned that inventive compounds of the formula (I) can be used in combination with signalling technology compositions, which results, by way of example, in better colonization by symbionts, for example rhizobia, mycorrhizae and/or endophytic bacteria or fungi, and/or in optimized nitrogen fixation.

The inventive compositions are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with an inventive compound of the formula (I) is also of particular significance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the inventive compound of the formula (I) is applied to the seed alone or in a suitable formulation. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming.

In general, in the treatment of the seed, it has to be ensured that the amount of the inventive composition and/or further additives applied to the seed is chosen such that the germination of the seed is not impaired and the plant which arises therefrom is not damaged. This has to be ensured particularly in the case of active ingredients which can exhibit phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. Nos. 4,808,430 A, 5,876,739 A, US 2003/0176428 A1, WO 2002/080675 A1, WO 2002/028186 A2.

The compounds of the formula (I) for use in accordance with the invention can be converted to the customary seed dressing formulations, such as solutions, emulsions, suspensions, powders, foams, slurries or other coating compositions for seed, and also ULV formulations.

These formulations are produced in a known manner, by mixing the compounds of the formula (I) with customary additives, for example customary extenders and solvents or diluents, dyes, wetters, dispersants, emulsifiers, antifoams, preservatives, secondary thickeners, stickers, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetters which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute preparations thereof, can also be used to dress seed of transgenic plants. In this case, additional synergistic effects can also occur in interaction with the substances formed by expression.

For the treatment of seed with the seed dressing formulations usable in accordance with the invention or with the preparations prepared therefrom by addition of water, useful equipment is all mixing units usable customarily for seed dressing. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the inventive compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health sector, i.e. in the field of veterinary medicine, the active ingredients according to the present invention act against animal parasites, especially ectoparasites or else, in a further embodiment, endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acarids such as ticks, for example hard ticks or soft ticks, or mites such as scab mites, harvest mites, bird mites and the like, and also aquatic ectoparasites such as copepods.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of deaths and reductions in performance (in the case of meat, milk, wool, hides, eggs, honey and the like), such that more economical and simpler animal keeping is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

These parasites include:

From the order of the Anoplurida, for example, *Haematopinus* spp., *Linognathus* spp., *Pediculus* spp., *Phthirus* spp., *Solenopotes* spp.; specific examples are: *Linognathus setosus, Linognathus vituli, Linognathus ovillus, Linognathus oviformis, Linognathus pedalis, Linognathus stenopsis,*

*Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus (Boophilus)* spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

From the subclass of the copepods with the order of the Siphonostomatoida in particular the genera *Lepeophtheirus* and *Caligus*; the species *Lepeophtheirus salmonis, Caligus elongatus* and *Caligus clemensi* may be mentioned by way of example and with particular preference.

In general, the inventive active ingredients can be employed directly when they are used for the treatment of animals. They are preferably employed (administered) in the form of pharmaceutical compositions which may comprise pharmaceutically acceptable excipients and/or auxiliaries known in the prior art.

In the sector of animal health and in animal husbandry, the active ingredients are employed (=administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays.

In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC" ]), which contain the active ingredients in an amount of 1% to 80% by weight, directly or after dilution (e.g. 100- to 10 000-fold dilution), or they can be used as a chemical bath.

In the case of use in the animal health sector, the inventive active ingredients, in order to broaden the spectrum of activity, can be used in combination with suitable synergists, repellents or other active ingredients, for example acaricides, insecticides, anthelmintics, anti-protozoal agents. Potential mixing components for inventive compounds of the formula (I) may, in the case of applications in animal health, be one or more compounds from groups (INS-1) to (INS-25).

(INS-1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; particular preference is given here, for applications against ectoparasites, to bendiocarb, carbaryl, methomyl, promacyl and propoxur; or organophosphates, e.g. acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion; particular preference is given here, for applications against ectoparasites, to azamethiphos, chlorfenvinphos, chlorpyrifos, coumaphos, cythioate, diazinon (dimpylate), dichlorvos (DDVP), dicrotophos, dimethoate, ethion (diethion), famphur (famophos), fenitrothion, fenthion (MPP), heptenophos, malathion, naled, phosmet (PMP, phtalofos) phoxim, propetamphos, temephos, tetrachlorvinphos (CVMP) and triclorfon/metrifonate.

(INS-2) GABA-gated chloride channel antagonists, for example organochlorines, e.g. bromocyclene, chlordane and endosulfan (alpha-), heptachlor, lindane and toxaphene; particular preference is given here, for applications against ectoparasites, to endosulphan (alpha-) and lindane; or fiproles (phenylpyrazoles), e.g. acetoprole, ethiprole, fipronil, pyrafluprole, pyriprole, rizazole; particular preference is given here, for applications against ectoparasites, to fipronil and pyriprole; or arylisoxazolines, arylpyrrolines, arylpyrrolidines, e.g. fluralaner (known from WO2009/2024541, ex. 11-1; but also compounds from WO2012007426, WO2012042006, WO2012042007, WO2012107533, WO2012120135, WO2012165186, WO2012155676, WO2012017359, WO2012127347, WO2012038851, WO2012120399, WO2012156400, WO2012163959, WO2011161130, WO2011073444, WO2011092287, WO2011075591, WO2011157748, WO 2007/075459, WO 2007/125984, WO 2005/085216, WO 2009/002809), afoxolaner (e.g. in WO2011149749) and structurally related arylpyrrolines (known, for example, from WO2009/072621, WO 2010020522, WO 2009112275, WO 2009097992, WO 2009072621, JP 2008133273, JP 2007091708), or arylpyrrolidines (e.g. in WO2012004326, WO2012035011, WO2012045700, WO 2010090344, WO 2010043315, WO 2008128711, JP 2008110971), and compounds from the group of the so-called metadiamides (known, for example, from WO2012020483, WO2012020484, WO2012077221, WO2012069366, WO2012175474, WO2011095462, WO2011113756, WO2011093415, WO2005073165); particular preference is given here, for applications against ectoparasites, to afoxolaner and fluaralaner.

(INS-3) Sodium channel modulators/voltage-gated sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans isomer], deltamethrin, dimefluthrin, empenthrin [(EZ)-(1R) isomer], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans isomer], prallethrin, profluthrin, pyrethrins (pyrethrum), resmethrin, RU 15525, silafluofen, tefluthrin, tetramethrin [(1R) isomer)], tralomethrin, transfluthrin and ZXI 8901; particular preference is given here, for applications against ectoparasites, to the type I pyrethroids allethrin, bioallethrin, permethrin, phenothrin, resmethrin, tetramethrin and the type II pyrethroids (alphacyanopyrethroids) alpha-cypermethrin, cyfluthrin (beta-), cyhalothrin (lambda-), cypermethrin (alpha-, zeta-), deltamethrin, fenvalerate, flucythrinate, flumethrin, fluvalinate (tau-), and the ester-free pyrethroids etofenprox and silafluofen; or organochlorine compounds, e.g. DDT or methoxychlor. Active ingredients from this class are very particularly suitable as mixing components, since they have a longer-lasting contact-repelling action and therefore extend the activity spectrum to include this component.

(INS-4) Nicotinergic acetylcholine receptor agonists, for example neonicotinoids, e.g. acetamiprid, clothianidin, dinotefuran, imidacloprid, imidaclothin, nitenpyram, thiacloprid, thiamethoxam; particular preference is given here, for applications against ectoparasites, to chlothianidin, dinotefuran, imidacloprid, nitenpyram and thiacloprid; or nicotine.

(INS-5) Allosteric acetylcholine receptor modulators (agonists), for example spinosyns, e.g. spinetoram and spinosad; particular preference is given here, for applications against ectoparasites, to spinosad and spinetoram.

(INS-6) Chloride channel activators, for example avermectins/milbemycins, e.g. abamectin, doramectin, emamectin benzoate, eprinomectin, ivermectin, latidectin, lepimectin, milbemycin oxime, milbemectin, moxidectin and selamectin; indole terpenoids, for example nodulisporic acid derivatives, especially nodulisporic acid A; particular preference is given here, for applications against ectoparasites, to doramectin, eprinomectin, ivermectin, milbemycin oxime, moxidectin, selamectin and nodulisporic acid A.

(INS-7) Juvenile hormone analogues, for example hydroprene (S—), kinoprene, methoprene (S—); or fenoxycarb; pyriproxyfen; particular preference is given here, for applications against ectoparasites, to methoprene (S—) and pyriproxyfen.

(INS-8) Mite growth inhibitors, e.g. clofentezine, diflovidazin, hexythiazox, etoxazole; particular preference is given here, for applications against ectoparasites, to etoxazole.

(INS-9) Slo-1 and latrophilin receptor agonists, for example cyclic depsipeptides, e.g. emodepside and its precursor PF1022A (known from EP 382173, compound I); particular preference is given here, for applications against ectoparasites, to emodepside.

(INS-10) Oxidative phosphorylation inhibitors, ATP disruptors, for example diafenthiuron.

(INS-12) Nicotinergic acetylcholine receptor antagonists, for example bensultap, cartap (hydrochloride), thiocylam, and thiosultap (sodium).

(INS-13) Chitin biosynthesis inhibitors, type 0, for example benzoylureas, e.g. bistrifluron, chlorfluazuron, diflubenzuron, flucycloxuron, flufenoxuron, hexaflumuron, lufenuron, novaluron, noviflumuron, teflubenzuron and triflumuron; particular preference is given here, for applications against ectoparasites, to diflubenzuron, fluazuron, lufenuron and triflumuron.

(INS-14) Chitin biosynthesis inhibitors, type 1, for example buprofezin.

(INS-15) Moulting inhibitors, for example cyromazine and dicyclanil; particular preference is given here, for applications against ectoparasites, to cyromazine and dicyclanil.

(INS-16) Ecdysone agonists/disruptors, for example diacylhydrazines, e.g. chromafenozide, halofenozide, methoxyfenozide and tebufenozide.

(INS-17) Octopaminergic agonists, for example amitraz, cymiazole, chlordimeform and demiditraz; particular preference is given here, for applications against ectoparasites, to amitraz, cymiazole and demiditraz.

(INS-18) Complex-III electron transport inhibitors, for example hydramethylnone; acequinocyl; fluacrypyrim.

(INS-19) Complex-I electron transport inhibitors, for example from the group of the METI acaricides, e.g. fenazaquin, fenpyroximate, pyrimidifen, pyridaben, tebufenpyrad, tolfenpyrad; particular preference is given here, for applications against ectoparasites, to fenpyroximate, pyrimidifen and tolfenpyrad.

(INS-20) Voltage-gated sodium channel blockers, for example indoxacarb and metaflumizone; particular preference is given here, for applications against ectoparasites, to indoxacarb and metaflumizone.

(INS-21) Inhibitors of acetyl-CoA carboxylase, for example tetronic acid derivatives, e.g. spirodiclofen and spiromesifen; or tetramic acid derivatives, e.g. spirotetramat.

(INS-22) Complex-II electron transport inhibitors, for example cyenopyrafen.

(In-23) Ryanodine receptor effectors, for example diamides, e.g. flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677), and also 1-(3-chloropyridin-2-yl)-N-[4-cyano-2-methyl-6-(methylcarbamoyl)phenyl]-3-[[5-(trifluoromethyl)-2H-tetrazol-2-yl]methyl]-1H-pyrazole-5-carboxamide (CAS No. 1229654-66-2-mixtures may contain also 1-(3-chloro-2-pyridinyl)-N-[4-cyano-2-methyl-6-[(methylamino)carbonyl]phenyl]-3-[[5-(trifluoromethyl)-1H-tetrazol-1-yl]methyl]-1H-pyrazole-5-carboxamide, CAS No. 1229656-17-0).

(INS-24) Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and additionally preparations based on *Bacillus firmus* (1-1582, BioNeem, Votivo) and the following known active compounds: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134), [(6-trifluoromethylpyridin-3-yl)methyl](methyl)oxido-$\lambda^4$-sulphanylidenecyanamide (known from WO 2007/095229), sulfoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazol-5-amine (known from WO 2006/043635), (3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a, 12,12a,12b-decahydro-2H, 11H-benzo[f]pyrano[4,3-b]chromen-4-yl]methyl cyclopropanecarboxylate (known from WO 2006/129714), 2-cyano-3-(difluoromethoxy)-N-ethyl-benzenesulphonamide (known from WO 2005/035486), N-[1-(2,3-dimethylphenyl)-2-(3,5-dimethylphenyl)ethyl]-4,5-dihydro-2-thiazolamine (known from WO 2008/104503); penigequinolone A (known from EP 2248422 (compound I) and WO 2009/060015 (compound No. 11).

(INS-25) Suitable synergists in the case of use together with ectoparasiticides here include MGK264 (N-octylbicycloheptenecarboxamide), piperonyl butoxide (PBO) and verbutin; particular preference is given here to piperonyl butoxide and MGK264.

In addition to these groups, it is also possible to use short-term repellents in mixtures or a combined application. Examples are DEET (N,N-diethyl-3-methylbenzamide), icaridin (1-piperidinecarboxylic acid), (1S,2OS)-2-methylpiperidinyl-3-cyclohexene-1-carboxamide (SS220), indalone (butyl 3,4-dihydro-2,2-dimethyl-4-oxo-2H-pyran-6-carboxylate), dihydronepetalactones, nootkatone, IR3535 (3-[N-butyl-N-acetyl]-aminopropionic acid ethyl ester), 2-ethylhexane-1,3-diol, (1R,2R,5R)-2-(2-hydroxypropan-2-yl)-5-methyl-cyclohexan-1-ol, dimethyl benzene-1,2-dicarboxylate, dodecanoic acid, undecan-2-one, N,N-diethyl-2-phenylacetamide and essential oils or other plant ingredients with known repellent action, for example borneol, callicarpenal, 1,8-cineol (eucalyptol), carvacrol, β-citronellol, α-copaene, coumarin (or its synthetic derivatives known from US20120329832). Icaridin, indalone and IR3535 (3-[N-butyl-N-acetyl]-aminopropionic acid ethyl ester) are particularly preferred for use against ectoparasites.

From the aforementioned groups (INS-1) to (INS-25), preference is given to the following groups as mixing components: (INS-2), (INS-3), (INS-4), (INS-5), (INS-6), (INS-17), (INS-25).

Particularly preferred examples of insecticidally or acaricidally active compounds, synergists or repellents as mixing components for the inventive compounds of the formula (I) are afoxolaner, allethrin, amitraz, bioallethrin, chlothianidin, cyfluthrin (beta-), cyhalothrin (lambda-), cymiazole, cypermethrin (alpha-, zeta-), cyphenothrin, deltamethrin, demiditraz, dinotefuran, doramectin, eprinomectin, etofenprox, fenvalerate, fipronil, fluazuron, flucythrinate, flumethrin, fluralaner, fluvalinate (tau-), icaridin, imidacloprid, ivermectin, MGK264, milbemycin oxime, moxidectin, nitenpyram, permethrin, phenothrin, piperonyl butoxide, pyriprole, resmethrin, selamectin, silafluofen, spinetoram, spinosad, tetramethrin, thiacloprid.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, epidemic typhus, borreliosis;
6) Ticks: borrelioses such as *Borrelia duttoni*, tick-borne encephalitis, Q fever (*Coxiella burnetii*), babesioses (*Babesia canis canis*).

Examples of vectors in the context of the present invention are insects, for example aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of inventive compounds for vector control, for example in agriculture, in horticulture, in forestry, in gardens and in leisure facilities, and also in the protection of materials and stored products.

Protection of Industrial Materials

The inventive compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In one embodiment of the invention, the inventive compositions or products also comprise at least one further insecticide and/or at least one fungicide.

In a further embodiment, this inventive composition is a ready-to-use composition, meaning that it can be applied to the appropriate material without any further modifications. Useful further insecticides or fungicides include those mentioned above.

It has also been found that, surprisingly, the inventive active ingredients and compositions can be used to protect objects which come into contact with saltwater or brackish water, especially hulls, screens, nets, buildings, moorings and signalling systems, against fouling. It is equally possible to use the inventive active ingredients and compositions, alone or in combinations with other active ingredients, as antifouling agents.

Control of Animal Pests in the Hygiene Sector

The inventive compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the active ingredients or compositions are used alone or in combination with other active ingredients and/or auxiliaries. They are preferably used in domestic insecticide products. The inventive active ingredients are effective against sensitive and resistant species and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Preparation Processes

The inventive compounds can be prepared by customary methods known to those skilled in the art.

Reaction scheme 1 shows the general preparation process A for the inventive compounds (I-1).

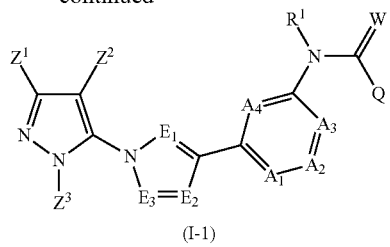

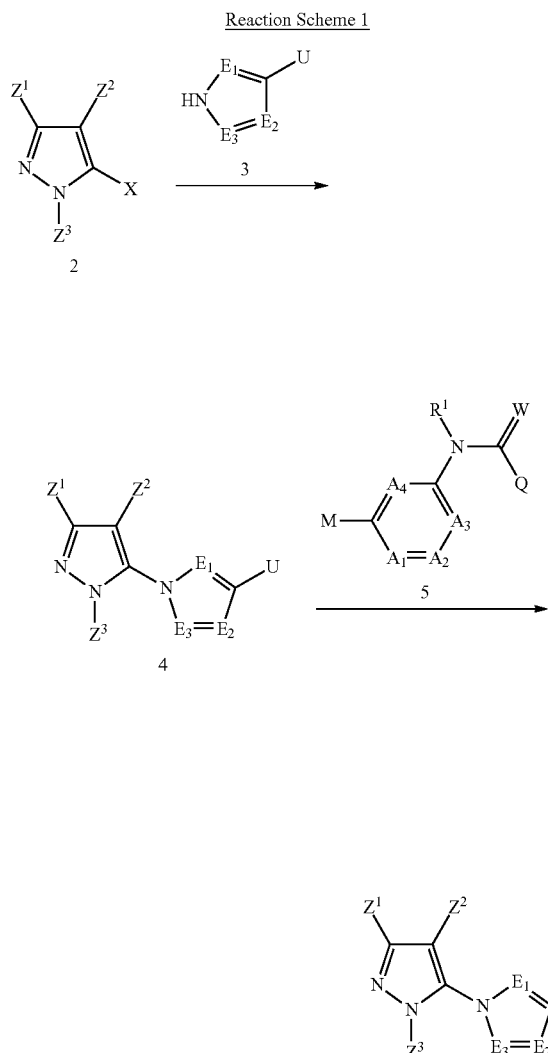

The $A_1$-$A_4$, Q, W, $R^1$ and $Z^1$-$Z^3$ radicals are each as defined above. The five-membered cycles composed of E1-E3, carbon and nitrogen are the 5-membered heterocycles defined under T. X is a halogen. U is bromine, iodine or triflate when M is a boronic acid, boronic ester or trifluoroboronate. U is a boronic acid, boronic ester or trifluoroboronate when M is bromine, iodine or triflate.

Inventive compounds of the general structure (I-1) can be prepared by methods known from the literature, by means of palladium-catalysed reactions from the co-reactants 4 and 5 [e.g. WO 2005/040110; WO 2009/089508]. The compounds of the general structure 5 are either commercially available or can be prepared by processes known to those skilled in the art. The compounds of the general structure 4 can be prepared from the corresponding starting materials 2 and 3 by methods known from literature either by a nucleophilic substitution of the aromatic system (X=chlorine or fluorine) [WO 2007/107470; Tetrahedron Letters 2003, 44, 7629-7632] or by a transition metal-catalysed reaction (X=bromine or iodine) [WO 2012/003405; WO 2009/158371].

Alternatively, the inventive compounds (I-1) can be prepared by the general preparation process B (Reaction Scheme 2).

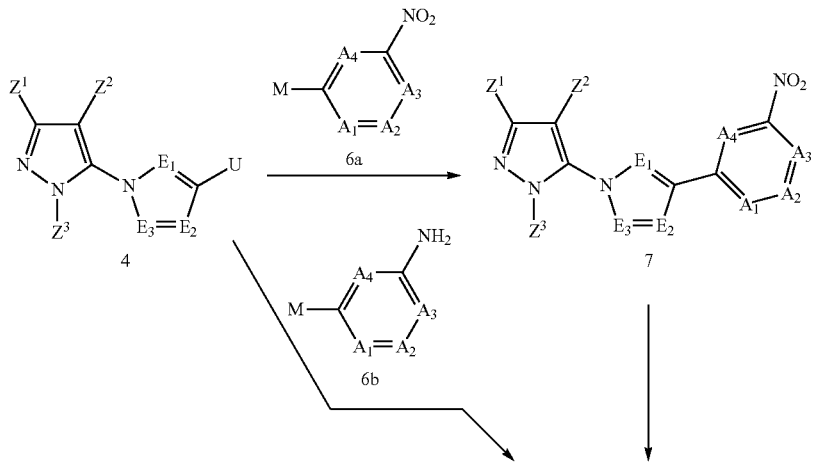

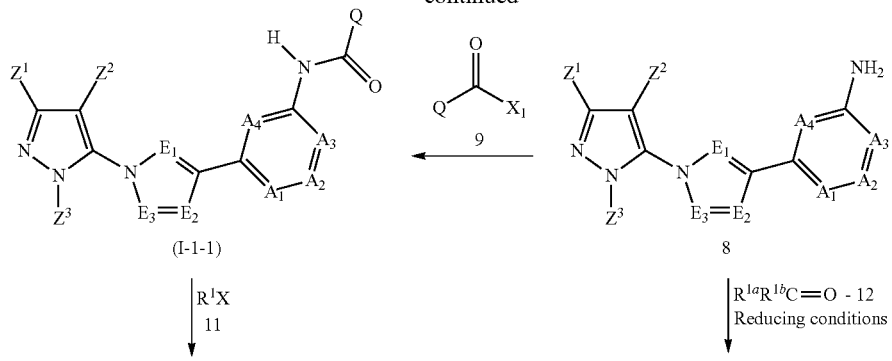

(I-1-1)          8

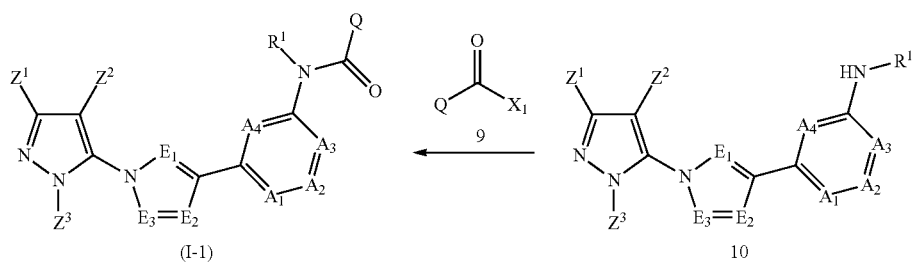

(I-1)          10

The $A_1$-$A_4$, Q, $R^1$ and $Z^1$-$Z^3$ radicals are each as defined above. The five-membered cycles composed of E1-E3, carbon and nitrogen represent the 5-membered heterocycles defined under T. X is a halogen; $X_1$ is halogen or OH. U is bromine, iodine or triflate when M is a boronic acid, boronic ester or trifluoroboronate. U is a boronic acid, boronic ester or trifluoroboronate when M is bromine, iodine or triflate.

Inventive compounds of the general structure (I-1) and (I-1-1) can be prepared in analogy to peptide coupling methods known from the literature from the starting materials 8 or 10 reacted with 9 [e.g. WO 2010/051926 or WO 2010/133312]. Compounds of the general structure 8 can be prepared in analogy to methods known from literature by reduction from compounds of the general structure 7 [WO 2012/080376] or by a direct coupling route from the general structure 4. Compounds of the general structure 7 can be prepared in analogy to methods known from literature by means of palladium catalysed reactions [WO 2005/040110; WO 2009/089508]. Inventive compounds of the general structure (I-1) can be produced by alkylation reactions, which are sufficiently well known to those skilled in the art, of amides of the structure (I-1-1) with alkylating reagents 11, preferably in the presence of basic reaction auxiliaries. Alternatively, under reductive conditions, intermediates of the general structure 8 can be reacted with suitably substituted ($R^{1a}$, $R^{1b}$) ketones or aldehydes 12 to give compounds of the general structure 10 [WO 2012/080376], in order subsequently to obtain the inventive compounds of the general structure (I-1) in analogy to peptide coupling methods known from the literature [WO 2012/080376].

Inventive compounds of the general structure (I-2) can be synthesized by preparation process C shown in Reaction Scheme 3.

Reaction Scheme 3

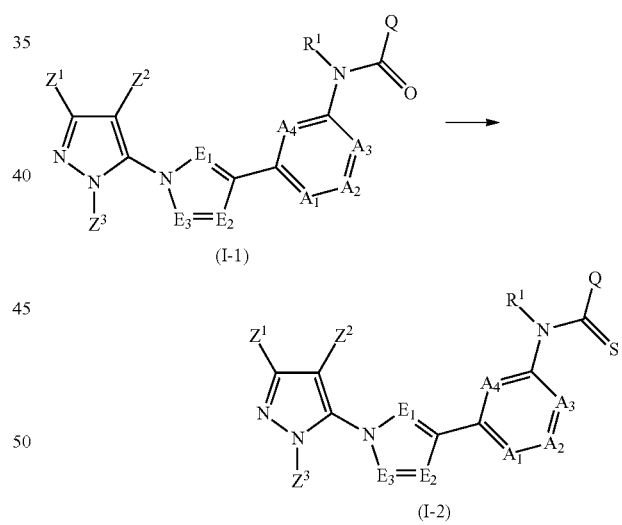

The $A_1$-$A_4$, Q, $R^1$ and $Z^1$-$Z^3$ radicals are each as defined above. The five-membered cycles composed of E1-E3, carbon and nitrogen represent the 5-membered heterocycles defined under T.

Inventive compounds of the general structure (I-2) can be prepared in analogy to processes known from the literature from compounds of the general structure (I-1) [WO 2012/056372; WO 2003/066050].

The compounds of the general structure 2 are either commercially available or can be prepared by processes known to those skilled in the art or in analogy to these processes [WO 2010/051926; WO 2011/131615; WO 2006/018725; WO 2012/065932; WO 2007/077961; US2012-

0115903; WO 2010/017902; WO 2010/127856; Tetrahedron Letters 2011, 44, 8451-8457].

The compounds of the general structure 3 are either commercially available or can be prepared by processes known to those skilled in the art or in analogy to these processes [WO2009/155527; WO2007/138072].

The compounds of the general structure 5 are either commercially available or can be prepared by processes known to those skilled in the art or in analogy to these processes [WO 2005/041904].

The compounds of the general structure 6 are either commercially available or can be prepared by processes known to those skilled in the art or in analogy to these processes [Journal of Organic Chemistry 2013, 78(5), 1923-1933].

Reaction Scheme 4 shows the general preparation process D for the inventive compounds (Ih).

pounds (Ih) can be synthesized directly from the acetylenes 14 with appropriate (het)aryl azides 15 in the course of a [3+2] cycloaddition.

Oxidizing agents for the oxidation of alcoholic groups are known (cf., for example, oxidation reagents in Organic Synthesis by Oxidation with Metal Compounds, Mijs, de Jonge, Plenum Verlag, New York, 1986; Manganese Compounds as Oxidizing Agens in Organic Chemistry, Arndt, Open Court Publishing Company, La Salle, Ill., 1981; The Oxidation of Organic Compounds by Permanganate Ion and Hexavalent Chromium, Lee, Open Court Publishing Company, La Salle, Ill., 1980). An oxidation can be conducted, for example, in the presence of permanganates (e.g. potassium permanganate), metal oxides (e.g. manganese dioxide, chromium oxides, which are used, for example, in dipyridinechromium(VI) oxide as Collins reagent (cf. J. C. Collins et al., Tetrahedron Lett. 30, 3363-3366, 1968). Likewise in

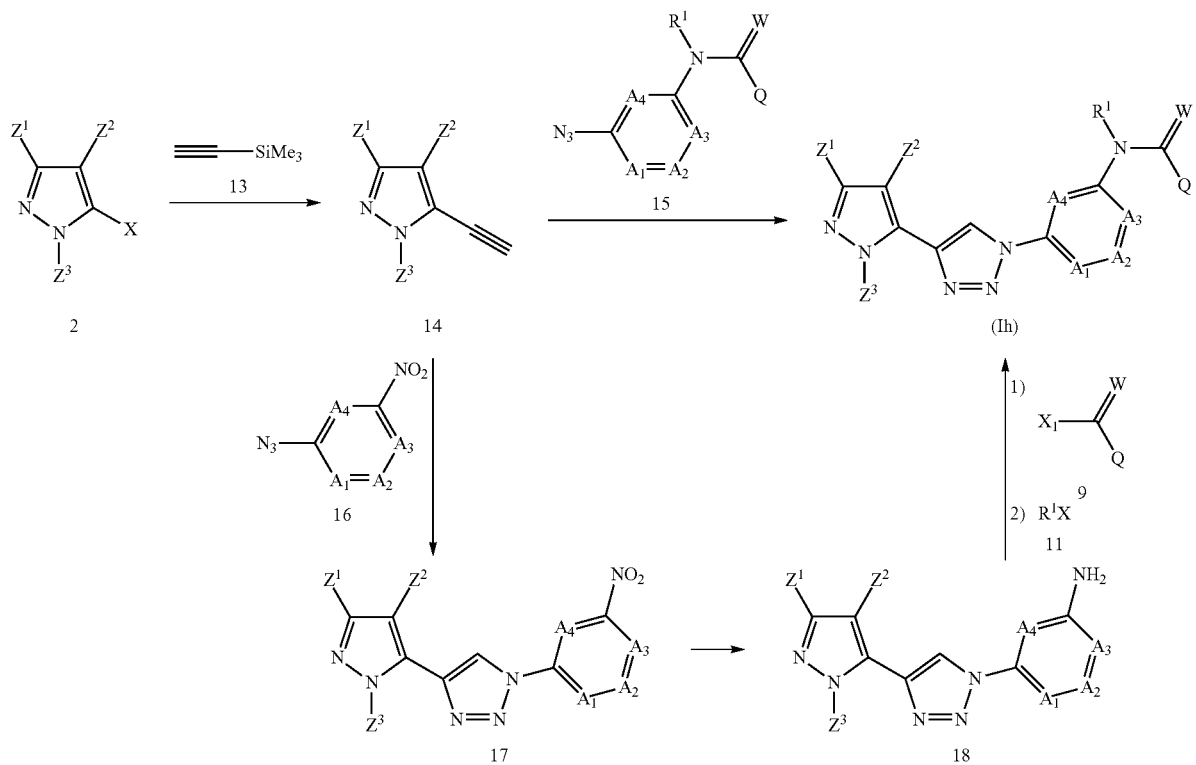

Reaction Scheme 4

The $Z^1$, $Z^2$, $Z^3$, $A^1$, $A^2$, $A^3$, $A^4$ radicals in the abovementioned formulae 2, 14, 15, 16, 17 and 18 are each as defined above in general terms by the radical definitions for the general formula (Ih) or the general formula (I); this applies especially to the preferred or particularly preferred radical definitions of the formula (Ih).

Proceeding from pyrazoles having the leaving group X=halogen or X=mesylate (2), it is possible to prepare corresponding pyrazoleacetylenes 14 [US2011/275628 A], optionally with transition metal catalysis.

Compounds of the general structure 17 are synthesized by a [3+2] cycloaddition of the acetylenes 14 with appropriate (het)aryl azides 16 [analogously to Tetrahedron Letters, 2006, 47, (19) 3209-3212] and are then subsequently reduced to the amines/anilines 18 or converted to the inventive compounds (Ih). Alternatively, the inventive comthe presence of pyridinium chlorochromate (e.g. Corey's reagent) (cf. also R. O. Hutchins et al., Tetrahedron Lett. 48, 4167-4170, 1977; D. Landini et al. Synthesis 134-136, 1979) or ruthenium tetroxide (cf. S.-I. Murahashi, N. Komiya Ruthenium-catalyzed Oxidation of Alkenes, Alcohols, Amines, Amides, β-Lactams, Phenols and Hydrocarbons, in: Modern Oxidation Methods, Baeckvall, Jan-Erling (Eds.), Wiley-VCH-Verlag GmbH & Co. KGaA, 2004). Likewise suitable are ultrasound-induced oxidation reactions, and the use of potassium permanganate (cf. J. Yamawaki et al., Chem. Lett. 3, 379-380, 1983).

For deblocking/detachment of protecting groups (PG), it is possible to use any known suitable acidic or basic reaction auxiliaries by the procedures described in the literature. When protecting groups of the carbamate type are used for amino groups, preference is given to using acidic reaction auxiliaries. When the t-butylcarbamate protecting group (BOC group) is used, for example, mixtures of mineral acids such as hydrochloric acid, hydrobromic acid, nitric acid, sulphuric acid, phosphoric acid, or organic acids such as benzoic acid, formic acid, acetic acid, trifluoroacetic acid, methanesulphonic acid, benzenesulphonic acid or toluenesulphonic acid, and a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

It is known that some reactions and preparation processes are performable particularly efficiently in the presence of diluents or solvents and basic or acidic reaction auxiliaries. It is likewise possible to use mixtures of the diluents and solvents. The diluents and solvents are advantageously used in such an amount that the reaction mixture has good stirrability over the entire process.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Basic reaction auxiliaries used for performance of the processes according to the invention may be any suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

Acidic reaction auxiliaries used for performance of the processes according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(V) chloride, tin(V) chloride, and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

If protecting groups are envisaged in the reaction schemes, it is possible to use any commonly known protecting groups. Especially those which are described by Greene T. W., Wuts P. G. W. in Protective Groups in Organic Synthesis; John Wiley & Sons, Inc. 1999, "Protection for the hydroxyl group including 1,2- and 1,3-diols".

Further suitable protecting groups are also of the substituted methyl ether type (e.g. methoxymethyl ether (MOM), methylthiomethyl ether (MTM), (phenyldimethylsilyl)methoxymethyl ether (SNOM-OR), benzyloxymethyl ether (BOM-OR), para-methoxybenzyloxymethyl ether (PMBM-OR), para-nitrobenzyloxymethyl-ether, ortho-nitrobenzyloxymethyl ether (NBOM-OR), (4-methoxyphenoxy)methyl ether (p-AOM-OR), guaiacolmethyl ether (GUM-OR), t-butoxymethyl ether, 4-pentyloxymethyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR), methoxymethyl ether (MM-OR));

of the substituted ethyl ether type (e.g. 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluoroethyl ether (MIP-OR), 1-methyl-1-phenoxyethyl ether, 2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether, 2-(phenylselenyl)ethyl ether), of an ether (e.g. tetrahydropyranyl ether (THP-OR), 3-bromotetrahydropyranyl ether (3-BrTHP-OR), tetrahydrothiopyranyl ether, 1-methoxycyclohexyl ether, 2- and 4-picolyl ether, 3-methyl-2-picolyl-N-oxido ether, 2-quinolinylmethyl ether (Qm-OR), 1-pyrenylmethyl ether, diphenylmethyl ether (DPM-OR), para, para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl)phenylmethyl ether (DMTr-OR), tri(para-methoxyphenyl)phenylmethyl ether (TMTr-OR), 4-(4'-bromophenacyloxy) phenyldiphenylmethyl ether, 4,4',4''-tris(4,5-dichlorophthalimidophenyl)methyl ether (CPTr-OR), 4,4',4''-tris(benzoyloxyphenyl)methyl ether (TBTr-OR), 4,4'-dimethoxy-3''-[N-(imidazolylmethyl)]trityl ether (IDTr-OR), 4,4'-dimethoxy-3''-[N-(imidazolylethyl)carbamoyl]trityl ether (IETr-OR), 1,1-bis(4-methoxyphenyl)-1'-pyrenylmethyl ether (Bmpm-OR), 9-anthryl ether, 9-(9-phenyl)xanthenyl ether (pixyl-OR), 9-(9-phenyl-10-oxo)anthryl (tritylone ether), 4-methoxytetrahydropyranyl ether (MTHP-OR), 4-methoxytetrahydrothiopyranyl ether, 4-methoxy-tetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8,8-trimethyl-4,7-methanbenzofuran-2-yl ether (MBF-OR), t-butyl ether, allyl ether, propargyl ether, para-chlorophenyl ether, para-methoxyphenyl ether, para-nitrophenyl ether, para-2,4-dinitrophenyl ether (DNP-OR), 2,3,5,6-tetrafluoro-4-(trifluormethyl)phenyl ether, benzyl ether (Bn-OR));

of the substituted benzyl ether type (e.g. para-methoxybenzyl ether (MPM-OR), 3,4-dimethoxybenzyl ether (DMPM-OR), ortho-nitrobenzyl ether, para-nitrobenzyl ether, para-halobenzyl ether, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, para-(methylsulphinyl)benzyl ether (Msib-OR));

of the silyl ether type (e.g. trimethylsilyl ether (TMS-OR), triethylsilyl ether (TES-OR), triisopropylsilyl ether (TIPS-OR), dimethylisopropylsilyl ether (IPDMS-OR), diethylisopropylsilyl ether (DEIPS-OR), dimethylhexylsilyl ether (TDS-OR), t-Butyldimethylsilyl ether (TBDMS-OR), t-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-t-butylmethylsilyl ether (DTBMS-OR), tris(trimethylsilyl)silyl ether (sisyl ether), di-t-butylmethylsilyl ether (DTBMS-OR), tris(trimethylsilyl)silyl ether (sisyl ether), (2-hydroxystyryl)dimethylsilyl ether (HSDMS-OR), (2-hydroxystyryl)diisopropylsilyl ether (HSDIS-OR), t-butylmethoxyphenylsilyl ether (TBMPS-OR), t-butoxydiphenylsilyl ether (DPTBOS-OR));

of the ester type (e.g. formate ester, benzoylformate ester, acetate ester (Ac-OR), chloroacetate ester, dichloroacetate ester, trichloroacetate ester, trifluoroacetate ester, (TFA-OR), methoxyacetate ester, triphenylmethoxyacetate ester, phenoxyacetate ester, para-chlorophenoxyacetate ester, phenylacetate ester, diphenylacetate ester (DPA-OR), nicotinate ester, 3-phenylpropionate ester, 4-pentoate ester, 4-oxopentoate ester (levulinate) (Lev-OR) 4,4-(ethylenedithio)pentanoate ester (LevS-OR), 5-[3-bis(4-methoxyphenyl)hydroxymethoxyphenoxy]levulinate ester, pivaloate ester (Pv-OR), 1-adamantanoate ester, crotonate ester, 4-methoxycrotonate ester, benzoate ester (Bz-OR), para-phenylbenzoate ester, 2,4,6-trimethylbenzoate ester (mesitoate), 4-(methylthiomethoxy)butyrate ester (MTMB-OR), 2-(methylthiomethoxymethyl)benzoate ester (MTMT-OR), of the carbonate type (e.g. methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMS-OR), 2-(phenylsulphonyl)ethyl carbonate (Ps-OR), 2-(triphenylphosphonio) ethyl carbonate (Peoc-OR), t-butyl carbonate (Boc-OR), isobutyl carbonate, vinyl carbonate, allyl carbonate (Alloc-OR), para-nitrophenyl carbonate, benzyl carbonate (Z—OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc)), and of the sulphate type (e.g. allylsulphonate (Als-OR), methanesulphonate (Ms-OR), benzylsulphonate, tosylate (Ts-OR), 2-[(4-nitrophenyl)ethyl]sulphonate (Npes-OR)).

Catalysts suitable for performance of a catalytic hydrogenation in the process according to the invention are all the customary hydrogenation catalysts, for example platinum catalysts (e.g. platinum sheet, platinum sponge, platinum black, colloidal platinum, platinum oxide, platinum wire), palladium catalysts (e.g. palladium sponge, palladium black, palladium oxide, palladium-charcoal, colloidal palladium, palladium barium sulphate, palladium barium carbonate, palladium hydroxide), nickel catalysts (e.g. reduced nickel, nickel oxide, Raney nickel), ruthenium catalysts, cobalt catalysts (e.g. reduced cobalt, Raney cobalt), copper catalysts (e.g. reduced copper, Raney copper, Ullmann copper). Preference is given to using noble metal catalysts (e.g. platinum and palladium or ruthenium catalysts) which have optionally been applied to a suitable support (e.g. carbon or silicon), rhodium catalysts (e.g. tris(triphenylphosphine)rhodium(I) chloride in the presence of triphenylphosphine). In addition, it is possible to use "chiral hydrogenation catalysts" (for example those which contain chiral diphosphine ligands such as (2S,3S)-(−)-2,3-bis(diphenylphosphino)butane [(S,S)-Chiraphos] or (R)-(+)-2,2'- or (S)-(−)-2,2'-bis(diphenylphosphino)-1,1'-binaphthalene [R(+)-BINAP or S(−)-BINAP]), which increases the proportion of one isomer in the isomer mixture or virtually completely prevents the formation of another isomer.

Salts of the inventive compounds are prepared by standard methods. Representative acid addition salts are, for example, those which are formed by reaction with inorganic acids, for example sulphuric acid, hydrochloric acid, hydrobromic acid, phosphoric acid, or organic carboxylic acids such as acetic acid, trifluoroacetic acid, citric acid, succinic acid, butyric acid, lactic acid, formic acid, fumaric acid, maleic acid, malonic acid, camphoric acid, oxalic acid, phthalic acid, propionic acid, glycolic acid, glutaric acid, stearic acid, salicylic acid, sorbic acid, tartaric acid, cinnamic acid, valeric acid, picric acid, benzoic acid, or organic sulphonic acids such as methanesulphonic acid and 4-toluenesulphonic acid.

Also representative are salts of inventive compounds which are formed from organic bases, for example pyridine or triethylamine, or those which are formed from inorganic bases, for example hydrides, hydroxides or carbonates of sodium, lithium, calcium, magnesium or barium, when the compounds of the general formula (I) have a structural element suitable for formation of this salt.

Synthesis methods for preparation of heterocyclic N-oxides and t-amines are known. They can be obtained with peroxy acids (e.g. peracetic acid and meta-chloroperbenzoic acid (MCPBA), hydrogen peroxide), alkyl hydroperoxides (e.g. t-butyl hydroperoxide), sodium perborate and dioxiranes (e.g. dimethyldioxirane). These methods are described, for example, by T. L. Gilchrist, in Comprehensive Organic Synthesis, vol. 7, p. 748-750, 1992, S. V. Ley, (Ed.), Pergamon Press; M. Tisler, B. Stanovnik, in Comprehensive Heterocyclic Chemistry, vol. 3, p. 18-20, 1984, A. J. Boulton, A. McKillop, (Eds.), Pergamon Press; M. R. Grimmett, B. R. T. Keene in Advances in Heterocyclic Chemistry, vol. 43, p. 149-163, 1988, A. R. Katritzky, (Ed.), Academic Press; M. Tisler, B. Stanovnik, in Advances in Heterocyclic Chemistry, vol. p, S. 285-291, 1968, A. R. Katritzky, A. J. Boulton (Eds.), Academic Press; G. W. H. Cheeseman, E. S. G. Werstiuk in Advances in Heterocyclic Chemistry, vol. 22, p. 390-392, 1978, A. R. Katritzky, A. J. Boulton, (Eds.), Academic Press.

PREPARATION EXAMPLES $^1$H NMR Data

The $^1$H NMR data are recorded with a Bruker Avance 400, equipped with a flow cell (volume 60 μl), or with a Bruker AVIII 400, equipped with a 1.7 mm cryo-CPTCI sample head, or with a Bruker AVII 600 (600.13 MHz), equipped with a 5 mm cryo-TCI sample head, or with a Bruker AVIII 600 (601.6 MHz), equipped with a 5 mm cryo-CPMNP sample head. This was done using tetramethylsilane as reference (0.0 ppm) and CD$_3$CN, CDCl$_3$ or D$_6$-DMSO as deuterated solvent.

Synthesis of N-{3-[2'-methyl-5'-(pentafluoroethyl)-4'-(trifluoromethyl)-2'H-1,3'-bipyrazol-4-yl]phenyl}isonicotinamide Stage 1

4-Bromo-2'-methyl-5'-(pentafluoroethyl)-4'-(trifluoromethyl)-2'H-1,3'-bipyrazole

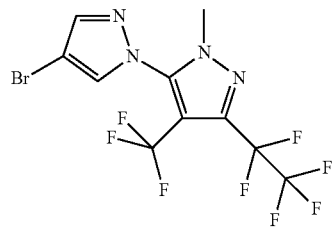 [SMILES: Cn1nc(C(F)(F)C(F)(F)F)c(C(F)(F)F)c1-n1cc(Br)cn1]

8 g (27.9 mmol) of 5-fluoro-1-methyl-3-(pentafluoroethyl)-4-(trifluoromethyl)-1H-pyrazole (Nippon Kagaku Kaishi, 1985, (10), 1995-2000), 4.11 g (27.9 mmol) of 4-bromopyrazole and 7.73 g (55.9 mmol) of potassium carbonate were stirred under reflux in 140 ml of THF for 12 hours. Subsequently, the potassium carbonate was filtered off, the solvent was distilled off on a rotary evaporator and the residue was chromatographed using silica gel (cyclohexane/ethyl acetate gradient). 6.83 g (55.3% of theory) were isolated as a waxy solid.

Stage 2

2'-Methyl-4-(3-nitrophenyl)-5'-(pentafluoroethyl)-4'-(trifluoromethyl)-2'H-1,3'-bipyrazole

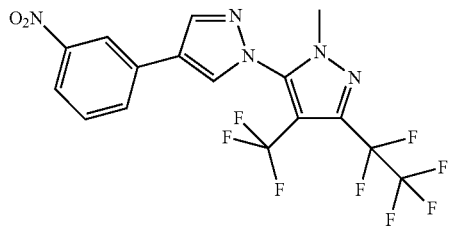 [SMILES: Cn1nc(C(F)(F)C(F)(F)F)c(C(F)(F)F)c1-n1cc(-c2cccc([N+](=O)[O-])c2)cn1]

5.5 g (13.3 mmol) of the bipyrazole from Stage 1 and 2.22 g (13.3 mmol) of 3-nitrophenylboronic acid were initially charged in 110 ml of 1,4-dioxane, and 0.98 g (1.33 mmol) of 1,1'-bis(diphenylphosphino)ferrocenepalladium(II) chloride and 86.5 ml of a 2M aqueous Na$_2$CO$_3$ solution were added. The mixture was stirred at 100° C. until conversion was complete. After the reaction mixture had cooled down, the complete mixture was concentrated on silica gel on a rotary evaporator and then chromatographed using silica gel (cyclohexane/ethyl acetate gradient). 5.21 g (78.4% of theory) were obtained as a colourless solid.

Stage 3

N-{3-[2'-Methyl-5'-(pentafluoroethyl)-4'-(trifluoromethyl)-2'H-1,3'-bipyrazol-4-yl]aniline

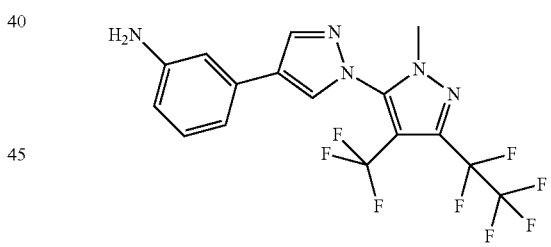

4.9 g (10.7 mmol) of the nitro compound from Stage 2 were dissolved in 36 ml of isopropanol, and 6.3 g (27.9 mmol) of tin(II) chloride dihydrate were added at room temperature. The reaction mixture was cooled to 0° C., then 9 ml of conc. HCl were added dropwise and then the mixture was stirred under reflux for 2 hours. After the reaction had ended, the volume of the reaction mixture was concentrated to two thirds on a rotary evaporator, then 500 ml of water were added and then the aqueous mixture was adjusted to pH 8-9 with 30% NaOH. The aqueous mixture was extracted repeatedly with ethyl acetate, the combined organic phases were dried over magnesium sulphate, filtered and concentrated, and the residue was chromatographed using silica gel (cyclohexane/ethyl acetate gradient). 3.2 g (68.2% of theory) of a yellowish oil were obtained.

Stage 4

N-{3-[2'-Methyl-5'-(pentafluoroethyl)-4'-(trifluoromethyl)-2'H-1,3'-bipyrazol-4-yl]-phenyl}isonicotinamide

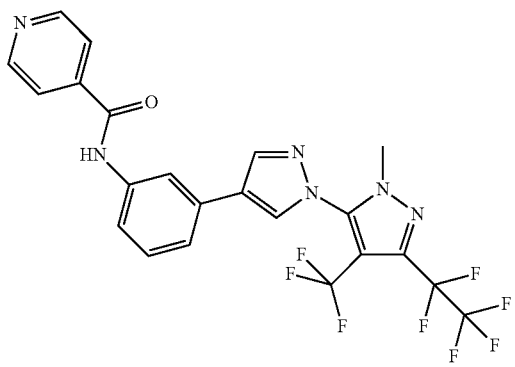 [SMILES: Cn1nc(C(F)(F)C(F)(F)F)c(C(F)(F)F)c1-n1cc(-c2cccc(NC(=O)c3ccncc3)c2)cn1]

300 mg (0.7 mmol) of the aniline from Stage 3 were dissolved in 2 ml of THF, 126 mg (0.7 mmol) of isonicotinyl chloride hydrochloride and 86 mg (0.84 mmol) of triethylamine were added at room temperature, and the mixture was stirred under reflux until conversion was complete, with monitoring by TLC. After cooling, 5 ml of water were added and the mixture was extracted repeatedly with dichloromethane. The combined organic phases were dried over magnesium sulphate, filtered and concentrated, and the residue was chromatographed using silica gel (cyclohexane/ethyl acetate gradient). 300 mg (80.2% of theory) of the target compound were obtained as a yellowish oil.

With the aid of the above-described preparation processes, the compounds listed in Tables 1a, 1b and 2 were prepared.

TABLE 1a (Ic-1)

| Ex. No. | $Z^1$ | $Z^2$ | $Z^3$ | $R^1$ | $R^4$ | $R^5$ | Q |
|---|---|---|---|---|---|---|---|
| 1-001 | $CF_2CF_3$ | $CF_3$ | $CH_3$ | H | H | H | 4-pyridinyl |
| 1-002 | $CF_2CF_3$ | $CF_3$ | $CH_3$ | H | H | H | cyclopropyl |
| 1-003 | $CF_2CF_3$ | $CF_3$ | $CH_3$ | H | H | H | 4-F-phenyl |
| 1-004 | $CF_2CF_3$ | $CF_3$ | $CH_3$ | H | H | H | 3-F-4-pyridinyl |
| 1-005 | $CF_2CF_3$ | $CF_3$ | $CH_3$ | H | H | H | 3-Cl-2-pyridinyl |
| 1-006 | $CF_2CF_3$ | $CF_3$ | $CH_3$ | H | H | H | 2-Cl-4-pyridinyl |
| 1-007 | $CF_2CF_3$ | $CF_3$ | $CH_3$ | H | H | H | $CF_3CH_2$— |
| 1-008 | $CF_2CF_3$ | $CF_3$ | $CH_3$ | H | H | H | ethyl |
| 1-009 | $CF_2CF_3$ | $CF_3$ | $CH_3$ | H | H | H | $CHF_2CF_2$— |
| 1-010 | $CF_2CF_3$ | $CF_3$ | $CH_3$ | H | H | H | phenyl |
| 1-011 | $CF_2CF_3$ | $CF_3$ | $CH_3$ | H | H | H | 2,6-$Cl_2$-4-pyridinyl |
| 1-012 | $CF_2CF_3$ | $CF_3$ | $CH_3$ | H | H | H | 2-F-phenyl |
| 1-013 | $CF_2CF_3$ | $CF_3$ | $CH_3$ | H | H | H | 3-F-phenyl |
| 1-014 | $CF_2CF_3$ | $CF_3$ | $CH_3$ | H | H | H | 3,5-$F_2$-phenyl |
| 1-015 | $CF_2CF_3$ | $CF_3$ | $CH_3$ | H | H | H | 2,6-$F_2$-phenyl |
| 1-016 | $CF_2CF_3$ | $CF_3$ | $CH_3$ | H | H | H | 3-thiophenyl |
| 1-017 | $CF_2CF_3$ | $CF_3$ | $CH_3$ | H | H | H | 2-thiophenyl |
| 1-018 | $CF_2CF_3$ | $CF_3$ | $CH_3$ | H | H | H | 3-Cl-2-thiophenyl |
| 1-019 | $CF_2CF_3$ | $CF_3$ | $CH_3$ | H | H | H | 1-methyl-4-pyrazolyl |
| 1-020 | $CF_2CF_3$ | $CF_3$ | $CH_3$ | H | H | F | 3-Cl-2-pyridinyl |
| 1-021 | $CF_2CF_3$ | $CF_3$ | $CH_3$ | H | Cl | H | 3-Cl-2-pyridinyl |
| 1-022 | $CF_2CF_3$ | $CF_3$ | $CH_3$ | H | Cl | H | 4-F-phenyl |
| 1-023 | $CF_2CF_3$ | $CF_3$ | $CH_3$ | H | Cl | H | phenyl |
| 1-024 | $CF_2CF_3$ | $CF_3$ | $CH_3$ | H | Cl | H | 4-pyridinyl |
| 1-025 | $CF_2CF_3$ | $CF_3$ | $CH_3$ | H | F | H | 4-pyridinyl |
| 1-026 | $CF_2CF_3$ | $CF_3$ | $CH_3$ | H | F | H | phenyl |
| 1-027 | $CF_2CF_3$ | $CF_3$ | $CH_3$ | H | F | H | 4-F-phenyl |
| 1-028 | $CF_2CF_3$ | $CF_3$ | $CH_3$ | H | H | H | 2-Cl-3-pyridinyl |
| 1-029 | $CF_2CF_3$ | $CF_3$ | $CH_3$ | H | H | H | 1-CN-cyclopropyl |
| 1-030 | $CF_2CF_3$ | $CF_3$ | $CH_3$ | H | H | H | 1-Cl-cyclopropyl |
| 1-031 | $CF_2CF_3$ | $CF_3$ | $CH_3$ | H | H | H | 1-oxazolyl |
| 1-032 | $CF_2CF_3$ | $CF_3$ | $CH_3$ | H | F | H | 1-Cl-cyclopropyl |
| 1-033 | $CF_2CF_3$ | $CF_3$ | $CH_3$ | H | F | H | $CHF_2CF_2$— |
| 1-034 | $CF_2CF_3$ | $CF_3$ | $CH_3$ | H | F | H | 4-pyrimidinyl |
| 1-035 | $CF_2CF_3$ | $CF_3$ | $CH_3$ | H | F | H | 1-Me-4-pyrazolyl |
| 1-036 | $CF_2CF_3$ | $CF_3$ | $CH_3$ | H | F | H | 2-pyrimidinyl |
| 1-037 | $CF_2CF_3$ | $CF_3$ | $CH_3$ | CH3 | F | H | 4-F-Phenyl |
| 1-038 | $CF_2CF_3$ | $CF_3$ | $CH_3$ | H | CH3 | H | 4-F-phenyl |
| 1-039 | $CF_2CF_3$ | $CF_3$ | $CH_3$ | H | F | F | 4-F-phenyl |
| 1-040 | $CF_2CF_3$ | $CF_3$ | $CH_3$ | H | CH3 | H | 4-pyridinyl |
| 1-041 | $CF_2CF_3$ | $CF_3$ | $CH_3$ | H | F | H | 3-thiophenyl |
| 1-042 | $CF_2CF_3$ | $CF_3$ | $CH_3$ | H | F | H | 3-MeO-phenyl |
| 1-043 | $CF_2CF_3$ | $CF_3$ | $CH_3$ | H | F | H | 2-Cl-6-Me-4-pyridinyl |
| 1-044 | $CF_2CF_3$ | $CF_3$ | $CH_3$ | H | F | H | 1-Me-3-tBu-4-$NO_2$-5-pyrazolyl |
| 1-045 | $CF_2CF_3$ | $CF_3$ | $CH_3$ | H | F | H | 3-Cl-benzothiophen-2-yl |
| 1-046 | $CF_2CF_3$ | $CF_3$ | $CH_3$ | H | F | H | (1,1-dimethyl)-2-fluoroethyl |
| 1-047 | $CF_2CF_3$ | $CF_3$ | $CH_3$ | H | F | H | cis/trans-4-MeO-cyclohex-1-yl |
| 1-048 | $CF_2CF_3$ | $CF_3$ | $CH_3$ | H | F | H | $MeOCH_2$— |
| 1-049 | $CF_2CF_3$ | $CF_3$ | $CH_3$ | H | F | H | 2-thiophenyl |
| 1-050 | $CF_2CF_3$ | $CF_3$ | $CH_3$ | H | F | H | 3-$CF_3$-4-F-phenyl |
| 1-051 | $CF_2CF_3$ | $CF_3$ | $CH_3$ | H | F | H | 2,6-$(MeO)_2$-phenyl |
| 1-052 | $CF_2CF_3$ | $CF_3$ | $CH_3$ | H | F | H | (rac)-1-methylpropyl |
| 1-053 | $CF_2CF_3$ | $CF_3$ | $CH_3$ | H | F | H | 1-Me-cyclohex-1-yl |
| 1-054 | $CF_2CF_3$ | $CF_3$ | $CH_3$ | H | F | H | 4-$(Me_2N)$-phenyl |
| 1-055 | $CF_2CF_3$ | $CF_3$ | $CH_3$ | H | F | H | cyclopropyl |
| 1-056 | $CF_2CF_3$ | $CF_3$ | $CH_3$ | H | F | H | 2,4,6-$(iPr)_3$-phenyl |
| 1-057 | $CF_2CF_3$ | $CF_3$ | $CH_3$ | H | F | H | 3-$CF_3$-phenyl |
| 1-058 | $CF_2CF_3$ | $CF_3$ | $CH_3$ | H | F | H | 1-Me-cyclopropyl |
| 1-059 | $CF_2CF_3$ | $CF_3$ | $CH_3$ | H | F | H | 3-Me-2-benzofuranyl |
| 1-060 | $CF_2CF_3$ | $CF_3$ | $CH_3$ | H | F | H | 4-Me-phenyl |
| 1-061 | $CF_2CF_3$ | $CF_3$ | $CH_3$ | H | F | H | $MeOCH_2CH_2$— |
| 1-062 | $CF_2CF_3$ | $CF_3$ | $CH_3$ | H | F | H | 7-(difluoromethyl)-5-methyl-[1,2,4]triazolo[1,5-a]pyrimidin-2-yl |

TABLE 1a-continued (Ic-1)

| Ex. No. | $Z^1$ | $Z^2$ | $Z^3$ | $R^1$ | $R^4$ | $R^5$ | Q |
|---|---|---|---|---|---|---|---|
| 1-063 | $CF_2CF_3$ | $CF_3$ | $CH_3$ | H | F | H | 2-CF3-4-Me-furan-2-yl |
| 1-064 | $CF_2CF_3$ | $CF_3$ | $CH_3$ | H | F | H | isopropyl |
| 1-065 | $CF_2CF_3$ | $CF_3$ | $CH_3$ | H | F | H | 1,1,2,2-tetramethylethyl |
| 1-066 | $CF_2CF_3$ | $CF_3$ | $CH_3$ | H | F | H | (R)-1-F-ethyl |
| 1-067 | $CF_2CF_3$ | $CF_3$ | $CH_3$ | H | F | H | 2-Me-3-furanyl |
| 1-068 | $CF_2CF_3$ | $CF_3$ | $CH_3$ | H | F | H | 2-Me-prop-1-yl |
| 1-069 | $CF_2CF_3$ | $CF_3$ | $CH_3$ | H | F | H | 5-Me-thien-2-yl |
| 1-070 | $CF_2CF_3$ | $CF_3$ | $CH_3$ | H | F | H | 2,3-$F_2$-phenyl |
| 1-071 | $CF_2CF_3$ | $CF_3$ | $CH_3$ | H | F | H | 2-F-phenyl |
| 1-072 | $CF_2CF_3$ | $CF_3$ | $CH_3$ | H | F | H | 2-EtO-phenyl |
| 1-073 | $CF_2CF_3$ | $CF_3$ | $CH_3$ | H | F | H | 3-F-phenyl |
| 1-074 | $CF_2CF_3$ | $CF_3$ | $CH_3$ | H | F | H | 2-$CF_3$O-phenyl |
| 1-075 | $CF_2CF_3$ | $CF_3$ | $CH_3$ | H | F | H | 3-cyanophenyl |
| 1-076 | $CF_2CF_3$ | $CF_3$ | $CH_3$ | H | F | H | ethyl |
| 1-077 | $CF_2CF_3$ | $CF_3$ | $CH_3$ | H | F | H | cyclopentyl |
| 1-078 | $CF_2CF_3$ | $CF_3$ | $CH_3$ | H | F | H | t-butyl |
| 1-079 | $CF_2CF_3$ | $CF_3$ | $CH_3$ | H | F | H | 2,2-dimethylprop-1-yl |
| 1-080 | $CF_2CF_3$ | $CF_3$ | $CH_3$ | H | F | H | 2,3-dimethylphenyl |
| 1-081 | $CF_2CF_3$ | $CF_3$ | $CH_3$ | H | F | H | 5-methylisoxazol-4-yl |
| 1-082 | $CF_2CF_3$ | $CF_3$ | $CH_3$ | H | F | H | 1,1-dimethyl-2-ethoxyethyl |
| 1-083 | $CF_2CF_3$ | $CF_3$ | $CH_3$ | H | F | H | 3-Cl-6-Me-benzothiophen-2-yl |
| 1-084 | $CF_2CF_3$ | $CF_3$ | $CH_3$ | H | F | H | 2,2-difluoro-1,3-benzodioxol-5-yl |
| 1-085 | $CF_2CF_3$ | $CF_3$ | $CH_3$ | H | F | H | 3-pyridinyl |
| 1-086 | $CF_2CF_3$ | $CF_3$ | $CH_3$ | H | F | H | 3-F-5-pyridinyl |
| 1-087 | $CF_2CF_3$ | $CF_3$ | $CH_3$ | H | F | H | 2-Me-4-pyridinyl |
| 1-088 | $CF_2CF_3$ | $CF_3$ | $CH_3$ | H | F | H | 4-CN-phenyl |
| 1-089 | $CF_2CF_3$ | $CF_3$ | $CH_3$ | H | F | H | 2-F-4-pyridinyl |
| 1-090 | $CF_2CF_3$ | $CF_3$ | $CH_3$ | H | F | H | 3,4-dimethylphenyl |
| 1-091 | $CF_2CF_3$ | $CF_3$ | $CH_3$ | H | F | H | 3-Me, 4-F-phenyl |
| 1-092 | $CF_2CF_3$ | $CF_3$ | $CH_3$ | H | F | H | 3-F, 4-Me-phenyl |
| 1-093 | $CF_2CF_3$ | $CF_3$ | $CH_3$ | H | F | H | 1,3-benzodioxol-5-yl |
| 1-094 | $CF_2CF_3$ | $CF_3$ | $CH_3$ | H | F | H | 3-MeO, 4-F-phenyl |
| 1-095 | $CF_2CF_3$ | $CF_3$ | $CH_3$ | H | F | H | 3-F, 4-MeO-phenyl |
| 1-096 | $CF_2CF_3$ | $CF_3$ | $CH_3$ | H | F | H | 4-Cl, 3-F-phenyl |
| 1-097 | $CF_2CF_3$ | $CF_3$ | $CH_3$ | H | F | H | 3-MeO, 4-Me—Ph |
| 1-098 | $CF_2CF_3$ | $CF_3$ | $CH_3$ | H | F | H | 2-CN-5-pyridinyl |
| 1-099 | $CF_2CF_3$ | $CF_3$ | $CH_3$ | H | F | H | 2-Cl-5-pyridinyl |
| 1-100 | $CF_2CF_3$ | $CF_3$ | $CH_3$ | H | F | H | 2-F-5-pyridinyl |
| 1-101 | $CF_2CF_3$ | $CF_3$ | $CH_3$ | H | F | H | 3-EtO, 4-F-phenyl |
| 1-102 | $CF_2CF_3$ | $CF_3$ | $CH_3$ | H | F | F | 2-CN-5-pyridinyl |
| 1-103 | $CF_2CF_3$ | $CF_3$ | $CH_3$ | $CH_3$ | F | F | 2-CN-5-pyridinyl |
| 1-104 | $CF_2CF_3$ | $CF_3$ | $CH_3$ | H | H | F | 2-CN-5-pyridinyl |
| 1-105 | $CF_2CF_3$ | $CF_3$ | $CH_3$ | $CH_3$ | H | F | 2-CN-5-pyridinyl |
| 1-106 | $CF_2CF_3$ | $CF_3$ | $CH_3$ | $CH_3$ | F | F | 2-CN-5-pyridinyl |
| 1-128 | $CF_2CF_3$ | $CF_3$ | $CH_3$ | H | F | F | 2-thiophenyl |
| 1-129 | $CF_2CF_3$ | $CF_3$ | $CH_3$ | H | F | F | 3-MeO-4-F-phenyl |
| 1-130 | $CF_2CF_3$ | $CF_3$ | $CH_3$ | H | F | F | 3-F-4-MeO-phenyl |
| 1-131 | $CF_2CF_3$ | $CF_3$ | $CH_3$ | $CH_3$ | H | F | 3-MeO-4-F-phenyl |
| 1-132 | $CF_2CF_3$ | $CF_3$ | $CH_3$ | H | F | F | 2-F-5-pyridinyl |
| 1-133 | $CF_2CF_3$ | $CF_3$ | $CH_3$ | $CH_3$ | F | F | 2-F-5-pyridinyl |
| 1-334 | $CF_2CF_3$ | $CF_3$ | $CH_3$ | H | H | F | 2-F-5-pyridinyl |

Inventive compounds of the formula (Ic-1) are compounds of the general formula (Ic) where W=O, $A_1$=$A_2$=CH, $A_3$=$CR^4$, $A_4$=$CR^5$ and $R^6$=H (i.e. n=0).

Especially preferred compounds of the formula (Ic-1) are also those which result from arbitrary combinations of the radical definitions listed in Table 1a for $Z^1$, $Z^2$, $Z^3$, $R^1$, $R^4$, $R^5$ and Q.

TABLE 1b (Ic-1)

| Ex. No. | $Z^1$ | $Z^2$ | $Z^3$ | $R^1$ | $R^4$ | $R^5$ | Q |
|---|---|---|---|---|---|---|---|
| 1-107 | $CF_2CF_3$ | $CF_3$ | $CH_3$ | H | F | H | phenylthiomethyl |
| 1-108 | $CF_2CF_3$ | $CF_3$ | $CH_3$ | H | F | H | (rac)-1-phenylethyl |
| 1-109 | $CF_2CF_3$ | $CF_3$ | $CH_3$ | H | F | H | (rac)-phenyl-cyclopentylmethyl |
| 1-110 | $CF_2CF_3$ | $CF_3$ | $CH_3$ | H | F | H | (rac)-tetralin |
| 1-111 | $CF_2CF_3$ | $CF_3$ | $CH_3$ | H | F | H | 1-(4-Me-phenyl)cyclohex-1-yl |
| 1-112 | $CF_2CF_3$ | $CF_3$ | $CH_3$ | H | F | H | 3-CF3-4-Me-pyrazol-1-yl-methyl |
| 1-113 | $CF_2CF_3$ | $CF_3$ | $CH_3$ | H | F | H | 1-phenylcycloprop-1-yl |
| 1-114 | $CF_2CF_3$ | $CF_3$ | $CH_3$ | H | F | H | benzyloxymethyl |
| 1-115 | $CF_2CF_3$ | $CF_3$ | $CH_3$ | H | F | H | 1-(4-Cl-phenyl)-cyclobut-1-yl |
| 1-116 | $CF_2CF_3$ | $CF_3$ | $CH_3$ | H | F | H | 3-$CF_3$-benzyl |
| 1-117 | $CF_2CF_3$ | $CF_3$ | $CH_3$ | H | F | H | 2-thiophenyl-methyl |
| 1-118 | $CF_2CF_3$ | $CF_3$ | $CH_3$ | H | F | H | phenoxyethyl |
| 1-119 | $CF_2CF_3$ | $CF_3$ | $CH_3$ | H | F | H | 1-methyl-1-(3-Cl-phenyl)ethyl |
| 1-120 | $CF_2CF_3$ | $CF_3$ | $CH_3$ | H | F | H | (rac)-1-(4-Cl-phenyl)-2-methyl-prop-1-yl |
| 1-121 | $CF_2CF_3$ | $CF_3$ | $CH_3$ | H | F | H | 3-F-benzyl |

TABLE 1b-continued (Ic-1)

| Ex. No. | Z¹ | Z² | Z³ | R¹ | R⁴ | R⁵ | Q |
|---|---|---|---|---|---|---|---|
| 1-122 | $CF_2CF_3$ | $CF_3$ | $CH_3$ | H | F | H | 1-(4-Cl-phenyl)-cyclobut-1-yl |
| 1-123 | $CF_2CF_3$ | $CF_3$ | $CH_3$ | H | F | H | (rac)-1-phenoxy-ethyl |
| 1-124 | $CF_2CF_3$ | $CF_3$ | $CH_3$ | H | F | H | (rac)-1-phenyl-prop-1-yl |
| 1-125 | $CF_2CF_3$ | $CF_3$ | $CH_3$ | H | F | H | 2-phenylethyl |
| 1-126 | $CF_2CF_3$ | $CF_3$ | $CH_3$ | H | F | H | 2-Cl-4-F-benzyl |
| 1-127 | $CF_2CF_3$ | $CF_3$ | $CH_3$ | H | F | H | N',N'-dimethyloxalyl-amide |

Inventive compounds of the formula (Ic-1) are compounds of the general formula (Ic) where W=O, $A_1$=$A_2$=CH, $A_3$=$CR^4$, $A_4$=$CR^5$ and $R^6$=H (i.e. n=0).

Especially preferred compounds of the formula (Ic-1) are also those which result from arbitrary combinations of the radical definitions listed in Table 1b for $Z^1$, $Z^2$, $Z^3$, $R^1$, $R^4$, $R^5$ and Q.

TABLE 2

(Ic-2)

| Ex. No. | Z¹ | Z² | Z³ | R¹ | R⁴ | R⁵ | Q |
|---|---|---|---|---|---|---|---|
| 2-001 | $CF_2CF_3$ | $CF_3$ | $CH_3$ | H | Cl | H | 4-F-phenyl |
| 2-002 | $CF_2CF_3$ | $CF_3$ | $CH_3$ | H | Cl | H | 3-Cl-2-pyridinyl |
| 2-003 | $CF_2CF_3$ | $CF_3$ | $CH_3$ | H | $CH_3$ | H | 4-F-phenyl |
| 2-004 | $CF_2CF_3$ | $CF_3$ | $CH_3$ | H | $CH_3$ | H | 4-pyridinyl |
| 2-005 | $CF_2CF_3$ | $CF_3$ | $CH_3$ | H | F | H | 4-pyridinyl |
| 2-006 | $CF_2CF_3$ | $CF_3$ | $CH_3$ | H | Cl | H | 4-pyridinyl |
| 2-007 | $CF_2CF_3$ | $CF_3$ | $CH_3$ | H | Cl | H | 3-MeO, 4-F-phenyl |
| 2-008 | $CF_2CF_3$ | $CF_3$ | $CH_3$ | H | Cl | H | 2-CN-5-pyridinyl |
| 2-009 | $CF_2CF_3$ | $CF_3$ | $CH_3$ | $CH_3$ | Cl | H | 2-CN-5-pyridinyl |

Inventive compounds of the formula (Ic-2) are compounds of the general formula (Ic) where W=O, $A_1$=CH, $A_2$=N, $A_3$=$CR^4$, $A_4$=$CR^5$ and $R^6$=H=H (i.e. n=0).

Especially preferred compounds of the formula (Ic-2) are also those which result from arbitrary combinations of the radical definitions listed in Table 2 for $Z^1$, $Z^2$, $Z^3$, $R^1$, $R^4$, $R^5$ and Q.

Analytical Data
NMR Peak List Method

The ¹H NMR data of selected examples are reported in the form of ¹H NMR peak lists. For each signal peak, first the δ value in ppm and then the signal intensity in round brackets are listed. The δ value-signal intensity number pairs for different signal peaks are listed with separation from one another by semicolons.

The peak list for one example therefore has the form of: $\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may but need not occur in NMR peak lists.

The lists of the ¹H NMR peaks are similar to the conventional ¹H NMR printouts and thus usually contain all peaks listed in conventional NMR interpretations.

In addition, like conventional ¹H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of ¹H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional ¹H NMR interpretation.

Further details of ¹H NMR peak lists can be found in Research Disclosure Database Number 564025.

Example 1-001

¹H-NMR (400.0 MHz, DMSO): δ=10.591 (2.2); 8.817 (3.5); 8.813 (2.2); 8.806 (2.3); 8.802 (3.7); 8.707 (3.9); 8.426 (4.3); 8.317 (0.4); 8.087 (2.1); 7.954 (2.2); 7.896 (3.5); 7.892 (2.2); 7.884 (2.2); 7.880 (3.4); 7.699 (1.0); 7.680 (1.2); 7.503 (0.7); 7.500 (0.5); 7.484 (2.1); 7.480 (1.3); 7.474 (1.9); 7.455 (1.9); 7.436 (0.6); 4.039 (0.3); 4.021 (0.3); 3.829 (10.2); 3.329 (25.9); 2.892 (16.0); 2.733 (14.0); 2.525 (0.5); 2.512 (12.9); 2.508 (25.5); 2.503 (33.3); 2.499 (24.2); 1.990 (1.4); 1.193 (0.4); 1.175 (0.8); 1.158 (0.4); 0.008 (1.3); 0.000 (30.9); −0.008 (1.5)

Example 1-002

¹H-NMR (400.0 MHz, DMSO): δ=10.280 (0.5); 8.656 (1.2); 8.371 (1.3); 7.954 (2.2); 7.927 (0.6); 7.364 (1.0); 7.355 (0.5); 7.351 (0.8); 3.813 (3.2); 3.330 (8.0); 2.892 (16.0); 2.733 (13.6); 2.512 (3.2); 2.508 (6.4); 2.503 (8.4);

2.499 (6.0); 2.494 (2.8); 1.235 (0.3); 0.814 (1.5); 0.806 (1.1); 0.798 (0.7); 0.793 (0.9); 0.787 (0.6); 0.781 (0.4); 0.773 (0.4); 0.769 (0.5); 0.008 (0.5); 0.000 (14.1); −0.009 (0.5)

Example 1-003

$^1$H-NMR (400.0 MHz, DMSO): δ=10.350 (2.4); 8.694 (4.2); 8.416 (4.7); 8.084 (3.2); 8.080 (3.1); 8.071 (2.4); 8.063 (2.3); 8.054 (0.9); 8.049 (2.1); 8.021 (0.4); 8.007 (0.5); 7.999 (0.5); 7.985 (0.4); 7.954 (2.2); 7.693 (0.7); 7.688 (1.2); 7.682 (0.7); 7.675 (0.8); 7.670 (1.4); 7.665 (0.8); 7.466 (0.5); 7.462 (0.4); 7.447 (3.9); 7.428 (1.9); 7.420 (0.4); 7.412 (2.2); 7.390 (3.9); 7.373 (0.7); 7.368 (1.9); 7.343 (0.4); 7.321 (0.8); 7.298 (0.4); 3.827 (11.1); 3.328 (27.3); 2.891 (16.0); 2.732 (13.6); 2.512 (16.7); 2.507 (32.9); 2.503 (42.8); 2.498 (30.8); 2.494 (15.0); 0.008 (1.6); 0.000 (37.7); −0.008 (1.4)

Example 1-004

$^1$H-NMR (400.0 MHz, DMSO): δ=10.775 (3.3); 8.781 (3.7); 8.709 (5.7); 8.617 (2.2); 8.605 (2.3); 8.421 (6.2); 8.024 (3.3); 7.953 (0.6); 7.735 (1.6); 7.721 (2.3); 7.708 (1.6); 7.613 (1.5); 7.594 (1.9); 7.509 (1.2); 7.489 (2.9); 7.473 (2.5); 7.453 (2.7); 7.434 (0.9); 5.757 (2.7); 3.824 (16.0); 3.326 (86.8); 2.891 (4.8); 2.731 (4.1); 2.676 (0.5); 2.671 (0.7); 2.667 (0.5); 2.511 (41.6); 2.507 (80.7); 2.502 (104.0); 2.498 (74.1); 2.493 (35.3); 2.334 (0.5); 2.329 (0.7); 2.325 (0.5); 1.259 (0.4); 1.235 (0.4); 0.146 (0.6); 0.008 (6.0); 0.000 (134.9); −0.009 (5.0); −0.150 (0.6)

Example 1-005

$^1$H-NMR (400.0 MHz, DMSO): δ=10.741 (3.4); 8.714 (6.1); 8.653 (2.4); 8.650 (2.6); 8.641 (2.6); 8.638 (2.6); 8.426 (6.6); 8.139 (2.4); 8.136 (2.4); 8.118 (2.6); 8.115 (2.6); 8.091 (3.4); 7.669 (1.6); 7.664 (1.1); 7.649 (2.1); 7.645 (3.8); 7.633 (2.5); 7.624 (2.4); 7.613 (2.3); 7.490 (1.0); 7.486 (0.7); 7.471 (3.2); 7.461 (2.9); 7.442 (2.9); 7.423 (1.0); 4.056 (1.2); 4.038 (3.7); 4.020 (3.7); 4.003 (1.3); 3.825 (16.0); 3.806 (0.6); 3.329 (54.8); 2.891 (0.9); 2.732 (0.7); 2.676 (0.3); 2.672 (0.4); 2.667 (0.3); 2.525 (1.2); 2.511 (26.9); 2.507 (54.4); 2.503 (71.2); 2.498 (51.5); 2.494 (24.9); 2.334 (0.3); 2.330 (0.4); 2.325 (0.3); 1.990 (16.0); 1.398 (15.9); 1.193 (4.3); 1.175 (8.5); 1.157 (4.2); 0.008 (0.6); 0.000 (18.3); −0.009 (0.6)

Example 1-006

$^1$H-NMR (400.0 MHz, DMSO): δ=10.665 (2.0); 8.709 (3.6); 8.652 (1.9); 8.639 (2.0); 8.4273 (3.9); 8.4265 (3.9); 8.062 (1.9); 8.025 (2.4); 8.024 (2.4); 7.903 (1.5); 7.899 (1.4); 7.890 (1.4); 7.887 (1.3); 7.695 (0.9); 7.690 (0.6); 7.675 (1.1); 7.516 (0.7); 7.512 (0.5); 7.500 (1.2); 7.497 (1.9); 7.493 (1.1); 7.483 (1.6); 7.464 (1.8); 7.444 (0.6); 4.038 (0.8); 4.020 (0.8); 3.828 (9.5); 3.569 (4.9); 3.332 (36.1); 2.525 (0.6); 2.512 (13.6); 2.508 (27.3); 2.503 (35.3); 2.499 (24.9); 2.494 (11.6); 1.990 (3.7); 1.398 (16.0); 1.193 (1.0); 1.175 (2.0); 1.157 (1.0); 0.008 (0.6); 0.000 (18.1); −0.009 (0.6)

Example 1-007

$^1$H-NMR (400.0 MHz, d$_6$-DMSO): δ=10.402 (3.3); 8.703 (5.9); 8.411 (6.4); 7.892 (3.6); 7.468 (1.2); 7.462 (0.9); 7.450 (3.1); 7.442 (3.5); 7.438 (3.5); 7.427 (3.4); 7.408 (1.8); 7.389 (0.6); 3.817 (16.0); 3.581 (1.3); 3.553 (3.9); 3.525 (4.1); 3.497 (1.4); 3.343 (141.3); 3.314 (0.4); 2.543 (14.8); 2.508 (29.0); 2.504 (37.3); 2.500 (28.6); 0.000 (5.0)

Example 1-008

$^1$H-NMR (400.0 MHz, d$_6$-DMSO): δ=9.947 (2.7); 8.657 (6.0); 8.373 (6.3); 7.919 (2.9); 7.498 (0.7); 7.493 (0.8); 7.486 (1.2); 7.482 (1.5); 7.476 (1.1); 7.471 (1.1); 7.362 (5.1); 7.350 (4.1); 3.816 (16.0); 3.334 (77.4); 2.543 (7.9); 2.525 (0.5); 2.512 (12.9); 2.508 (26.7); 2.503 (35.8); 2.499 (26.7); 2.368 (1.6); 2.350 (5.1); 2.331 (5.4); 2.312 (1.7); 1.113 (5.4); 1.094 (11.2); 1.075 (5.2); 0.000 (5.1)

Example 1-009

$^1$H-NMR (400.0 MHz, d$_6$-DMSO): δ=11.137 (2.2); 8.720 (6.2); 8.436 (6.7); 7.968 (2.1); 7.964 (3.6); 7.959 (2.3); 7.614 (1.5); 7.594 (1.9); 7.589 (1.7); 7.575 (1.6); 7.555 (2.4); 7.494 (2.5); 7.474 (3.3); 7.454 (1.3); 7.006 (0.7); 6.993 (0.3); 6.891 (0.7); 6.878 (1.4); 6.864 (0.7); 6.762 (0.3); 6.749 (0.7); 6.735 (0.4); 5.756 (1.3); 3.822 (16.0); 3.326 (30.7); 2.525 (0.7); 2.512 (16.3); 2.508 (33.5); 2.503 (44.8); 2.498 (33.2); 2.494 (16.8); 0.008 (0.8); 0.000 (24.6); −0.008 (1.1)

Example 1-010

$^1$H-NMR (400.0 MHz, d$_6$-DMSO): δ=10.340 (3.7); 8.697 (6.1); 8.419 (6.7); 8.106 (3.5); 7.994 (4.1); 7.977 (4.4); 7.708 (1.7); 7.702 (1.0); 7.690 (1.9); 7.685 (1.2); 7.631 (0.6); 7.613 (2.3); 7.607 (0.7); 7.595 (2.0); 7.570 (3.6); 7.551 (4.5); 7.534 (1.6); 7.463 (0.6); 7.460 (0.6); 7.446 (5.9); 7.428 (2.5); 7.409 (0.7); 3.829 (16.0); 3.334 (74.1); 2.542 (19.0); 2.507 (29.3); 2.503 (37.3); 2.499 (28.0); 0.000 (3.4)

Example 1-011

$^1$H-NMR (400.0 MHz, d$_6$-DMSO): δ=10.710 (3.6); 8.707 (5.8); 8.423 (6.3); 8.039 (16.0); 7.687 (1.5); 7.668 (1.8); 7.526 (1.1); 7.506 (2.8); 7.491 (2.4); 7.471 (2.7); 7.452 (0.9); 3.826 (15.3); 3.332 (239.3); 2.675 (0.5); 2.671 (0.7); 2.542 (34.9); 2.506 (77.5); 2.502 (102.4); 2.498 (78.3); 2.329 (0.7); 2.325 (0.5); 1.234 (0.6); 0.000 (7.6)

Example 1-012

$^1$H-NMR (400.0 MHz, d$_6$-DMSO): δ=10.496 (3.3); 8.695 (5.8); 8.411 (6.0); 8.059 (2.7); 7.712 (0.8); 7.708 (1.0); 7.693 (1.6); 7.690 (1.9); 7.674 (0.9); 7.671 (1.0); 7.634 (1.4); 7.629 (1.1); 7.615 (1.8); 7.608 (1.6); 7.593 (1.0); 7.587 (1.2); 7.582 (0.7); 7.573 (0.6); 7.569 (0.6); 7.470 (0.9); 7.466 (0.7); 7.451 (3.5); 7.446 (3.6); 7.426 (2.5); 7.407 (0.8); 7.392 (1.3); 7.367 (3.6); 7.348 (3.6); 7.331 (1.3); 7.329 (1.2); 3.824 (16.0); 3.334 (99.1); 2.542 (13.5); 2.525 (0.6); 2.512 (16.0); 2.507 (33.0); 2.503 (43.8); 2.498 (32.2); 2.494 (15.9); 1.235 (0.4); 0.000 (4.9)

Example 1-013

$^1$H-NMR (400.0 MHz, d$_6$-DMSO): δ=10.405 (3.7); 8.702 (6.2); 8.423 (6.7); 8.088 (3.4); 7.855 (1.9); 7.836 (2.3); 7.816 (1.2); 7.810 (1.5); 7.806 (1.1); 7.791 (1.1); 7.786 (1.4); 7.782 (1.1); 7.705 (1.0); 7.701 (1.7); 7.696 (1.1); 7.687 (1.2); 7.683 (2.0); 7.678 (1.2); 7.642 (0.9); 7.627 (1.0); 7.621 (1.7); 7.607 (1.7); 7.602 (1.2); 7.587 (1.0);

7.494 (0.9); 7.487 (1.1); 7.482 (1.0); 7.473 (1.7); 7.467 (3.6); 7.463 (4.2); 7.459 (4.8); 7.447 (0.9); 7.440 (2.9); 7.421 (0.9); 3.829 (16.0); 3.337 (68.0); 2.543 (23.1); 2.526 (0.5); 2.513 (11.0); 2.508 (22.3); 2.504 (29.5); 2.500 (21.7); 2.495 (10.9); 0.000 (3.1)

Example 1-014

$^1$H-NMR (400.0 MHz, d$_6$-DMSO): δ=10.453 (3.8); 8.705 (6.1); 8.425 (6.6); 8.068 (3.6); 7.735 (0.5); 7.723 (2.5); 7.718 (3.2); 7.702 (3.3); 7.697 (3.6); 7.674 (2.1); 7.582 (0.6); 7.576 (0.9); 7.570 (0.5); 7.559 (1.2); 7.553 (1.8); 7.547 (0.9); 7.536 (0.7); 7.530 (0.9); 7.525 (0.5); 7.498 (1.1); 7.494 (0.8); 7.479 (3.5); 7.475 (2.5); 7.470 (3.1); 7.451 (2.8); 7.432 (0.9); 3.829 (16.0); 3.338 (76.8); 2.544 (23.7); 2.509 (23.6); 2.505 (29.8); 2.500 (22.4); 0.000 (2.3)

Example 1-015

$^1$H-NMR (400.0 MHz, d$_6$-DMSO): δ=10.894 (3.6); 8.714 (6.2); 8.425 (6.8); 8.021 (3.5); 7.647 (0.4); 7.630 (1.0); 7.626 (0.9); 7.609 (1.8); 7.589 (2.4); 7.571 (2.5); 7.500 (1.2); 7.497 (0.9); 7.481 (3.1); 7.465 (2.8); 7.445 (3.0); 7.426 (1.0); 7.296 (0.6); 7.289 (3.1); 7.269 (4.4); 7.249 (2.6); 7.242 (0.6); 3.825 (16.0); 3.337 (74.0); 2.543 (35.4); 2.526 (0.4); 2.513 (10.5); 2.508 (21.6); 2.504 (28.6); 2.499 (21.1); 2.495 (10.6); 0.000 (3.3)

Example 1-016

$^1$H-NMR (400.0 MHz, d$_6$-DMSO): δ=10.134 (3.6); 8.691 (6.1); 8.412 (6.7); 8.377 (2.3); 8.374 (2.6); 8.370 (2.8); 8.367 (2.5); 8.316 (0.8); 8.049 (3.3); 7.683 (1.3); 7.676 (2.0); 7.670 (4.6); 7.663 (4.3); 7.654 (5.3); 7.644 (1.6); 7.641 (1.4); 7.445 (0.6); 7.434 (5.5); 7.418 (2.6); 7.399 (0.6); 3.824 (16.0); 3.323 (116.1); 2.675 (0.9); 2.671 (1.2); 2.666 (1.0); 2.506 (134.0); 2.502 (180.9); 2.497 (139.8); 2.333 (0.8); 2.328 (1.1); 2.324 (0.9); 1.989 (0.6); 1.398 (7.7); 0.146 (0.4); 0.008 (2.9); 0.000 (80.9); −0.008 (4.7); −0.150 (0.4)

Example 1-017

$^1$H-NMR (400.0 MHz, d$_6$-DMSO): δ=10.324 (3.7); 8.707 (6.2); 8.429 (6.6); 8.056 (2.5); 8.054 (2.8); 8.047 (2.8); 8.045 (2.9); 8.034 (3.5); 7.886 (2.6); 7.884 (2.7); 7.873 (2.7); 7.871 (2.7); 7.658 (1.0); 7.653 (1.8); 7.648 (1.1); 7.640 (1.2); 7.635 (2.1); 7.630 (1.3); 7.467 (0.7); 7.464 (0.6); 7.449 (5.8); 7.430 (2.6); 7.411 (0.7); 7.258 (2.4); 7.249 (2.6); 7.246 (2.7); 7.237 (2.3); 3.828 (16.0); 3.339 (69.5); 2.544 (25.0); 2.527 (0.4); 2.509 (20.6); 2.504 (27.4); 2.500 (20.6); 0.000 (2.7)

Example 1-018

$^1$H-NMR (400.0 MHz, d$_6$-DMSO): δ=10.261 (1.3); 8.707 (2.2); 8.425 (2.4); 7.999 (1.2); 7.994 (0.8); 7.936 (1.8); 7.923 (1.9); 7.606 (0.5); 7.601 (0.4); 7.586 (0.7); 7.582 (0.5); 7.485 (0.4); 7.469 (0.7); 7.466 (1.1); 7.462 (0.6); 7.449 (1.0); 7.429 (1.1); 7.410 (0.4); 7.235 (1.9); 7.222 (1.8); 3.822 (5.6); 3.325 (13.7); 2.525 (0.3); 2.511 (8.2); 2.507 (17.3); 2.502 (23.4); 2.498 (17.4); 2.493 (8.7); 1.989 (0.4); 1.398 (16.0); 0.008 (0.7); 0.000 (22.6); −0.009 (1.0)

Example 1-019

$^1$H-NMR (400.0 MHz, d$_6$-DMSO): δ=9.900 (3.2); 8.685 (5.2); 8.406 (5.7); 8.320 (5.0); 8.035 (5.5); 8.006 (2.8); 7.642 (0.8); 7.637 (0.9); 7.626 (1.5); 7.619 (1.0); 7.614 (1.0); 7.410 (4.4); 7.398 (3.5); 3.905 (16.0); 3.825 (13.4); 3.342 (106.7); 2.543 (30.5); 2.526 (0.5); 2.512 (12.0); 2.508 (23.5); 2.504 (30.2); 2.499 (22.3); 0.000 (1.8)

Example 1-020

$^1$H-NMR (400.0 MHz, d$_6$-DMSO): δ=10.567 (3.4); 8.766 (5.8); 8.662 (2.4); 8.659 (2.5); 8.650 (2.5); 8.647 (2.5); 8.484 (6.2); 8.317 (0.5); 8.219 (1.6); 8.214 (1.7); 8.201 (1.7); 8.196 (1.6); 8.139 (2.3); 8.135 (2.3); 8.118 (2.6); 8.115 (2.5); 7.661 (2.5); 7.650 (2.4); 7.641 (2.2); 7.629 (2.3); 7.617 (0.8); 7.612 (0.9); 7.606 (1.0); 7.600 (1.0); 7.596 (1.1); 7.590 (1.1); 7.584 (1.1); 7.579 (0.9); 7.439 (1.7); 7.417 (1.6); 7.413 (2.0); 7.391 (1.4); 3.826 (16.0); 3.327 (199.1); 2.676 (0.8); 2.671 (1.1); 2.667 (0.8); 2.542 (22.6); 2.524 (2.8); 2.511 (61.5); 2.507 (123.4); 2.502 (162.4); 2.498 (117.5); 2.493 (56.4); 2.333 (0.8); 2.329 (1.1); 2.324 (0.8); 0.008 (0.5); 0.000 (15.9); −0.008 (0.5)

Example 1-021

$^1$H-NMR (400.0 MHz, d$_6$-DMSO): δ=10.596 (3.7); 8.839 (5.4); 8.695 (2.2); 8.692 (2.3); 8.684 (2.3); 8.681 (2.2); 8.530 (5.7); 8.318 (3.5); 8.314 (3.4); 8.162 (2.0); 8.159 (2.1); 8.141 (2.3); 8.138 (2.2); 7.699 (2.0); 7.687 (2.0); 7.678 (1.9); 7.666 (2.3); 7.643 (4.7); 7.624 (2.8); 7.620 (2.6); 7.603 (1.0); 7.598 (1.0); 3.827 (16.0); 3.327 (95.8); 2.676 (0.5); 2.671 (0.7); 2.667 (0.5); 2.542 (2.1); 2.511 (42.1); 2.507 (81.7); 2.502 (106.3); 2.498 (78.3); 2.494 (38.9); 2.334 (0.5); 2.329 (0.7); 2.325 (0.5); 1.234 (0.6); 0.008 (0.3); 0.000 (8.8); −0.008 (0.4)

Example 1-022

$^1$H-NMR (601.6 MHz, d$_6$-DMSO): δ=19.972 (0.5); 10.243 (4.5); 8.814 (6.1); 8.553 (6.6); 8.320 (0.4); 8.108 (2.4); 8.098 (2.8); 8.093 (2.9); 8.084 (2.4); 7.909 (3.4); 7.906 (3.5); 7.678 (1.2); 7.664 (2.6); 7.661 (2.7); 7.642 (4.9); 7.628 (2.3); 7.415 (2.6); 7.400 (5.0); 7.386 (2.5); 3.831 (16.0); 3.339 (61.6); 2.615 (0.8); 2.521 (1.5); 2.518 (1.5); 2.506 (111.4); 2.503 (152.4); 2.500 (114.0); 2.387 (0.8); 1.397 (1.7); 0.096 (0.5); 0.000 (96.7); −0.100 (0.4)

Example 1-023

$^1$H-NMR (601.6 MHz, d$_6$-DMSO): δ=10.198 (4.7); 8.819 (6.0); 8.557 (6.4); 8.030 (4.2); 8.018 (4.4); 7.927 (3.6); 7.924 (3.7); 7.676 (1.2); 7.662 (2.8); 7.659 (2.9); 7.642 (5.3); 7.629 (4.4); 7.616 (1.7); 7.573 (3.1); 7.560 (4.8); 7.548 (2.1); 3.834 (16.0); 3.342 (46.2); 2.615 (0.3); 2.503 (61.3); 2.388 (0.4); 1.398 (2.4); 0.000 (31.9)

Example 1-024

$^1$H-NMR (601.6 MHz, d$_6$-DMSO): δ=10.544 (4.4); 8.833 (4.5); 8.823 (10.5); 8.561 (6.8); 7.932 (3.6); 7.929 (3.8); 7.922 (3.7); 7.913 (3.5); 7.711 (1.4); 7.707 (1.2); 7.697 (2.5); 7.693 (2.5); 7.666 (4.6); 7.652 (2.5); 5.762 (0.5); 3.835 (16.0); 3.344 (18.4); 2.507 (24.0); 2.505 (31.9); 2.502 (23.2); 0.000 (24.7); −0.006 (0.9)

Example 1-026

$^1$H-NMR (601.6 MHz, d$_6$-DMSO): δ=10.237 (4.1); 8.744 (6.0); 8.495 (6.7); 8.322 (0.5); 8.014 (3.7); 8.002 (4.1); 8.000 (3.3); 7.918 (1.5); 7.914 (1.6); 7.906 (1.6); 7.902

(1.5); 7.637 (1.8); 7.625 (3.0); 7.615 (1.7); 7.613 (1.9); 7.567 (3.1); 7.554 (4.7); 7.542 (2.0); 7.412 (1.5); 7.398 (1.7); 7.395 (1.8); 7.381 (1.4); 3.830 (16.0); 3.341 (59.7); 2.615 (0.4); 2.524 (0.7); 2.521 (0.8); 2.518 (0.8); 2.509 (25.0); 2.506 (54.8); 2.503 (75.7); 2.500 (54.7); 2.497 (25.3); 2.388 (0.4); 1.990 (0.6); 1.398 (4.8); 0.005 (1.8); 0.000 (54.9); −0.006 (2.0)

Example 1-027

$^1$H-NMR (601.6 MHz, $d_6$-DMSO): δ=10.274 (2.4); 8.743 (3.4); 8.494 (3.8); 8.099 (1.4); 8.096 (0.7); 8.090 (1.6); 8.084 (1.6); 8.079 (0.7); 8.075 (1.5); 7.913 (0.9); 7.910 (0.9); 7.901 (0.9); 7.898 (0.9); 7.646 (0.5); 7.642 (0.5); 7.638 (0.6); 7.634 (0.5); 7.632 (0.6); 7.628 (0.6); 7.624 (0.6); 7.620 (0.5); 7.414 (1.0); 7.409 (1.6); 7.395 (3.3); 7.383 (1.3); 7.380 (1.6); 4.036 (0.3); 4.024 (0.3); 3.832 (9.3); 3.345 (11.3); 2.511 (4.7); 2.508 (10.2); 2.505 (14.1); 2.502 (10.4); 2.500 (4.9); 1.991 (1.4); 1.397 (16.0); 1.188 (0.4); 1.176 (0.7); 1.164 (0.4); 0.005 (0.4); 0.000 (12.4); −0.006 (0.5)

Example 1-028

$^1$H-NMR (400.0 MHz, $d_6$-DMSO): δ=10.738 (3.6); 8.705 (6.0); 8.559 (2.1); 8.554 (2.4); 8.547 (2.4); 8.542 (2.4); 8.413 (6.5); 8.111 (2.1); 8.106 (2.3); 8.092 (2.5); 8.088 (2.4); 8.032 (3.5); 7.599 (3.4); 7.586 (3.4); 7.580 (3.9); 7.568 (2.3); 7.493 (1.1); 7.489 (0.8); 7.474 (3.2); 7.462 (2.8); 7.443 (2.8); 7.424 (0.9); 5.757 (5.2); 4.056 (0.4); 4.038 (1.2); 4.021 (1.2); 4.003 (0.4); 3.822 (16.0); 3.327 (46.4); 2.525 (0.7); 2.511 (17.8); 2.507 (37.1); 2.503 (49.9); 2.498 (37.4); 2.494 (19.1); 1.989 (5.2); 1.193 (1.4); 1.175 (2.8); 1.158 (1.4); 0.008 (0.9); 0.000 (26.5); −0.008 (1.1)

Example 1-029

$^1$H-NMR (400.0 MHz, $d_6$-DMSO): δ=10.082 (3.5); 8.687 (6.3); 8.648 (0.4); 8.414 (6.8); 7.880 (3.6); 7.527 (1.5); 7.507 (2.0); 7.476 (1.5); 7.457 (2.7); 7.421 (2.6); 7.402 (3.1); 7.382 (1.1); 4.515 (0.3); 3.823 (16.0); 3.333 (30.2); 2.953 (0.3); 2.514 (30.0); 2.510 (40.2); 2.505 (30.8); 2.318 (0.4); 1.996 (0.5); 1.706 (1.7); 10.696 (14.9); 1.686 (2.0); 1.673 (0.5); 1.664 (0.4); 1.405 (7.0); 1.183 (0.4)

Example 1-030

$^1$H-NMR (400.0 MHz, $d_6$-DMSO): δ=9.954 (1.2); 8.679 (2.4); 8.411 (2.6); 7.939 (0.8); 7.935 (1.3); 7.931 (0.9); 7.584 (0.6); 7.580 (0.5); 7.564 (0.7); 7.563 (0.7); 7.560 (0.6); 7.472 (0.3); 7.469 (0.6); 7.466 (0.4); 7.453 (0.7); 7.450 (1.0); 7.447 (0.7); 7.413 (1.0); 7.394 (1.3); 7.374 (0.5); 3.817 (6.0); 3.325 (6.9); 2.512 (4.0); 2.508 (8.4); 2.503 (11.4); 2.498 (8.3); 2.494 (4.1); 1.989 (0.6); 1.625 (0.8); 1.612 (1.9); 1.604 (1.9); 1.592 (1.0); 1.398 (16.0); 1.385 (2.1); 1.377 (2.1); 1.363 (0.8); 1.176 (0.3)

Example 1-031

$^1$H-NMR (400.0 MHz, $d_6$-DMSO): δ=10.882 (3.2); 8.690 (6.1); 8.433 (6.3); 8.431 (6.5); 8.4143 (6.5); 8.4137 (6.5); 8.131 (3.1); 7.760 (1.4); 7.740 (1.6); 7.574 (6.4); 7.572 (6.4); 7.499 (1.3); 7.496 (0.9); 7.480 (2.7); 7.456 (2.4); 7.417 (3.1); 5.756 (6.1); 3.867 (0.4); 3.827 (16.0); 3.810 (1.8); 3.325 (29.9); 2.923 (1.1); 2.870 (1.1); 2.676 (0.4); 2.672 (0.5); 2.668 (0.7); 2.525 (1.3); 2.520 (1.9); 2.512 (26.8); 2.507 (55.1); 2.503 (73.4); 2.498 (53.5); 2.494 (25.9); 2.330 (0.5); 2.325 (0.3); 1.259 (0.4); 1.235 (1.2); 0.146 (0.5); 0.008 (3.3); 0.000 (99.8); −0.009 (3.6); −0.150 (0.5)

Example 1-032

$^1$H-NMR (400.0 MHz, $d_6$-DMSO): δ=9.871 (3.6); 8.726 (5.5); 8.479 (6.2); 7.808 (1.5); 7.802 (1.6); 7.790 (1.5); 7.784 (1.5); 7.643 (0.8); 7.638 (0.8); 7.632 (0.9); 7.626 (1.0); 7.622 (1.1); 7.616 (1.0); 7.610 (1.0); 7.605 (0.9); 7.385 (1.6); 7.363 (1.7); 7.360 (1.9); 7.338 (1.4); 3.821 (14.4); 3.327 (10.1); 2.511 (13.7); 2.507 (26.4); 2.503 (34.2); 2.498 (25.6); 1.612 (1.6); 1.598 (4.1); 1.590 (4.5); 1.578 (2.1); 1.425 (2.3); 1.413 (4.7); 1.405 (5.4); 1.398 (16.0); 0.008 (10.0); 0.000 (20.7); −0.008 (0.9)

Example 1-033

$^1$H-NMR (400.0 MHz, $d_6$-DMSO): δ=11.154 (3.7); 8.771 (6.2); 8.518 (6.9); 7.768 (1.4); 7.763 (2.1); 7.750 (2.4); 7.745 (2.8); 7.738 (1.5); 7.729 (1.2); 7.723 (1.0); 7.717 (1.2); 7.712 (0.8); 7.463 (1.8); 7.441 (1.8); 7.438 (2.0); 7.416 (1.5); 7.007 (0.6); 6.892 (0.6); 6.878 (1.3); 6.865 (0.6); 6.750 (0.7); 6.736 (0.3); 3.826 (16.0); 3.329 (14.5); 2.526 (0.5); 2.512 (12.5); 20.508 (25.6); 2.503 (34.2); 2.499 (25.3); 2.494 (12.6); 1.990 (0.9); 1.398 (2.9); 1.176 (0.5); 0.008 (0.7); 0.000 (21.6); −0.008 (0.8)

Example 1-034

$^1$H-NMR (400.0 MHz, $d_6$-DMSO): δ=10.655 (3.0); 9.399 (6.1); 9.299 (11.6); 8.739 (5.9); 8.480 (6.4); 8.015 (1.7); 8.010 (1.8); 7.997 (10.8); 7.992 (1.8); 7.671 (0.9); 7.666 (1.0); 7.660 (1.1); 7.654 (1.2); 7.650 (1.3); 7.644 (1.3); 7.639 (1.2); 7.633 (1.0); 7.456 (1.6); 7.431 (2.1); 7.409 (1.4); 3.827 (16.0); 3.325 (69.7); 2.671 (1.3); 2.506 (154.5); 2.502 (193.0); 2.498 (152.5); 2.329 (1.3); 1.989 (1.2); 1.192 (0.3); 1.175 (0.6); 1.157 (0.4); 0.146 (1.4); 0.000 (263.3); −0.150 (1.4)

Example 1-035

$^1$H-NMR (400.0 MHz, $d_6$-DMSO): δ=9.802 (3.0); 8.729 (5.0); 8.475 (5.6); 8.330 (4.9); 8.024 (5.1); 7.927 (1.3); 7.922 (1.4); 7.909 (1.4); 7.903 (1.4); 7.597 (0.7); 7.591 (0.7); 7.585 (0.8); 7.579 (0.8); 7.576 (0.9); 7.570 (0.9); 7.564 (0.9); 7.558 (0.7); 7.391 (1.5); 7.370 (1.4); 7.365 (1.7); 7.344 (1.2); 3.902 (16.0); 3.825 (13.1); 3.335 (17.0); 3.333 (16.5); 3.328 (16.0); 2.525 (0.9); 2.511 (17.6); 2.507 (35.3); 2.503 (46.5); 2.498 (34.0); 2.494 (16.8); 0.146 (0.4); 0.008 (3.3); 0.000 (89.2); −0.009 (3.5); −0.150 (0.4)

Example 1-036

$^1$H-NMR (400.0 MHz, $d_6$-DMSO): δ=10.643 (3.0); 9.465 (4.3); 9.462 (4.4); 9.183 (4.5); 9.170 (4.6); 8.751 (6.1); 8.481 (6.8); 8.215 (1.5); 8.209 (1.6); 8.196 (1.6); 8.191 (1.6); 8.168 (2.6); 8.165 (2.7); 8.155 (2.6); 8.152 (2.6); 7.652 (0.8); 7.646 (0.9); 7.640 (1.0); 7.634 (1.0); 7.630 (1.1); 7.624 (1.1); 7.618 (1.1); 7.613 (1.0); 7.468 (1.8); 7.447 (1.7); 7.442 (2.1); 7.421 (1.5); 3.830 (16.0); 3.326 (34.1); 2.672 (0.5); 2.667 (0.3); 2.525 (1.3); 2.512 (25.2); 2.507 (51.5); 2.503 (680.6); 2.498 (50.4); 2.494 (24.8); 2.329 (0.4); 1.989 (0.5); 1.398 (2.8); 0.008 (1.4); 0.000 (40.9); −0.009 (1.5)

Example 1-037

$^1$H-NMR (400.0 MHz, $d_6$-DMSO): δ=8.701 (5.6); 8.482 (6.5); 7.941 (1.6); 7.936 (1.7); 7.923 (10.7); 7.917 (1.7);

7.615 (0.7); 7.609 (0.8); 7.603 (0.8); 7.597 (0.9); 7.594 (0.9); 7.588 (0.9); 7.582 (0.9); 7.577 (0.7); 7.407 (1.6); 7.391 (1.2); 7.258 (0.8); 7.234 (1.3); 7.211 (0.8); 7.130 (1.1); 7.108 (1.9); 7.087 (1.0); 5.758 (1.8); 3.820 (16.0); 3.367 (18.3); 3.327 (20.9); 2.672 (0.4); 2.525 (1.0); 2.520 (1.5); 2.512 (22.7); 2.507 (46.1); 2.503 (60.8); 2.498 (44.6); 2.494 (22.1); 2.330 (0.4); 1.989 (0.6); 1.398 (0.5); 0.000 (8.7)

Example 1-038

$^1$H-NMR (400.0 MHz, d$_6$-DMSO): δ=10.019 (3.9); 8.712 (6.2); 8.473 (6.9); 8.099 (2.4); 8.094 (1.1); 8.085 (2.7); 8.077 (2.9); 8.068 (1.1); 8.063 (2.5); 7.656 (3.2); 7.653 (3.5); 7.544 (1.7); 7.540 (1.6); 7.525 (2.0); 7.520 (2.0); 7.404 (2.9); 7.399 (1.0); 7.382 (5.7); 7.359 (5.3); 7.338 (2.4); 3.824 (16.0); 3.324 (93.0); 2.675 (0.8); 2.671 (1.2); 2.666 (0.9); 2.524 (2.8); 2.519 (4.3); 2.511 (65.7); 2.506 (136.0); 2.502 (182.1); 2.497 (134.5); 2.493 (67.2); 2.337 (0.4); 2.333 (0.9); 2.329 (1.2); 2.324 (0.9); 2.249 (14.0); 1.398 (9.9); 0.146 (0.8); 0.008 (5.8); 0.000 (177.8); −0.008 (6.8); −0.150 (0.8)

Example 1-039

$^1$H-NMR (400.0 MHz, d$_6$-DMSO): δ=10.293 (4.1); 8.741 (2.9); 8.736 (3.1); 8.533 (5.6); 8.316 (2.6); 8.110 (2.6); 8.097 (3.1); 8.088 (3.2); 8.075 (2.8); 7.986 (0.9); 7.963 (0.5); 7.955 (2.9); 7.950 (1.2); 7.941 (3.1); 7.933 (3.4); 7.925 (10.3); 7.919 (3.1); 7.911 (0.5); 7.904 (0.7); 7.882 (1.1); 7.867 (1.1); 7.846 (0.6); 7.430 (2.6); 7.408 (5.5); 7.395 (1.9); 7.385 (3.6); 7.379 (2.2); 7.355 (2.0); 7.331 (0.9); 7.306 (0.4); 7.299 (3.1); 7.294 (1.0); 7.282 (1.1); 7.277 (5.9); 7.260 (0.9); 7.255 (3.0); 4.037 (0.7); 4.019 (0.7); 3.813 (16.0); 3.323 (533.1); 2.675 (5.6); 2.671 (8.0); 2.666 (6.0); 2.524 (190.7); 2.510 (444.0); 2.506 (919.6); 2.502 (1233.6); 2.497 (916.3); 2.493 (458.2); 2.333 (5.7); 2.328 (8.0); 2.324 (6.1); 1.989 (2.9); 1.234 (0.6); 1.193 (0.8); 1.175 (1.6); 1.157 (0.8); 1.148 (0.8); 0.146 (5.4); 0.008 (37.2); 0.000 (1198.0); −0.008 (45.3); −0.065 (0.5); −0.074 (0.4); −0.150 (5.7)

Example 1-040

$^1$H-NMR (400.0 MHz, d$_6$-DMSO): δ=10.284 (3.7); 8.816 (4.2); 8.802 (4.6); 8.721 (5.8); 8.480 (6.2); 7.916 (3.8); 7.901 (3.8); 7.681 (3.2); 7.571 (1.6); 7.568 (1.6); 7.552 (2.0); 7.548 (2.0); 7.378 (2.8); 7.358 (2.3); 5.757 (5.0); 4.056 (0.9); 4.038 (2.7); 4.021 (2.7); 4.003 (1.0); 3.826 (16.0); 3.329 (20.0); 2.507 (32.6); 2.503 (43.0); 2.498 (32.7); 2.260 (14.1); 1.989 (110.4); 1.398 (0.4); 1.193 (3.0); 1.175 (5.8); 1.158 (2.9); 0.008 (1.6); 0.000 (43.4); −0.008 (2.0)

Example 1-041

$^1$H-NMR (400.0 MHz, d$_6$-DMSO): δ=10.049 (4.0); 8.736 (6.2); 8.485 (6.8); 8.393 (2.5); 8.390 (2.7); 8.386 (2.8); 8.382 (2.6); 8.317 (0.4); 7.906 (1.5); 7.900 (1.7); 7.887 (1.6); 7.882 (1.6); 7.686 (1.7); 7.679 (1.7); 7.674 (3.3); 7.666 (3.3); 7.647 (3.3); 7.644 (3.4); 7.635 (2.6); 7.631 (2.2); 7.623 (1.0); 7.617 (1.0); 7.613 (1.1); 7.607 (1.1); 7.601 (1.0); 7.596 (0.9); 7.411 (1.8); 7.390 (1.7); 7.386 (2.1); 7.364 (1.5); 3.826 (16.0); 3.325 (124.6); 2.675 (2.0); 2.671 (1.3); 2.666 (0.9); 2.524 (3.2); 2.519 (4.8); 2.511 (70.9); 2.506 (146.7); 2.502 (195.5); 2.497 (142.8); 2.493 (70.0); 2.333 (0.9); 2.329 (1.3); 2.324 (0.9); 2.320 (0.5); 1.398 (7.1); 0.146 (0.9); 0.008 (6.6); 0.000 (202.2); −0.009 (7.3); −0.150 (0.9)

Example 1-085

$^1$H-NMR (400.0 MHz, d$_6$-DMSO): δ=10.462 (4.1); 9.152 (3.0); 9.147 (3.0); 8.802 (2.1); 8.798 (2.3); 8.790 (2.3); 8.786 (2.3); 8.740 (6.0); 8.489 (6.6); 8.350 (1.1); 8.345 (1.7); 8.340 (1.2); 8.330 (1.2); 8.325 (1.8); 8.320 (1.2); 7.958 (1.6); 7.952 (1.7); 7.940 (1.7); 7.934 (1.7); 7.664 (0.9); 7.658 (0.9); 7.652 (1.0); 7.646 (1.0); 7.643 (1.1); 7.637 (1.2); 7.631 (1.1); 7.625 (1.0); 7.612 (1.6); 7.600 (1.6); 7.592 (1.6); 7.580 (1.5); 7.437 (1.7); 7.415 (1.8); 7.412 (2.1); 7.390 (1.5); 3.828 (16.0); 3.331 (246.9); 2.676 (0.6); 2.671 (0.8); 2.667 (0.6); 2.525 (2.1); 2.507 (93.6); 2.502 (123.0); 2.498 (92.8); 2.334 (0.6); 2.329 (0.8); 2.325 (0.6); 1.989 (1.2); 1.193 (0.3); 1.175 (0.7); 1.157 (0.3); 0.008 (0.4); 0.000 (11.8); −0.008 (0.5)

Example 1-086

$^1$H-NMR (400.0 MHz, d$_6$-DMSO): δ=10.550 (3.0); 9.033 (3.4); 8.843 (3.5); 8.836 (3.6); 8.739 (6.1); 8.534 (0.5); 8.485 (6.7); 8.288 (0.6); 8.255 (1.1); 8.250 (1.3); 8.248 (1.4); 8.244 (1.1); 8.231 (1.1); 8.227 (1.4); 8.225 (1.3); 8.220 (1.1); 7.963 (1.6); 7.958 (1.7); 7.945 (1.7); 7.940 (1.7); 7.675 (0.9); 7.669 (0.9); 7.664 (1.0); 7.658 (1.0); 7.654 (1.1); 7.648 (1.1); 7.642 (1.1); 7.637 (0.9); 7.449 (1.8); 7.427 (1.8); 7.424 (2.1); 7.402 (1.5); 5.225 (0.4); 4.038 (0.5); 4.020 (0.5); 3.828 (16.0); 3.803 (1.5); 3.324 (112.5); 2.676 (0.8); 2.671 (1.1); 2.667 (0.8); 2.524 (3.0); 2.511 (60.6); 2.507 (121.7); 2.502 (160.0); 2.497 (116.9); 2.493 (57.3); 2.338 (0.4); 2.333 (0.8); 2.329 (1.0); 2.324 (0.8); 1.989 (1.9); 1.398 (0.5); 1.193 (0.5); 1.175 (1.1); 1.157 (0.5); 0.146 (0.7); 0.008 (5.3); 0.000 (155.6); −0.009 (5.8); −0.150 (0.7)

Example 2-001

$^1$H-NMR (400.0 MHz, DMSO): δ=10.386 (2.6); 8.926 (6.2); 8.752 (4.4); 8.746 (4.5); 8.650 (7.0); 8.404 (4.6); 8.398 (4.5); 8.316 (0.3); 8.124 (2.7); 8.119 (1.1); 8.110 (3.0); 8.102 (3.1); 8.094 (1.2); 8.088 (2.9); 7.442 (3.0); 7.437 (0.9); 7.420 (5.7); 7.403 (0.9); 7.398 (2.8); 3.840 (16.0); 3.325 (59.1); 2.676 (0.4); 2.672 (0.5); 2.667 (0.4); 2.525 (1.3); 2.520 (2.1); 2.511 (30.6); 2.507 (62.7); 2.502 (83.3); 2.498 (60.2); 2.493 (28.6); 2.334 (0.4); 2.329 (0.5); 2.325 (0.4); 1.989 (1.1); 1.398 (3.1); 1.175 (0.6); 0.146 (0.3); 0.008 (2.8); 0.000 (83.9); −0.009 (2.7); −0.150 (0.4)

Example 2-002

$^1$H-NMR (400.0 MHz, DMSO): δ=10.706 (3.5); 8.972 (4.6); 8.714 (4.1); 8.710 (4.5); 8.703 (2.4); 8.700 (2.3); 8.693 (3.9); 8.688 (2.5); 8.651 (5.0); 8.316 (1.7); 8.176 (1.7); 8.158 (1.8); 8.155 (1.8); 7.721 (1.5); 7.709 (1.5); 7.700 (1.4); 7.689 (1.3); 4.038 (0.3); 4.020 (0.4); 3.837 (16.0); 3.323 (410.7); 2.680 (1.2); 2.675 (2.6); 2.671 (3.7); 2.666 (2.6); 2.661 (1.2); 2.524 (8.8); 2.519 (14.0); 2.511 (201.5); 2.506 (413.9); 2.502 (552.3); 2.497 (399.1); 2.492 (189.6); 2.338 (1.3); 2.333 (2.7); 2.328 (3.7); 2.324 (2.7); 2.319 (1.3); 1.989 (1.4); 1.398 (1.6); 1.235 (0.5); 1.193 (0.4); 1.175 (0.8); 1.157 (0.4); 0.951 (0.3); 0.935 (0.3); 0.146 (2.4); 0.008 (18.0); 0.000 (568.5); −0.009 (19.2); −0.022 (1.0); −0.046 (0.4); −0.150 (2.4)

Example 2-001

¹H-NMR (400.0 MHz, DMSO): δ=10.386 (2.6); 8.926 (6.2); 8.752 (4.4); 8.746 (4.5); 8.650 (7.0); 8.404 (4.6); 8.398 (4.5); 8.316 (0.3); 8.124 (2.7); 8.119 (1.1); 8.110 (3.0); 8.102 (3.1); 8.094 (1.2); 8.088 (2.9); 7.442 (3.0); 7.437 (0.9); 7.420 (5.7); 7.403 (0.9); 7.398 (2.8); 3.840 (16.0); 3.325 (59.1); 2.676 (0.4); 2.672 (0.5); 2.667 (0.4); 2.525 (1.3); 2.520 (2.1); 2.511 (30.6); 2.507 (62.7); 2.502 (83.3); 2.498 (60.2); 2.493 (28.6); 2.334 (0.4); 2.329 (0.5); 2.325 (0.4); 1.989 (1.1); 1.398 (3.1); 1.175 (0.6); 0.146 (0.3); 0.008 (2.8); 0.000 (83.9); −0.009 (2.7); −0.150 (0.4)

| Ex. No. | NMR peak list |
|---|---|
| 1-049 | 1H-NMR (400 MHz, DMSO-d6) δ [ppm]: −0.008 (0.44), 0.008 (0.40), 3.826 (16.00), 7.233 (2.29), 7.242 (2.50), 7.245 (2.50), 7.255 (2.42), 7.372 (1.56), 7.393 (2.08), 7.397 (1.83), 7.419 (1.85), 7.607 (0.95), 7.613 (1.10), 7.619 (1.15), 7.625 (1.14), 7.629 (1.04), 7.635 (1.04), 7.640 (0.93), 7.646 (0.90), 7.879 (3.45), 7.882 (3.96), 7.892 (2.69), 7.895 (3.80), 7.901 (1.79), 8.030 (2.52), 8.033 (2.68), 8.040 (2.60), 8.043 (2.47), 8.489 (6.71), 8.739 (6.14), 10.241 (4.28). |
| 1-054 | 1H-NMR (500 MHz, CHLOROFORM-d) δ [ppm]: 0.000 (0.54), 3.059 (16.00), 3.831 (6.12), 6.714 (1.78), 6.719 (0.58), 6.728 (0.63), 6.733 (1.80), 7.157 (0.86), 7.177 (1.11), 7.183 (0.54), 7.189 (0.57), 7.193 (0.55), 7.794 (1.94), 7.798 (0.61), 7.808 (0.63), 7.812 (1.84), 7.899 (1.75), 8.037 (0.56), 8.044 (0.55), 8.135 (2.18), 8.136 (2.05), 8.768 (0.60), 8.773 (0.62), 8.783 (0.61), 8.788 (0.58). |
| 1-058 | 1H-NMR (400 MHz, DMSO-d6) δ [ppm]: −0.008 (1.75), 0.008 (1.51), 0.655 (1.51), 0.665 (4.77), 0.672 (4.84), 0.681 (1.70), 1.085 (1.51), 1.093 (4.07), 1.101 (3.87), 1.110 (1.32), 1.412 (16.00), 2.366 (0.40), 2.710 (0.41), 3.814 (13.84), 7.293 (1.38), 7.314 (1.82), 7.318 (1.53), 7.339 (1.61), 7.536 (0.84), 7.542 (0.98), 7.547 (0.98), 7.553 (0.99), 7.557 (0.89), 7.563 (0.89), 7.569 (0.80), 7.575 (0.76), 7.751 (1.51), 7.757 (1.48), 7.769 (1.53), 7.775 (1.38), 8.450 (5.54), 8.452 (5.32), 8.702 (5.35), 9.137 (3.29). |
| 1-066 | 1H-NMR (400 MHz, DMSO-d6) δ [ppm]: −0.008 (1.26), 0.008 (1.04), 1.507 (4.92), 1.523 (5.24), 1.568 (5.05), 1.585 (5.05), 3.802 (1.86), 3.817 (16.00), 5.195 (0.44), 5.211 (1.73), 5.228 (1.38), 5.245 (0.42), 5.316 (0.42), 5.333 (1.34), 5.350 (1.31), 5.754 (1.89), 7.343 (1.46), 7.364 (2.04), 7.369 (1.68), 7.390 (1.75), 7.566 (0.98), 7.572 (1.11), 7.577 (1.14), 7.584 (1.20), 7.588 (1.05), 7.593 (1.00), 7.599 (0.90), 7.605 (0.83), 7.924 (1.68), 7.930 (1.72), 7.942 (1.74), 7.948 (1.64), 8.284 (0.62), 8.452 (6.34), 8.531 (0.59), 8.715 (6.07), 9.971 (3.13). |
| 1-084 | 1H-NMR (400 MHz, DMSO-d6) δ [ppm]: −0.008 (2.04), 0.008 (1.90), 2.524 (0.51), 3.826 (16.00), 7.378 (1.61), 7.399 (2.16), 7.403 (1.81), 7.425 (1.87), 7.595 (3.76), 7.616 (4.94), 7.620 (1.44), 7.626 (1.24), 7.632 (1.16), 7.636 (1.06), 7.641 (1.08), 7.647 (0.95), 7.653 (0.91), 7.890 (1.81), 7.895 (1.81), 7.908 (1.92), 7.913 (1.98), 7.918 (2.66), 7.922 (2.69), 7.939 (2.05), 7.943 (2.38), 7.993 (4.31), 7.998 (3.89), 8.480 (6.38), 8.481 (6.54), 8.732 (6.18), 10.290 (4.27). |
| 1-025 | 1H-NMR (400 MHz, DMSO-d6) delta [ppm]: −0.149 (1.32), −0.008 (16.00), 0.008 (10.39), 0.146 (1.32), 1.148 (0.82), 2.327 (1.73), 2.366 (2.14), 2.670 (1.83), 2.710 (2.24), 3.826 (10.29), 7.394 (0.92), 7.416 (1.43), 7.441 (1.12), 7.888 (3.16), 7.903 (3.16), 7.918 (1.22), 7.936 (1.22), 8.488 (3.97), 8.739 (3.67), 8.807 (3.36), 8.822 (3.36), 10.527 (2.75). |
| 1-087 | 1H-NMR (400 MHz, DMSO-d6) δ [ppm]: −0.008 (2.82), 0.008 (2.63), 2.327 (0.43), 2.366 (0.62), 2.523 (1.06), 2.584 (16.00), 2.670 (0.43), 2.710 (0.65), 3.285 (0.60), 3.826 (13.51), 7.387 (1.30), 7.409 (1.76), 7.413 (1.55), 7.434 (1.55), 7.629 (0.81), 7.634 (0.95), 7.640 (0.95), 7.646 (0.95), 7.650 (0.89), 7.656 (0.87), 7.661 (0.81), 7.667 (0.87), 7.678 (1.49), 7.680 (1.44), 7.693 (1.49), 7.764 (2.63), 7.766 (2.98), 7.899 (1.38), 7.905 (1.44), 7.917 (1.44), 7.923 (1.36), 8.482 (5.32), 8.484 (5.48), 8.656 (2.31), 8.667 (2.20), 8.735 (5.23), 10.458 (3.58). |
| 1-088 | 1H-NMR (400 MHz, DMSO-d6) δ [ppm]: −0.008 (2.53), 0.008 (2.23), 3.825 (16.00), 5.754 (1.02), 7.387 (1.48), 7.408 (2.02), 7.413 (1.78), 7.434 (1.74), 7.627 (0.95), 7.632 (1.09), 7.638 (1.13), 7.644 (1.11), 7.648 (1.02), 7.654 (1.01), 7.660 (0.91), 7.665 (0.86), 7.914 (1.69), 7.920 (1.73), 7.932 (1.76), 7.938 (1.62), 8.039 (4.08), 8.044 (1.66), 8.056 (2.11), 8.061 (6.58), 8.135 (6.02), 8.140 (2.08), 8.152 (1.73), 8.157 (3.86), 8.481 (6.11), 8.483 (6.43), 8.733 (6.06), 10.494 (4.24). |
| 1-089 | 1H-NMR (400 MHz, DMSO-d6) δ [ppm]: −0.008 (3.67), 0.008 (2.13), 2.366 (0.64), 2.670 (0.45), 2.711 (0.73), 3.826 (16.00), 7.404 (1.54), 7.425 (2.07), 7.430 (1.79), 7.451 (1.74), 7.645 (1.15), 7.651 (1.26), 7.657 (1.35), 7.662 (1.40), 7.666 (1.37), 7.673 (2.38), 7.678 (3.95), 7.684 (2.52), 7.854 (1.20), 7.859 (1.71), 7.871 (1.74), 7.928 (1.79), 7.934 (1.77), 7.946 (1.79), 7.952 (1.63), 8.475 (2.55), 8.477 (3.45), 8.481 (6.50), 8.483 (6.73), 8.490 (2.86), 8.736 (6.02), 10.616 (3.67). |
| 1-090 | 1H-NMR (400 MHz, DMSO-d6) δ [ppm]: −0.008 (3.86), 0.008 (2.81), 1.235 (0.39), 2.306 (12.07), 2.310 (16.00), 2.312 (14.43), 2.327 (0.82), 2.366 (0.85), 2.669 (0.52), 2.711 (0.85), 3.825 (12.34), 7.291 (1.90), 7.311 (2.06), 7.353 (1.24), 7.374 (1.67), 7.378 (1.44), 7.399 (1.41), 7.586 (0.82), 7.592 (0.92), 7.597 (0.92), 7.603 (0.92), 7.607 (0.88), 7.613 (0.82), 7.618 (0.75), 7.624 (0.69), 7.724 (1.28), 7.729 (1.47), 7.749 (1.34), 7.797 (2.39), 7.801 (2.45), 7.876 (1.37), 7.882 (1.37), 7.895 (1.37), 7.901 (1.28), 8.477 (4.38), 8.479 (5.01), 8.729 (4.65), 10.065 (3.24). |
| 1-091 | 1H-NMR (400 MHz, DMSO-d6) δ [ppm]: −0.149 (0.72), −0.008 (6.34), 0.008 (5.67), 0.146 (0.77), 2.321 (9.47), 2.327 (9.39), 2.367 (0.91), 2.710 (0.94), 3.826 (16.00), 7.292 (1.51), 7.315 (2.45), 7.338 (1.66), 7.364 (1.39), 7.385 (1.99), 7.410 (1.68), 7.599 (0.89), 7.638 (0.77), 7.874 (2.26), 7.881 (2.40), 7.893 (2.64), 7.898 (2.45), 7.953 (1.47), 7.972 (1.51), 8.479 (6.73), 8.728 (6.05), 10.183 (4.04). |
| 1-092 | 1H-NMR (400 MHz, DMSO-d6) δ [ppm]: −0.008 (1.55), 0.008 (1.36), 2.325 (9.00), 2.330 (8.62), 2.367 (0.78), 2.670 (0.45), 2.710 (0.78), 3.280 (0.52), 3.364 (0.65), 3.825 (16.00), 7.368 (1.43), 7.390 (2.01), 7.394 (1.81), 7.415 (1.75), 7.458 (1.04), 7.479 (2.20), 7.499 (1.10), 7.607 (0.84), 7.614 (1.10), 7.619 (1.10), 7.625 (1.10), |

| Ex. No. | NMR peak list |
|---|---|
| | 7.629 (1.04), 7.635 (0.97), 7.641 (0.91), 7.647 (0.84), 7.742 (1.55), 7.746 (1.88), 7.764 (2.07), 7.768 (4.08), 7.774 (1.55), 7.784 (2.14), 7.788 (1.55), 7.881 (1.75), 7.886 (1.81), 7.899 (1.81), 7.905 (1.68), 8.482 (6.67), 8.731 (6.02), 10.228 (4.02). |
| 1-093 | 1H-NMR (400 MHz, DMSO-d6) δ [ppm]: −0.008 (2.08), 0.008 (2.13), 2.366 (0.66), 2.710 (0.64), 3.287 (0.49), 3.824 (16.00), 6.143 (15.89), 7.061 (3.92), 7.081 (4.21), 7.351 (1.45), 7.373 (2.02), 7.377 (1.77), 7.398 (1.75), 7.526 (3.98), 7.531 (4.49), 7.586 (0.92), 7.592 (1.09), 7.598 (1.19), 7.603 (1.32), 7.607 (3.45), 7.612 (3.00), 7.619 (1.09), 7.628 (2.53), 7.632 (2.23), 7.864 (1.68), 7.870 (1.74), 7.882 (1.74), 7.888 (1.64), 8.477 (6.81), 8.726 (6.11), 10.027 (4.21). |
| 1-094 | 1H-NMR (400 MHz, DMSO-d6) δ [ppm]: −0.008 (0.52), 0.008 (0.42), 2.074 (0.74), 3.314 (15.90), 3.939 (16.00), 7.370 (1.25), 7.378 (1.11), 7.392 (1.58), 7.399 (2.48), 7.403 (1.28), 7.419 (1.55), 7.425 (1.29), 7.616 (0.73), 7.621 (1.33), 7.626 (1.41), 7.632 (1.36), 7.634 (1.16), 7.637 (1.46), 7.642 (1.21), 7.647 (1.16), 7.653 (1.03), 7.655 (0.99), 7.658 (0.74), 7.766 (1.21), 7.772 (1.16), 7.787 (1.24), 7.792 (1.14), 7.878 (1.12), 7.883 (1.12), 7.896 (1.15), 7.901 (1.08), 8.488 (4.32), 8.490 (4.24), 8.739 (4.10), 10.236 (2.82). |
| 1-095 | 1H-NMR (400 MHz, DMSO-d6) δ [ppm]: −0.008 (2.20), 0.008 (1.66), 2.367 (0.53), 2.524 (1.83), 2.710 (0.49), 3.825 (11.09), 3.937 (16.00), 7.316 (1.12), 7.337 (1.90), 7.359 (1.13), 7.363 (1.40), 7.384 (1.47), 7.388 (1.27), 7.410 (1.24), 7.599 (0.72), 7.605 (0.81), 7.611 (0.83), 7.617 (0.81), 7.621 (0.76), 7.626 (0.73), 7.632 (0.65), 7.638 (0.61), 7.840 (1.29), 7.846 (1.58), 7.872 (4.89), 7.877 (2.98), 7.890 (2.09), 7.896 (1.96), 7.899 (1.07), 8.480 (4.03), 8.481 (4.57), 8.730 (4.22), 10.140 (3.04). |
| 1-096 | 1H-NMR (400 MHz, DMSO-d6) δ [ppm]: −0.008 (1.12), 0.008 (1.08), 3.826 (16.00), 7.384 (1.49), 7.405 (2.04), 7.409 (1.79), 7.431 (1.75), 7.624 (0.94), 7.630 (1.11), 7.635 (1.14), 7.641 (1.12), 7.645 (1.04), 7.651 (1.02), 7.657 (0.92), 7.663 (0.88), 7.794 (1.35), 7.812 (1.84), 7.815 (2.57), 7.834 (2.38), 7.870 (2.38), 7.875 (2.36), 7.892 (2.61), 7.898 (2.24), 7.911 (1.76), 7.916 (1.64), 7.989 (1.95), 7.994 (1.81), 8.015 (1.92), 8.019 (1.80), 8.482 (6.69), 8.733 (6.04), 10.390 (4.26). |
| 1-097 | 1H-NMR (400 MHz, DMSO-d6) δ [ppm]: −0.008 (1.89), 0.008 (1.76), 2.228 (10.19), 3.827 (11.35), 3.881 (16.00), 7.293 (1.35), 7.296 (1.44), 7.314 (1.61), 7.316 (1.76), 7.366 (1.09), 7.387 (1.48), 7.392 (1.27), 7.413 (1.27), 7.527 (1.22), 7.531 (1.95), 7.540 (2.49), 7.545 (3.50), 7.601 (0.66), 7.607 (0.77), 7.613 (0.79), 7.619 (0.79), 7.623 (0.71), 7.629 (0.71), 7.634 (0.64), 7.640 (0.60), 7.878 (1.18), 7.883 (1.20), 7.896 (1.22), 7.902 (1.14), 8.487 (4.33), 8.489 (4.78), 8.739 (4.38), 10.130 (3.02). |
| 1-098 | 1H-NMR (400 MHz, DMSO-d6) δ [ppm]: −0.008 (2.47), 0.008 (2.26), 3.825 (16.00), 7.404 (1.42), 7.426 (1.96), 7.430 (1.71), 7.452 (1.67), 7.635 (0.94), 7.641 (1.12), 7.647 (1.14), 7.652 (1.14), 7.654 (1.00), 7.656 (1.05), 7.662 (1.00), 7.668 (0.91), 7.674 (0.84), 7.965 (1.64), 7.971 (1.69), 7.983 (1.69), 7.989 (1.60), 8.245 (2.42), 8.247 (2.56), 8.265 (2.90), 8.267 (2.94), 8.475 (6.00), 8.476 (6.28), 8.535 (1.92), 8.541 (1.92), 8.555 (1.64), 8.561 (1.67), 8.732 (6.07), 9.246 (2.42), 9.248 (2.81), 9.254 (2.53), 10.697 (2.37). |
| 1-099 | 1H-NMR (400 MHz, DMSO-d6) δ [ppm]: −0.008 (0.91), 0.000 (16.00), 0.008 (0.63), 1.989 (0.60), 3.826 (4.60), 7.393 (0.44), 7.415 (0.58), 7.419 (0.52), 7.440 (0.49), 7.726 (0.78), 7.728 (0.93), 7.747 (0.80), 7.749 (0.99), 7.936 (0.50), 7.942 (0.51), 7.954 (0.50), 7.960 (0.46), 8.367 (0.62), 8.373 (0.62), 8.387 (0.56), 8.394 (0.56), 8.479 (1.66), 8.480 (1.93), 8.734 (1.75), 8.980 (0.91), 8.987 (0.82), 10.519 (1.23). |
| 1-100 | 1H-NMR (400 MHz, DMSO-d6) δ [ppm]: −0.008 (1.56), 0.008 (1.39), 3.287 (0.43), 3.771 (1.39), 3.826 (16.00), 7.380 (1.69), 7.385 (1.71), 7.392 (1.72), 7.401 (1.86), 7.407 (1.89), 7.413 (2.21), 7.417 (1.86), 7.439 (1.82), 7.625 (0.99), 7.630 (1.10), 7.636 (1.17), 7.642 (1.15), 7.646 (1.05), 7.652 (1.02), 7.658 (0.92), 7.663 (0.88), 7.931 (1.65), 7.937 (1.69), 7.949 (1.71), 7.955 (1.61), 8.479 (6.19), 8.481 (6.45), 8.507 (0.95), 8.513 (1.01), 8.526 (1.40), 8.528 (1.47), 8.535 (1.45), 8.548 (0.92), 8.554 (0.93), 8.578 (0.43), 8.734 (6.14), 8.852 (2.56), 8.859 (2.50), 10.472 (4.29). |
| 1-101 | 1H-NMR (400 MHz, DMSO-d6) δ [ppm]: −0.008 (2.59), 0.008 (1.57), 1.377 (5.35), 1.394 (11.14), 1.412 (5.24), 3.826 (16.00), 4.181 (1.68), 4.199 (5.33), 4.216 (5.20), 4.234 (1.52), 5.754 (0.67), 7.363 (1.83), 7.374 (1.77), 7.384 (2.36), 7.391 (2.29), 7.395 (2.47), 7.399 (1.96), 7.412 (2.18), 7.421 (1.88), 7.608 (1.39), 7.611 (1.89), 7.613 (2.08), 7.618 (2.22), 7.624 (2.26), 7.629 (2.21), 7.633 (1.93), 7.639 (1.80), 7.645 (1.72), 7.650 (0.95), 7.749 (1.85), 7.755 (1.70), 7.770 (1.80), 7.775 (1.63), 7.872 (1.77), 7.878 (1.73), 7.890 (1.78), 7.896 (1.62), 8.486 (6.84), 8.736 (6.18), 10.216 (4.27). |
| 1-106 | 1H-NMR (500 MHz, DICHLOROMETHANE-d2) δ [ppm]: 1.205 (0.41), 3.400 (0.91), 3.402 (0.74), 3.477 (8.64), 3.788 (1.36), 3.832 (16.00), 3.846 (1.35), 7.073 (0.56), 7.093 (0.99), 7.111 (0.58), 7.416 (1.25), 7.432 (1.90), 7.441 (1.39), 7.449 (1.18), 7.459 (0.92), 7.463 (0.70), 7.584 (0.87), 7.601 (0.92), 7.848 (1.01), 7.855 (1.40), 7.875 (4.32), 7.890 (0.44), 8.063 (3.69), 8.622 (1.14). |
| 1-127 | 1H-NMR (400 MHz, DMSO-d6) δ [ppm]: −0.008 (1.49), 0.008 (1.07), 2.524 (0.76), 2.937 (12.88), 3.057 (16.00), 3.815 (10.31), 7.395 (0.71), 7.414 (2.03), 7.433 (1.83), 7.450 (1.07), 7.454 (1.92), 7.458 (1.22), 7.469 (0.58), 7.473 (0.84), 7.477 (0.45), 7.524 (0.99), 7.529 (1.31), 7.533 (0.90), 7.544 (0.71), 7.549 (0.94), 7.552 (0.63), 7.971 (1.43), 7.976 (2.27), 7.981 (1.29), 8.402 (4.14), 8.687 (3.86), 10.760 (2.12). |
| 1-128 | 1H-NMR (400 MHz, CHLOROFORM-d) δ [ppm]: 0.000 (1.41), 3.797 (8.35), 3.836 (12.86), 3.843 (16.00), 3.856 (3.05), 3.858 (2.78), 6.865 (1.32), 6.872 (1.95), 6.877 (2.99), 6.881 (1.58), 6.896 (3.91), 7.032 (0.59), 7.036 (0.57), 7.054 (1.24), 7.058 (1.21), 7.076 (0.68), 7.080 (0.66), 7.128 (1.23), 7.138 (1.66), 7.141 (1.54), 7.150 (1.36), 7.447 (0.52), 7.461 (0.64), 7.468 (0.90), 7.483 (0.89), 7.490 (0.59), 7.504 (0.50), 7.538 (1.99), 7.575 (1.70), 7.578 (1.58), 7.587 (1.70), 7.591 (1.47), 7.709 |

| Ex. No. | NMR peak list |
|---|---|
| | (2.45), 7.720 (1.83), 7.723 (1.71), 7.730 (1.82), 7.732 (1.60), 7.834 (2.81), 7.986 (2.38), 7.988 (2.65), 7.992 (2.50), 8.001 (2.17), 8.007 (1.97), 8.153 (4.22), 8.163 (3.69). |
| 1-129 | 1H-NMR (400 MHz, DMSO-d6) δ [ppm]: −0.149 (0.63), −0.008 (6.67), 0.008 (6.56), 0.146 (0.63), 1.147 (0.63), 2.328 (0.48), 2.665 (0.44), 2.670 (0.52), 3.771 (0.67), 3.800 (0.85), 3.814 (11.41), 3.937 (16.00), 5.754 (4.85), 7.339 (0.70), 7.359 (1.33), 7.362 (1.41), 7.387 (1.74), 7.408 (1.48), 7.415 (1.30), 7.436 (1.37), 7.630 (0.70), 7.635 (0.93), 7.646 (0.89), 7.651 (0.81), 7.656 (0.81), 7.667 (0.67), 7.765 (1.22), 7.771 (1.26), 7.787 (1.33), 7.792 (1.22), 7.849 (0.48), 7.863 (0.63), 7.870 (0.93), 7.885 (0.96), 7.892 (0.59), 7.906 (0.48), 8.531 (3.96), 8.737 (2.26), 8.742 (2.30), 10.272 (3.41). |
| 1-130 | 1H-NMR (400 MHz, CHLOROFORM-d) δ [ppm]: 0.000 (1.19), 1.622 (1.64), 3.799 (6.41), 3.844 (16.00), 3.856 (3.35), 3.961 (8.30), 6.866 (1.15), 6.875 (2.18), 6.878 (2.84), 6.898 (3.29), 7.012 (0.62), 7.033 (1.10), 7.043 (0.58), 7.047 (0.56), 7.049 (0.49), 7.055 (0.64), 7.065 (0.95), 7.069 (0.83), 7.087 (0.50), 7.091 (0.44), 7.464 (0.44), 7.471 (0.61), 7.484 (0.60), 7.492 (0.41), 7.533 (1.43), 7.668 (0.70), 7.674 (0.87), 7.698 (2.19), 7.703 (1.53), 7.709 (2.13), 7.717 (0.96), 7.723 (0.68), 7.725 (0.55), 7.836 (2.08), 7.986 (2.31), 7.988 (2.51), 7.991 (2.33), 8.005 (1.55), 8.008 (1.63), 8.010 (1.43), 8.153 (3.69), 8.167 (2.45). |
| 1-132 | 1H-NMR (400 MHz, DMSO-d6) δ [ppm]: −0.008 (2.68), 0.008 (2.24), 3.286 (0.41), 3.814 (16.00), 7.354 (0.96), 7.356 (0.92), 7.374 (1.74), 7.377 (1.99), 7.378 (1.93), 7.399 (2.65), 7.406 (1.80), 7.421 (1.70), 7.427 (1.70), 7.864 (0.67), 7.879 (0.84), 7.886 (1.35), 7.901 (1.30), 7.908 (0.84), 7.923 (0.66), 8.524 (1.09), 8.532 (6.02), 8.545 (1.61), 8.551 (1.52), 8.565 (0.88), 8.571 (0.88), 8.741 (3.12), 8.746 (3.05), 8.874 (2.62), 8.881 (2.61), 10.531 (4.56). |
| 1-133 | 1H-NMR (500 MHz, DICHLOROMETHANE-d2) δ [ppm]: 0.000 (0.53), 3.398 (0.43), 3.410 (16.00), 3.829 (15.10), 6.810 (1.17), 6.811 (1.23), 6.816 (1.24), 6.817 (1.19), 6.827 (1.23), 6.828 (1.30), 6.833 (1.26), 6.834 (1.17), 6.964 (0.43), 6.970 (0.75), 6.981 (0.69), 6.984 (0.98), 6.988 (1.23), 6.990 (0.81), 7.002 (0.94), 7.501 (0.66), 7.513 (0.87), 7.519 (1.05), 7.529 (0.95), 7.534 (0.91), 7.547 (0.62), 7.849 (0.70), 7.854 (0.76), 7.864 (1.05), 7.866 (1.14), 7.869 (1.14), 7.871 (1.07), 7.881 (0.71), 7.886 (0.68), 7.998 (2.52), 8.001 (2.50), 8.142 (3.92), 8.176 (1.98), 8.181 (1.88). |
| 1-134 | 1H-NMR (400 MHz, DMSO-d6) δ [ppm]: −0.008 (0.92), 0.008 (0.86), 3.804 (0.47), 3.821 (16.00), 7.311 (1.34), 7.331 (2.91), 7.351 (1.66), 7.376 (1.70), 7.382 (1.68), 7.397 (1.75), 7.404 (1.69), 7.563 (0.91), 7.567 (1.06), 7.582 (1.60), 7.584 (1.78), 7.586 (1.73), 7.601 (0.86), 7.603 (0.83), 7.605 (0.81), 7.736 (0.93), 7.741 (1.02), 7.757 (1.79), 7.773 (0.90), 7.775 (0.91), 7.778 (0.84), 8.504 (0.95), 8.510 (1.01), 8.524 (1.65), 8.530 (1.87), 8.537 (5.74), 8.545 (1.13), 8.551 (0.99), 8.749 (3.21), 8.755 (3.05), 8.849 (2.71), 8.856 (2.68), 10.470 (4.17). |
| 2-003 | 1H-NMR (400 MHz, DMSO-d6) δ [ppm]: −0.149 (0.64), −0.008 (5.69), 0.008 (5.19), 0.146 (0.67), 2.073 (2.68), 2.327 (0.74), 2.366 (1.31), 2.465 (16.00), 2.670 (0.74), 2.674 (0.53), 2.710 (1.31), 3.286 (0.71), 3.833 (15.26), 7.382 (2.65), 7.388 (0.88), 7.399 (1.13), 7.404 (5.55), 7.410 (1.20), 7.421 (0.88), 7.427 (2.93), 8.072 (3.89), 8.076 (5.33), 8.089 (3.11), 8.097 (3.00), 8.106 (1.13), 8.111 (2.65), 8.577 (5.72), 8.579 (6.53), 8.748 (3.64), 8.753 (3.57), 8.837 (5.93), 10.173 (4.06). |
| 2-004 | 1H-NMR (400 MHz, DMSO-d6) δ [ppm]: −0.149 (0.41), −0.008 (3.40), 0.008 (3.32), 0.146 (0.41), 2.366 (0.44), 2.476 (16.00), 2.710 (0.43), 3.834 (15.30), 7.906 (4.24), 7.910 (2.90), 7.917 (2.90), 7.921 (4.44), 8.103 (3.02), 8.108 (3.05), 8.583 (6.05), 8.774 (3.52), 8.780 (3.53), 8.821 (5.10), 8.825 (3.12), 8.832 (3.18), 8.836 (5.17), 8.843 (6.10), 10.439 (3.94). |
| 2-005 | 1H-NMR (400 MHz, DMSO-d6) δ [ppm]: −0.149 (0.64), −0.008 (6.72), 0.008 (5.43), 0.146 (0.55), 2.073 (0.42), 2.327 (0.82), 2.366 (1.18), 2.524 (4.01), 2.710 (0.67), 3.286 (1.88), 3.836 (16.00), 7.889 (5.94), 7.893 (3.94), 7.900 (3.85), 7.904 (6.14), 8.508 (2.06), 8.516 (7.67), 8.537 (2.13), 8.542 (1.57), 8.591 (6.58), 8.593 (6.41), 8.822 (6.10), 8.826 (3.99), 8.833 (3.68), 8.837 (5.87), 8.861 (6.20), 10.720 (3.64). |
| 2-008 | 1H-NMR (400 MHz, DMSO-d6) δ [ppm]: −0.008 (2.25), 0.008 (2.02), 2.073 (3.44), 3.286 (0.71), 3.836 (16.00), 8.273 (2.62), 8.275 (2.59), 8.293 (3.03), 8.295 (3.05), 8.439 (4.09), 8.445 (4.26), 8.557 (2.31), 8.562 (2.29), 8.577 (1.97), 8.583 (2.00), 8.635 (6.89), 8.775 (4.13), 8.781 (3.92), 8.917 (6.29), 9.267 (2.59), 9.269 (3.03), 9.273 (2.95), 9.275 (2.62), 10.839 (3.89). |

LC-MS Data

Method M1:

Instrument: Waters ACQUITY SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method M2:

Instrument: Agilent MS Quad 6150; HPLC: Agilent 1290; column: Waters Acquity UPLC HSS T3 1.8μ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method M3:

Instrument MS: Waters SQD; Instrument HPLC: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method M4:
Instrument: Waters ACQUITY SQD UPLC System; column: Waters Acquity UPLC HSS T3 1.8 g 50×1 mm; eluent A: 1 1 water+0.25 ml 99% formic acid, eluent B: 1 1 acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

| Ex. No. | Method | Retention time [min] | M + H |
|---|---|---|---|
| 1-025 | M1 | 1.12 | 549 |
| 1-042 | M3 | 1.26 | 578 |
| 1-043 | M3 | 1.3 | 597 |
| 1-044 | M3 | 1.32 | 653 |
| 1-045 | M3 | 1.41 | 638 |
| 1-046 | M3 | 1.25 | 546 |
| 1-047 | M3 | 1.24 | 584 |
| 1-048 | M3 | 1.21 | 516 |
| 1-049 | M1 | 1.22 | 554 |
| 1-050 | M3 | 1.33 | 634 |
| 1-051 | M3 | 1.24 | 608 |
| 1-052 | M3 | 1.26 | 528 |
| 1-053 | M3 | 1.33 | 568 |
| 1-054 | M1 | 1.31 | 591 |
| 1-055 | M3 | 1.22 | 512 |
| 1-056 | M3 | 1.4 | 674 |
| 1-057 | M3 | 1.31 | 616 |
| 1-058 | M1 | 1.27 | 525 |
| 1-059 | M3 | 1.38 | 602 |
| 1-060 | M3 | 1.29 | 562 |
| 1-061 | M3 | 1.22 | 530 |
| 1-062 | M3 | 1.25 | 654 |
| 1-063 | M3 | 1.3 | 620 |
| 1-064 | M3 | 1.23 | 514 |
| 1-065 | M3 | 1.31 | 556 |
| 1-066 | M3 | 1.25 | 518 |
| 1-067 | M3 | 1.26 | 552 |
| 1-068 | M3 | 1.26 | 528 |
| 1-069 | M3 | 1.28 | 568 |
| 1-070 | M3 | 1.32 | 584 |
| 1-071 | M3 | 1.3 | 566 |
| 1-072 | M3 | 1.38 | 592 |
| 1-073 | M3 | 1.27 | 566 |
| 1-074 | M3 | 1.31 | 632 |
| 1-075 | M3 | 1.25 | 573 |
| 1-076 | M3 | 1.21 | 500 |
| 1-077 | M3 | 1.28 | 540 |
| 1-078 | M3 | 1.27 | 528 |
| 1-079 | M3 | 1.29 | 542 |
| 1-080 | M3 | 1.3 | 576 |
| 1-081 | M3 | 1.22 | 553 |
| 1-082 | M3 | 1.35 | 572 |
| 1-083 | M3 | 1.43 | 652 |
| 1-084 | M1 | 1.31 | 627 |
| 1-087 | M1 | 1.12 | 563 |
| 1-088 | M1 | 1.2 | 573 |
| 1-089 | M2 | 1.51 | 567 |
| 1-090 | M1 | 1.36 | 576 |
| 1-091 | M1 | 1.3 | 580 |
| 1-092 | M1 | 1.3 | 580 |
| 1-093 | M1 | 1.22 | 592 |
| 1-094 | M1 | 1.32 | 596 |
| 1-095 | M1 | 1.28 | 596 |
| 1-096 | M1 | 1.34 | 600 |
| 1-097 | M1 | 1.38 | 592 |
| 1-098 | M1 | 1.23 | 574 |
| 1-099 | M1 | 1.28 | 583 |
| 1-100 | M1 | 1.24 | 567 |
| 1-101 | M1 | 1.33 | 619 |
| 1-106 | M1 | 1.23 | 588 |
| 1-107 | M3 | 1.28 | 594 |
| 1-108 | M3 | 1.29 | 576 |
| 1-109 | M3 | 1.35 | 630 |
| 1-110 | M3 | 1.32 | 602 |
| 1-111 | M3 | 1.38 | 644 |
| 1-112 | M3 | 1.27 | 634 |
| 1-113 | M3 | 1.35 | 588 |
| 1-114 | M3 | 1.31 | 592 |
| 1-115 | M3 | 1.35 | 636 |
| 1-116 | M3 | 1.3 | 630 |
| 1-117 | M3 | 1.26 | 568 |
| 1-118 | M3 | 1.29 | 578 |
| 1-119 | M3 | 1.34 | 624 |
| 1-120 | M3 | 1.35 | 638 |
| 1-121 | M3 | 1.27 | 580 |
| 1-122 | M3 | 1.37 | 650 |
| 1-123 | M3 | 1.31 | 591 |
| 1-124 | M3 | 1.31 | 590 |
| 1-125 | M3 | 1.29 | 576 |
| 1-126 | M3 | 1.29 | 614 |
| 1-127 | M1 | 1.14 | 525 |
| 1-128 | M1 | 1.22 | 572 |
| 1-129 | M1 | 1.25 | 614 |
| 1-130 | M1 | 1.234 | 614 |
| 1-132 | M1 | 1.22 | 585 |
| 1-133 | M4 | 4.09 | 599 |
| 1-134 | M1 | 1.23 | 567 |
| 2-003 | M1 | 1.13 | 563 |
| 2-004 | M1 | 0.98 | 546 |
| 2-005 | M1 | 1.08 | 550 |
| 2-006 | M1 | 1.09 | 565 |
| 2-007 | M1 | 1.25 | 613 |
| 2-008 | M1 | 1.21 | 591 |

Intermediates

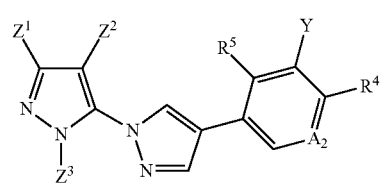

(INT-c-1)

Inventive compounds of the formula (INT-c-1) are compounds of the general formula 7 (Y=NO$_2$) or 8 (Y=NH$_2$) where A$_1$=CH, A$_3$=CR$^4$, A$_4$=CR$^5$ and E$_1$=N, E$_2$=E$_3$=CH.

| Ex. No. | Z$^1$ | Z$^2$ | Z$^3$ | A$_2$ | R$^4$ | R$^5$ | Y |
|---|---|---|---|---|---|---|---|
| INT-001 | CF$_2$CF$_3$ | CF$_3$ | CH$_3$ | CH | H | H | NO$_2$ |
| INT-002 | CF$_2$CF$_3$ | CF$_3$ | CH$_3$ | CH | H | H | NH$_2$ |
| INT-003 | CF$_2$CF$_3$ | CF$_3$ | CH$_3$ | CH | F | H | NO$_2$ |
| INT-004 | CF$_2$CF$_3$ | CF$_3$ | CH$_3$ | CH | F | H | NH$_2$ |
| INT-005 | CF$_2$CF$_3$ | CF$_3$ | CH$_3$ | CH | Cl | H | NO$_2$ |
| INT-006 | CF$_2$CF$_3$ | CF$_3$ | CH$_3$ | CH | Cl | H | NH$_2$ |
| INT-007 | CF$_2$CF$_3$ | CF$_3$ | CH$_3$ | CH | H | F | NO$_2$ |
| INT-008 | CF$_2$CF$_3$ | CF$_3$ | CH$_3$ | CH | H | F | NH$_2$ |
| INT-009 | CF$_2$CF$_3$ | CF$_3$ | CH$_3$ | CH | H | MeO | NO$_2$ |
| INT-010 | CF$_2$CF$_3$ | CF$_3$ | CH$_3$ | CH | H | MeO | NH$_2$ |
| INT-011 | CF$_2$CF$_3$ | CF$_3$ | CH$_3$ | N | H | H | NH$_2$ |
| INT-012 | CF$_2$CF$_3$ | CF$_3$ | CH$_3$ | N | Cl | H | NH$_2$ |
| INT-013 | CF$_2$CF$_3$ | CF$_3$ | CH$_3$ | CH | F | F | NO$_2$ |
| INT-014 | CF$_2$CF$_3$ | CF$_3$ | CH$_3$ | CH | F | F | NH$_2$ |
| INT-015 | CF$_2$CF$_3$ | CF$_3$ | CH$_3$ | N | F | H | NH$_2$ |
| INT-016 | CF$_2$CF$_3$ | CF$_3$ | CH$_3$ | N | CH$_3$ | H | NH$_2$ |

Analytical Data for Intermediates
NMR peak lists for intermediates

Example INT-001

$^1$H-NMR (400.0 MHz, DMSO): δ=8.991 (6.2); 8.699 (6.9); 8.563 (2.3); 8.559 (3.6); 8.554 (2.2); 8.201 (1.9);

8.197 (1.4); 8.181 (2.0); 8.180 (1.9); 8.177 (1.7); 8.174 (1.7); 8.171 (1.6); 8.168 (1.5); 8.166 (1.4); 8.153 (1.7); 8.151 (1.5); 8.147 (1.7); 8.145 (1.3); 7.769 (2.2); 7.749 (3.6); 7.729 (1.8); 3.846 (16.0); 3.775 (0.4); 3.328 (9.6); 2.527 (0.5); 2.514 (9.5); 2.510 (18.6); 2.505 (23.9); 2.501 (16.8); 2.496 (7.9); 1.398 (2.4); 0.008 (2.4); 0.000 (53.5); −0.009 (1.9)

Example INT-002

$^1$H-NMR (400.0 MHz, DMSO): δ=8.548 (6.1); 8.299 (6.8); 7.087 (1.2); 7.068 (2.8); 7.047 (1.7); 6.827 (5.3); 6.823 (6.0); 6.806 (1.9); 6.527 (1.4); 6.523 (2.0); 6.520 (1.3); 6.505 (1.5); 6.502 (1.5); 5.158 (2.6); 4.056 (0.3); 4.038 (1.1); 4.021 (1.1); 4.003 (0.4); 3.806 (16.0); 3.327 (20.5); 2.525 (0.6); 2.511 (13.9); 2.507 (27.9); 2.503 (36.3); 2.498 (25.7); 2.494 (12.2); 1.989 (4.7); 1.398 (0.4); 1.193 (1.2); 1.175 (2.5); 1.158 (1.2); 0.008 (1.0); 0.000 (26.5); −0.009 (0.9)

Example INT-003

$^1$H-NMR (400.0 MHz, DMSO): δ=8.924 (6.1); 8.651 (6.7); 8.536 (0.5); 8.530 (0.5); 8.518 (0.5); 8.512 (0.6); 8.502 (1.8); 8.496 (1.9); 8.484 (1.9); 8.478 (1.9); 8.218 (0.3); 8.180 (1.0); 8.174 (1.1); 8.170 (1.2); 8.164 (1.1); 8.158 (1.2); 8.152 (1.2); 8.148 (1.2); 8.142 (1.0); 7.778 (0.4); 7.756 (0.5); 7.750 (0.5); 7.729 (2.0); 7.708 (1.8); 7.702 (2.0); 7.680 (1.7); 3.836 (16.0); 3.733 (0.9); 3.329 (28.0); 2.509 (25.6); 2.504 (33.4); 2.500 (25.5); 1.990 (0.9); 1.398 (14.1); 1.176 (0.5); 0.000 (5.0)

Example INT-005

$^1$H-NMR (400.0 MHz, DMSO): δ=8.932 (5.9); 8.656 (6.2); 8.611 (0.6); 8.607 (0.6); 8.575 (0.7); 8.463 (4.1); 8.459 (3.8); 8.289 (0.9); 8.283 (0.8); 8.235 (0.8); 8.217 (0.4); 8.211 (0.3); 8.070 (1.9); 8.065 (1.7); 8.049 (2.3); 8.044 (2.1); 7.988 (0.9); 7.963 (0.6); 7.942 (0.6); 7.912 (0.5); 7.891 (0.6); 7.873 (3.7); 7.852 (3.0); 7.800 (0.5); 7.780 (0.5); 7.767 (0.4); 7.762 (0.4); 6.691 (0.6); 6.687 (0.8); 3.833 (16.0); 3.732 (3.7); 3.330 (49.3); 2.672 (0.4); 2.503 (63.4); 2.329 (0.4); 1.990 (1.2); 1.398 (1.0); 1.193 (0.3); 1.176 (0.6); 1.158 (0.3); 0.000 (2.9)

Example INT-006

$^1$H-NMR (400.0 MHz, DMSO): δ=8.588 (6.0); 8.318 (6.6); 7.250 (3.9); 7.230 (4.3); 7.053 (4.0); 7.048 (4.2); 6.877 (2.4); 6.872 (2.3); 6.856 (2.2); 6.851 (2.1); 5.758 (1.6); 5.427 (5.0); 3.806 (16.0); 3.331 (66.3); 2.672 (0.4); 2.525 (0.9); 2.512 (22.4); 2.507 (45.9); 2.503 (60.4); 2.498 (43.4); 2.494 (20.7); 2.329 (0.4); 0.008 (0.6); 0.000 (18.7); −0.009 (0.7)

Example INT-007

$^1$H-NMR (400.0 MHz, DMSO): δ=8.926 (6.0); 8.653 (6.7); 8.536 (1.2); 8.530 (1.3); 8.518 (1.2); 8.512 (1.3); 8.502 (1.8); 8.497 (1.9); 8.485 (1.8); 8.479 (1.8); 8.251 (0.7); 8.244 (0.7); 8.240 (0.8); 8.234 (0.7); 8.229 (0.8); 8.222 (0.8); 8.218 (0.8); 8.212 (0.7); 8.181 (0.9); 8.175 (1.0); 8.170 (1.1); 8.164 (1.0); 8.159 (1.1); 8.153 (1.1); 8.149 (1.1); 8.143 (0.9); 7.778 (1.3); 7.756 (1.2); 7.751 (1.4); 7.730 (2.5); 7.709 (1.8); 7.703 (1.9); 7.681 (1.7); 3.837 (16.0); 3.333 (29.8); 2.527 (0.7); 2.513 (13.7); 2.509 (27.5); 2.505 (36.0); 2.500 (25.7); 2.496 (12.3); 1.991 (0.6); 1.398 (1.9); 0.000 (4.9)

Example INT-008

$^1$H-NMR (400.0 MHz, DMSO): δ=8.614 (0.8); 8.537 (5.9); 8.374 (0.9); 8.291 (6.5); 7.064 (1.5); 7.043 (2.0); 7.035 (1.8); 7.029 (2.0); 7.024 (2.0); 7.014 (2.1); 7.007 (1.9); 7.002 (1.9); 6.841 (1.1); 6.835 (1.1); 6.830 (1.3); 6.824 (1.2); 6.820 (1.1); 6.814 (1.0); 6.809 (1.0); 6.804 (0.9); 5.232 (5.0); 3.835 (0.5); 3.805 (16.0); 3.332 (43.9); 2.512 (19.3); 2.508 (37.2); 2.503 (47.4); 2.499 (33.8); 2.495 (16.3); 1.990 (1.0); 1.398 (3.3); 1.175 (0.5); 0.008 (0.9); 0.000 (16.5); −0.009 (0.6)

Example INT-009

$^1$H-NMR (400.0 MHz, DMSO): δ=8.823 (4.1); 8.553 (4.4); 8.095 (1.4); 8.091 (1.5); 8.075 (1.6); 8.071 (1.5); 7.880 (1.5); 7.876 (1.5); 7.860 (1.7); 7.856 (1.6); 7.459 (1.6); 7.439 (2.7); 7.419 (1.4); 5.758 (0.4); 3.826 (10.4); 3.740 (16.0); 3.331 (21.6); 2.527 (0.4); 2.513 (9.2); 2.509 (18.2); 2.504 (23.4); 2.500 (16.8); 2.495 (8.1); 0.000 (6.9)

Example INT-012

$^1$H-NMR (400.0 MHz, DMSO): δ=8.718 (3.0); 8.431 (3.4); 8.430 (2.9); 7.966 (2.2); 7.961 (2.2); 7.343 (2.2); 7.337 (2.1); 5.684 (2.9); 3.933 (2.3); 3.815 (8.1); 3.329 (29.3); 2.508 (20.1); 2.503 (24.5); 2.499 (18.2); 1.990 (1.1); 1.176 (0.6); 1.070 (16.0); 0.000 (0.8)

LC-MS data for intermediates

| Ex. No. | Method | Retention time [min] | M + H |
|---|---|---|---|
| INT-014 | M1 | 1.20 | 462 |
| INT-015 | M1 | 1.09 | 445 |
| INT-016 | M1 | 0.80 | 441 |

BIOLOGICAL EXAMPLES

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 cm$^2$, given homogeneous distribution, an area-based dose of 5 μg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm². 100% efficacy means that all the fleas were dead or moribund. 0% efficacy means that no fleas were harmed.

In this test, for example, the following compounds from the preparation examples show an efficacy of 100% at an application rate of 5 µg/cm² (500 g/ha): 1-001, 1-003, 1-004, 1-006, 1-010, 1-012, 1-013, 1-016, 1-022, 1-023, 1-024, 1-025, 1-026, 1-027, 1-028, 1-031, 1-034, 1-036, 1-037, 1-040, 1-041, 1-049, 1-058, 1-064, 1-066, 1-068, 1-069, 1-073, 1-076, 1-081, 1-085, 1-086, 1-087, 1-088, 1-089, 1-091, 1-094, 1-095, 1-096, 1-097, 1-098, 1-099, 1-100, 1-101, 1-127, 2-005, 2-006

In this test, for example, the following compounds from the preparation examples show an efficacy of 80% at an application rate of 5 µg/cm² (500 g/ha): 1-039, 1-060, 1-083

In this test, for example, the following compounds from the preparation examples show an efficacy of 80% at an application rate of 1 µg/cm² (100 g/ha): 1-014

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 µl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 cm², given homogeneous distribution, an area-based dose of 5 µg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the floor of the tube and incubated on a hotplate at 45-50° C. for not more than 5 min. Ticks which remain motionless on the floor or move in such an uncoordinated manner that they are unable to deliberately avoid the heat by climbing upwards are considered to be dead or moribund.

A substance shows good efficacy against *Rhipicephalus sanguineus* if at least 80% efficacy was achieved in this test at an application rate of 5 µg/cm². An efficacy of 100% means that all the ticks were dead or moribund. 0% efficacy means that none of the ticks had been harmed.

In this test, for example, the following compounds from the preparation examples show an efficacy of 100% at an application rate of 5 µg/cm² (500 g/ha): 1-001, 1-002, 1-003, 1-004, 1-007, 1-008, 1-009, 1-010, 1-012, 1-013, 1-014, 1-016, 1-017, 1-022, 1-023, 1-024, 1-025, 1-026, 1-027, 1-028, 1-029, 1-031, 1-032, 1-034, 1-036, 1-038, 1-040, 1-041, 1-042, 1-048, 1-049, 1-054, 1-058, 1-060, 1-064, 1-066, 1-068, 1-069, 1-073, 1-075, 1-076, 1-077, 1-078, 1-081, 1-085, 1-086, 1-088, 1-089, 1-090, 1-091, 1-092, 1-093, 1-094, 1-095, 1-096, 1-097, 1-099, 1-100, 1-101, 1-117, 1-121, 1-127, 2-001, 2-003

In this test, for example, the following compounds from the preparation examples show an efficacy of 80% at an application rate of 5 µg/cm² (500 g/ha): 1-011, 1-015, 1-030, 1-035, 1-055, 1-061, 1-070, 1-084, 1-087, 1-098, 2-006

In this test, for example, the following compounds from the preparation examples show an efficacy of 100% at an application rate of 1 µg/cm² (100 g/ha): 1-033

In this test, for example, the following compounds from the preparation examples show an efficacy of 80% at an application rate of 1 µg/cm² (100 g/ha): 1-043, 2-005, 2-007

*Amblyomma hebaraeum* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Tick nymphs (*Amblyomma hebraeum*) are placed into perforated plastic cups and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds from the preparation examples show an efficacy of 100% at an application rate of 100 ppm: 1-022, 1-024, 1-025, 1-038, 1-040, 1-041, 1-088

In this test, for example, the following compounds from the preparation examples show an efficacy of 90% at an application rate of 100 ppm: 1-087

*Boophilus microplus*—Dip Test

Test animals: cattle ticks (*Boophilus microplus*) Parkhurst strain, SP-resistant Solvent: dimethyl sulphoxide 10 mg of active ingredient are dissolved in 0.5 ml of dimethyl sulphoxide. For the purpose of producing a suitable formulation, the active ingredient solution is diluted with water to the concentration desired in each case.

This active ingredient formulation is pipetted into tubes. 8-10 adult engorged female cattle ticks (*Boophilus microplus*) are transferred into a further tube with holes. The tube is immersed into the active ingredient formulation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: 1-004, 1-022, 1-024, 1-025, 1-026, 1-027, 1-038, 1-040, 1-041, 1-049, 1-060, 1-073, 1-080, 1-087, 1-088, 1-089, 1-094, 1-098, 1-099, 1-100

In this test, for example, the following compounds from the preparation examples show an efficacy of 95% at an application rate of 100 ppm: 1-001

In this test, for example, the following compounds from the preparation examples show an efficacy of 90% at an application rate of 100 ppm: 1-010, 1-042

In this test, for example, the following compounds from the preparation examples show an efficacy of 80% at an application rate of 100 ppm: 1-037, 2-001

*Boophilus microplus*—Injection Test

Solvent: dimethyl sulphoxide

To produce an appropriate active ingredient formulation, 10 mg of active ingredient are mixed with 0.5 ml of solvent and the concentrate is diluted with solvent to the desired concentration.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days.

An efficacy of 100% means that none of the ticks has laid any fertile eggs; 0% means that all the eggs are fertile.

In this test, for example, the following compounds from the preparation examples show an efficacy of 100% at an application rate of 20 µg/animal: 1-001, 1-002, 1-003, 1-004, 1-005, 1-006, 1-007, 1-008, 1-009, 1-010, 1-011, 1-012, 1-013, 1-014, 1-015, 1-016, 1-017, 1-018, 1-019, 1-020, 1-022, 1-023, 1-024, 1-025, 1-026, 1-027, 1-028, 1-029, 1-030, 1-031, 1-032, 1-033, 1-034, 1-035, 1-036, 1-037, 1-038, 1-040, 1-041, 1-042, 1-043, 1-046, 1-047, 1-048, 1-049, 1-050, 1-052, 1-054, 1-055, 1-057, 1-058, 1-059, 1-060, 1-061, 1-062, 1-063, 1-064, 1-065, 1-066, 1-067, 1-068, 1-069, 1-070, 1-071, 1-073, 1-075, 1-076, 1-077, 1-078, 1-079, 1-080, 1-081, 1-082, 1-084, 1-085, 1-086, 1-087, 1-088, 1-089, 1-091, 1-092, 1-093, 1-094, 1-095, 1-096, 1-097, 1-098, 1-099, 1-100, 1-101, 1-107, 1-108, 1-110, 1-114, 1-115, 1-116, 1-117, 1-118, 1-119, 1-121, 1-123, 1-124, 1-125, 1-126, 1-127, 2-001, 2-002, 2-003, 2-004, 2-005, 2-006, 2-007

In this test, for example, the following compounds from the preparation examples show an efficacy of 95% at an application rate of 20 µg/animal: 1-112

In this test, for example, the following compounds from the preparation examples show an efficacy of 90% at an application rate of 20 µg/animal: 1-074

In this test, for example, the following compounds from the preparation examples show an efficacy of 80% at an application rate of 20 µg/animal: 1-083, 1-109, 1-111

*Ctenocephalides felis*—Oral Test

Solvent: dimethyl sulphoxide

For the purpose of producing an appropriate active ingredient formulation, 10 mg of active ingredient are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: 1-001, 1-002, 1-003, 1-004, 1-005, 1-006, 1-007, 1-008, 1-009, 1-010, 1-011, 1-012, 1-013, 1-014, 1-015, 1-016, 1-017, 1-019, 1-022, 1-023, 1-024, 1-025, 1-026, 1-027, 1-028, 1-029, 1-030, 1-031, 1-032, 1-033, 1-034, 1-035, 1-036, 1-037, 1-038, 1-040, 1-041, 1-042, 1-043, 1-047, 1-049, 1-055, 1-058, 1-060, 1-061, 1-062, 1-064, 1-066, 1-067, 1-068, 1-069, 1-070, 1-073, 1-075, 1-076, 1-077, 1-081, 1-084, 1-085, 1-086, 1-087, 1-088, 1-089, 1-091, 1-092, 1-093, 1-094, 1-095, 1-096, 1-097, 1-098, 1-099, 1-100, 1-101, 1-116, 1-117, 1-121, 1-126, 1-127, 2-001, 2-003, 2-004, 2-005, 2-006, 2-007

In this test, for example, the following compounds from the preparation examples show an efficacy of 95% at an application rate of 100 ppm: 1-020, 1-048, 1-057, 1-079, 1-080

In this test, for example, the following compounds from the preparation examples show an efficacy of 90% at an application rate of 100 ppm: 1-052, 1-063, 1-065, 1-071, 1-082, 1-115, 1-123

In this test, for example, the following compounds from the preparation examples show an efficacy of 80% at an application rate of 100 ppm: 1-021, 1-078

*Lucilia cuprina* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active ingredient preparation of the desired concentration.

After 2 days, the kill in % is determined. 100% means that all the larvae have been killed and 0% means that none of the larvae have been killed.

In this test, for example, the following compounds from the preparation examples show an efficacy of 100% at an application rate of 100 ppm: 1-001, 1-002, 1-003, 1-004, 1-005, 1-006, 1-007, 1-008, 1-009, 1-010, 1-011, 1-012, 1-013, 1-014, 1-015, 1-016, 1-017, 1-019, 1-022, 1-023, 1-024, 1-025, 1-026, 1-027, 1-028, 1-029, 1-030, 1-031, 1-032, 1-033, 1-034, 1-035, 1-036, 1-037, 1-038, 1-040, 1-041, 1-042, 1-043, 1-046, 1-047, 1-049, 1-050, 1-052, 1-054, 1-055, 1-057, 1-058, 1-060, 1-062, 1-064, 1-067, 1-068, 1-069, 1-070, 1-071, 1-073, 1-075, 1-077, 1-078, 1-079, 1-081, 1-084, 1-085, 1-086, 1-087, 1-088, 1-089, 1-091, 1-092, 1-093, 1-094, 1-095, 1-096, 1-097, 1-098, 1-099, 1-100, 1-101, 1-116, 1-117, 1-119, 1-121, 1-126, 1-127, 2-001, 2-003, 2-004, 2-005, 2-006, 2-007

In this test, for example, the following compounds from the preparation examples show an efficacy of 95% at an application rate of 100 ppm: 1-048, 1-076

In this test, for example, the following compounds from the preparation examples show an efficacy of 90% at an application rate of 100 ppm: 1-020

In this test, for example, the following compounds from the preparation examples show an efficacy of 80% at an application rate of 100 ppm: 1-065, 1-066, 1-115

*Musca domestica* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: 1-001, 1-002, 1-003, 1-004, 1-006, 1-007, 1-010, 1-019, 1-024, 1-025, 1-027, 1-028, 1-034, 1-035, 1-036, 1-040, 1-055, 1-068, 1-075, 1-077, 1-084, 1-086, 1-087, 1-089, 1-094, 1-099, 1-100, 1-127, 2-001, 2-003

In this test, for example, the following compounds from the preparation examples show an efficacy of 90% at an application rate of 100 ppm: 1-013, 1-014, 1-026, 1-037, 1-073, 1-096, 1-126, 2-005, 2-006

In this test, for example, the following compounds from the preparation examples show an efficacy of 80% at an application rate of 100 ppm: 1-031, 1-032, 1-047, 1-049, 1-058, 1-071, 1-119, 2-004

*Myzus persicae*—Spray Test

| Solvent: | 78 parts by weight of acetone |
| --- | --- |
|  | 1.5 parts by weight of dimethylformamide |
| Emulsifier: | alkylaryl polyglycol ether |

To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, efficacy in % is determined. 100% means that all the aphids have been killed; 0% means that none of the aphids have been killed.

In this test, for example, the following compounds from the preparation examples show efficacy of 90% at an application rate of 500 g/ha: 1-016, 1-031

In this test, for example, the following compounds from the preparation examples show efficacy of 100% at an application rate of 100 g/ha: 1-001, 1-006, 1-009, 1-010, 1-025, 1-026, 1-027, 1-036, 1-040, 1-041, 1-064, 1-076, 1-081, 1-086, 1-098, 1-099, 1-100

In this test, for example, the following compounds from the preparation examples show efficacy of 90% at an application rate of 100 g/ha: 1-003, 1-012, 1-017, 1-019, 1-033, 1-048, 1-087, 1-089

*Phaedon cochleariae*—Spray Test

| Solvent: | 78.0 parts by weight of acetone |
| --- | --- |
|  | 1.5 parts by weight of dimethylformamide |
| Emulsifier: | alkylaryl polyglycol ether |

To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, efficacy in % is determined. 100% means that all the beetle larvae have been killed; 0% means that no beetle larvae have been killed.

In this test, for example, the following compounds from the preparation examples show efficacy of 100% at an application rate of 500 g/ha: 1-009, 1-016, 1-018, 1-031

In this test, for example, the following compounds from the preparation examples show efficacy of 83% at an application rate of 500 g/ha: 1-029

In this test, for example, the following compounds from the preparation examples show efficacy of 100% at an application rate of 100 g/ha: 1-001, 1-002, 1-003, 1-004, 1-005, 1-006, 1-007, 1-010, 1-011, 1-012, 1-013, 1-014, 1-015, 1-017, 1-019, 1-022, 1-023, 1-024, 1-025, 1-026, 1-027, 1-028, 1-034, 1-035, 1-036, 1-037, 1-038, 1-039, 1-040, 1-041, 1-042, 1-043, 1-047, 1-050, 1-054, 1-055, 1-060, 1-064, 1-067, 1-068, 1-069, 1-071, 1-073, 1-076, 1-081, 1-084, 1-085, 1-086, 1-087, 1-088, 1-089, 1-090, 1-091, 1-092, 1-093, 1-094, 1-095, 1-096, 1-097, 1-098, 1-099, 1-100, 1-101, 1-116, 1-121, 1-126, 1-127, 2-001, 2-003, 2-004, 2-005, 2-006, 2-007

In this test, for example, the following compounds from the preparation examples show efficacy of 83% at an application rate of 100 g/ha: 1-033

*Spodoptera frugiperda*—Spray Test

| Solvent: | 78.0 parts by weight of acetone |
| --- | --- |
|  | 1.5 parts by weight of dimethylformamide |
| Emulsifier: | alkylaryl polyglycol ether |

To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, efficacy in % is determined. 100% means that all the caterpillars have been killed; 0% means that no caterpillars have been killed.

In this test, for example, the following compounds from the preparation examples show efficacy of 100% at an application rate of 500 g/ha: 1-009, 1-016, 1-018, 1-029, 1-030, 1-031

In this test, for example, the following compounds from the preparation examples show efficacy of 100% at an application rate of 100 g/ha: 1-001, 1-003, 1-004, 1-005, 1-006, 1-007, 1-010, 1-012, 1-013, 1-014, 1-015, 1-017, 1-019, 1-022, 1-023, 1-024, 1-025, 1-026, 1-027, 1-028, 1-034, 1-035, 1-036, 1-037, 1-038, 1-039, 1-040, 1-041, 1-043, 1-052, 1-054, 1-055, 1-064, 1-067, 1-068, 1-069, 1-071, 1-073, 1-076, 1-078, 1-081, 1-084, 1-086, 1-087, 1-088, 1-089, 1-091, 1-092, 1-093, 1-095, 1-096, 1-097, 1-098, 1-099, 1-100, 1-101, 1-117, 1-121, 1-127, 2-001, 2-003, 2-004, 2-005, 2-006

In this test, for example, the following compounds from the preparation examples show efficacy of 83% at an application rate of 100 g/ha: 1-002, 1-057, 1-058, 1-060, 1-085, 1-094, 1-116

*Tetranychus urticae*—Spray Test, OP-Resistant

| Solvent: | 78.0 parts by weight of acetone |
| --- | --- |
|  | 1.5 parts by weight of dimethylformamide |
| Emulsifier: | alkylaryl polyglycol ether |

To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, efficacy in % is determined. 100% means that all the spider mites have been killed; 0% means that none of the spider mites have been killed.

In this test, for example, the following compounds from the preparation examples show an efficacy of 100% at an application rate of 500 g/ha: 1-009, 1-016

In this test, for example, the following compounds from the preparation examples show an efficacy of 90% at an application rate of 500 g/ha: 1-031

In this test, for example, the following compounds from the preparation examples show an efficacy of 100% at an application rate of 100 g/ha: 1-001, 1-003, 1-004, 1-006, 1-010, 1-012, 1-013, 1-015, 1-017, 1-019, 1-022, 1-023, 1-024, 1-025, 1-026, 1-027, 1-028, 1-029, 1-033, 1-034, 1-035, 1-038, 1-039, 1-040, 1-041, 1-042, 1-043, 1-046, 1-047, 1-048, 1-052, 1-053, 1-054, 1-058, 1-060, 1-063, 1-064, 1-065, 1-067, 1-071, 1-073, 1-078, 1-081, 1-085, 1-087, 1-088, 1-089, 1-091, 1-092, 1-093, 1-094, 1-095, 1-096, 1-097, 1-098, 1-099, 1-100, 1-101, 1-108, 1-121, 2-001, 2-003, 2-004, 2-006

In this test, for example, the following compounds from the preparation examples show an efficacy of 90% at an application rate of 100 g/ha: 1-007, 1-011, 1-014, 1-018, 1-055, 1-068, 1-069, 1-076, 1-086

In this test, for example, the following compounds from the preparation examples show an efficacy of 100% at an application rate of 20 g/ha: 2-005

Anopheles Test (ANPHGB Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 100 mg/m$^2$: 1-001, 1-023, 1-024, 1-036, 1-040

In this test, for example, the following compounds from the preparation examples show efficacy of 90-100% at an application rate of 20 mg/m$^2$: 1-024, 1-127

Anopheles Test (ANPHFU Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Anopheles funestus* strain FUMOZ-R (Hunt et al., Med Vet Entomol. 2005 September; 19 (3):271-5) are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 100 mg/m$^2$: 1-001, 1-022, 1-023, 1-024, 1-025, 1-036, 1-037, 1-040, 1-073

In this test, for example, the following compounds from the preparation examples show efficacy of 90-100% at an application rate of 20 mg/m$^2$: 1-001, 1-022, 1-023, 1-024, 1-025, 1-026, 1-027, 1-036, 1-040, 1-081, 1-127

Aedes Test (AEDSAE Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Aedes aegypti* strain MONHEIM are placed onto the treated tile. The exposure time is 30 minutes.

24 hours after contact with the treated surface, mortality in % is determined. 100% means that all the mosquitoes have been killed; 0% means that none of the mosquitoes have been killed.

In this test, for example, the following compounds from the preparation examples show efficacy of 90-100% at an application rate of 100 mg/m$^2$: 1-001, 1-002, 1-003, 1-006, 1-010, 1-012, 1-013, 1-014, 1-016, 1-017, 1-019, 1-022, 1-023, 1-024, 1-025, 1-026, 1-027, 1-034, 1-035, 1-036, 1-037, 1-073, 1-081, 1-085, 1-094, 1-099, 1-100, 1-127, 2-001

In this test, for example, the following compounds from the preparation examples show efficacy of 90-100% at an application rate of 20 mg/m$^2$: 1-001, 1-002, 1-003, 1-006, 1-010, 1-012, 1-013, 1-014, 1-016, 1-017, 1-019, 1-022, 1-023, 1-024, 1-025, 1-026, 1-027, 1-034, 1-035, 1-036, 1-037, 1-040, 1-073, 1-081, 1-086, 1-094, 1-099, 1-100, 1-127, 2-001

The invention claimed is:

1. A compound of the formula (Ic)

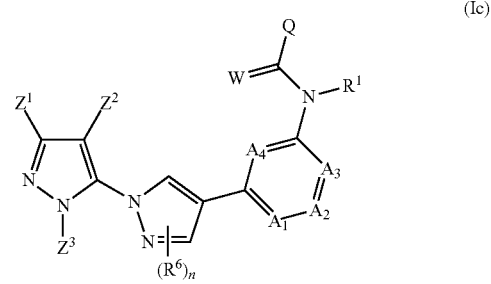

in which $R^1$ is hydrogen or $CH_3$;
$Z^1$ is $CF_2CF_3$;
$Z^2$ is $CF_3$;
$Z^3$ is $CH_3$,
$A_1$ is CH;
$A_2$ is CH or nitrogen;
$A_3$ is $CR^4$;
$R^4$ is fluorine; chlorine; hydrogen; or $CH_3$;
$A_4$ is $CR^5$,
$R^5$ is fluorine or hydrogen;
n is 0;
W is oxygen; and
Q is ethyl; isopropyl; t-butyl; cyclopentyl; phenoxyethyl; benzyloxymethyl; $CF_3CH_2$—; $CHF_2CF_2$—; MeOCH$_2$—; MeOCH$_2$CH$_2$—; 3-pyridinyl; 4-pyridinyl; 2-F-4-pyridinyl; 3-F-4-pyridinyl; 3-F-5-pyridinyl;

3-Cl-2-pyridinyl; 2-Cl-3-pyridinyl; 2-Cl-4-pyridinyl; 2-Cl-5-pyridinyl; 2,6-Cl$_2$-4-pyridinyl; 2-Cl-6-Me-4-pyridinyl; 2-Me-4-pyridinyl; 2-CN-5-pyridinyl; 2-F-5-pyridinyl; phenyl; 2-F-phenyl; 3-F-phenyl; 4-F-phenyl; 3,5-F$_2$-phenyl; 2,6-F$_2$-phenyl; 3-MeO-phenyl; 2,3-F$_2$-phenyl; 2-EtO-phenyl; 2-CF$_3$O-phenyl; 3-cyanophenyl; 4-CN-phenyl; phenylthiomethyl; 2-thiophenyl; 3-thiophenyl; 3-Cl-2-thiophenyl; 2-thiophenyl-methyl; 3-Cl-benzothiophen-2-yl; 3-Cl-6-Me-benzothiophen-2-yl; cyclopropyl; 1-CN-cyclopropyl; 1-Cl-cyclopropyl; 1-Me-cyclopropyl; 1-phenylcycloprop-1-yl; 1-oxazolyl; 5-methylisoxazol-4-yl; 2-pyrimidinyl; 4-pyrimidinyl; 7-(difluoromethyl)-5-methyl-[1,2,4]triazolo[1,5-a]pyrimidin-2-yl; 1-methyl-4-pyrazolyl; 1-Me-3-tBu-4-NO$_{2-5}$-pyrazolyl; 3-CF$_3$-4-Me-pyrazol-1-yl-methyl; (1,1-dimethyl)-2-fluoroethyl; cis/trans-4-MeO-cyclohex-1-yl; 1-Me-cyclohex-1-yl; 3-CF$_3$-4-F-phenyl; 3-CF$_3$-phenyl; 4-Me-phenyl; 2,6-(MeO)$_2$-phenyl; 4-(Me$_2$N)-phenyl; 2,4,6-(iPr)$_3$-phenyl; 3-Me-2-benzofuranyl; 2-CF$_3$-4-Me-furan-2-yl; 1,1,2,2-tetramethylethyl; (R)-1-F-ethyl; 2-Me-3-furanyl; 2-Me-prop-1-yl; 5-Me-thien-2-yl; 2,2-dimethylprop-1-yl; 1,1-dimethyl-2-ethoxyethyl; 2,3-dimethylphenyl; 2,2-difluoro-1,3-benzodioxol-5-yl; 3,4-dimethylphenyl; 3-Me, 4-F-phenyl; 3-F, 4-Me-phenyl; 3-F, 4-MeO-phenyl; 1,3-benzodioxol-5-yl; 4-Cl, 3-F-phenyl; 3-MeO, 4-Me-Ph; 3-EtO, 4-F-phenyl; 3-EtO-4-F-phenyl; 3-MeO-4-F-phenyl; 3-F-4-MeO-phenyl; 1-(4-Me-phenyl)cyclohex-1-yl; 3-CF$_3$-benzyl; 3-F-benzyl; 2-Cl-4-F-benzyl; 1-methyl-1-(3-Cl-phenyl)ethyl; 1-(4-Cl-phenyl)-cyclobut-1-yl; (rac)-1-phenylethyl; (rac)-phenyl-cyclopentylmethyl; (rac)-tetralin; (rac)-1-(4-Cl-phenyl)-2-methyl-prop-1-yl; (rac)-1-phenoxy-ethyl; (rac)-1-phenyl-prop-1-yl; (rac)-1-methylpropyl; 2-phenylethyl; N',N'-dimethyloxalyl-amide; 3-MeO, 4-F-phenyl; 3-F; or 4-MeO-phenyl.

2. The compound according to claim 1, in which R$^1$ is hydrogen.

3. The compound according to claim 1, in which R$^1$ is CH$_3$.

4. The compound according to claim 1, in which the compound is of the formula (Ic-1)

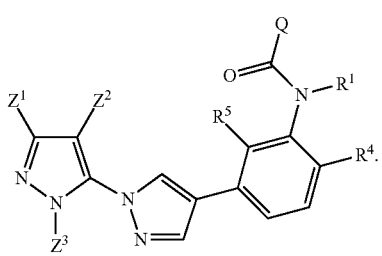

(Ic-1)

5. The compound according to claim 1, in which the compound is of the formula (Ic-2)

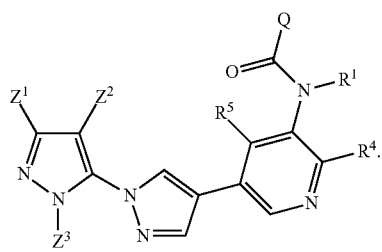

(Ic-2)

6. A method for control of at least one of insects, arachnids, and nematodes comprising administering an effective amount of the compound according to claim 1 of the formula (Ic).

7. A pharmaceutical composition comprising at least one compound comprising to claim 1 in combination with a pharmaceutically acceptable excipient and/or an auxiliary.

8. A medicament comprising the compound according to claim 1 in combination with a pharmaceutically acceptable excipient and/or an auxiliary.

9. A method of making a crop protection composition comprising combining the compound according to claim 1 with an extender and/or a surfactant.

10. A method for controlling pests, comprising administering an effective amount of the compound according to claim 1 to plants, seeds, crops, animals, pests and/or the pest's habitat.

11. A method for protection of propagation material of plants comprising administering an effective amount of the compound according to claim 1 to the plants or their propagation material.

12. The compound according to claim 1, in which R$^4$ is fluorine.

13. The compound according to claim 1, in which R$^4$ is chlorine.

14. The compound according to claim 1, in which R$^4$ is hydrogen.

15. The compound according to claim 1, in which R$^4$ is CH$_3$.

16. The compound according to claim 1, in which R$^5$ is hydrogen.

17. The compound according to claim 1, in which R$^5$ is fluorine.

* * * * *